(12) United States Patent
Das et al.

(10) Patent No.: US 10,358,418 B2
(45) Date of Patent: Jul. 23, 2019

(54) RESIN COMPOSITIONS

(71) Applicant: Novoset, LLC, Peapack, NJ (US)

(72) Inventors: Sajal Das, Bedmister, NJ (US); Paul Boothe, Brooklyn, NY (US); Patrick Shipman, Stirling, NJ (US)

(73) Assignee: Novoset, LLC, Peapack, NJ (US)

( * ) Notice: Subject to any disclaimer, the term of this patent is extended or adjusted under 35 U.S.C. 154(b) by 0 days.

(21) Appl. No.: 15/861,133

(22) Filed: Jan. 3, 2018

(65) Prior Publication Data

US 2018/0170873 A1 Jun. 21, 2018

Related U.S. Application Data

(63) Continuation of application No. 15/601,880, filed on May 22, 2017, now Pat. No. 9,902,695.

(60) Provisional application No. 62/435,369, filed on Dec. 16, 2016.

(51) Int. Cl.
| | |
|---|---|
| C07D 209/76 | (2006.01) |
| C08F 12/34 | (2006.01) |
| C08G 77/26 | (2006.01) |
| C08F 32/06 | (2006.01) |
| C08F 110/14 | (2006.01) |
| C08F 136/20 | (2006.01) |
| C08F 236/22 | (2006.01) |
| C08F 299/00 | (2006.01) |

(52) U.S. Cl.
CPC ............ *C07D 209/76* (2013.01); *C08F 12/34* (2013.01); *C08F 32/06* (2013.01); *C08F 110/14* (2013.01); *C08F 136/20* (2013.01); *C08F 236/22* (2013.01); *C08F 299/00* (2013.01)

(58) Field of Classification Search
CPC .............................. C07D 209/76; C08F 12/34
See application file for complete search history.

(56) References Cited

U.S. PATENT DOCUMENTS

| | | |
|---|---|---|
| 3,560,583 A | 2/1971 | Stewart, Jr. |
| 4,873,302 A | 10/1989 | Beuhler et al. |
| 5,127,158 A | 7/1992 | Nakano |
| 6,180,725 B1 | 1/2001 | Tsai et al. |
| 6,319,611 B1 | 11/2001 | Mathias et al. |
| 7,514,379 B2 | 4/2009 | Nishiguchi et al. |
| 7,638,564 B2 | 12/2009 | Amou et al. |
| 7,838,576 B2 | 11/2010 | Inoue et al. |
| 8,115,105 B2 | 2/2012 | Amou et al. |
| 8,420,210 B2 | 4/2013 | Amou et al. |
| 8,901,274 B2 | 12/2014 | Das et al. |
| 9,332,637 B2 | 5/2016 | Das et al. |
| 9,439,248 B2 | 9/2016 | Chen |
| 2004/0048997 A1 | 3/2004 | Sugo |
| 2008/0004367 A1 | 1/2008 | Takada et al. |
| 2008/0221261 A1 | 9/2008 | Amou et al. |
| 2014/0275377 A1 | 9/2014 | Yin et al. |
| 2015/0015505 A1 | 1/2015 | Lee et al. |
| 2016/0021739 A1 | 1/2016 | Li et al. |

FOREIGN PATENT DOCUMENTS

| | | |
|---|---|---|
| EP | 0441460 B1 | 11/1996 |
| GB | 899946 A | 6/1962 |
| JP | 2001253914 A | 9/2001 |
| JP | 2005134743 A | 5/2005 |
| WO | 2016000146 A1 | 1/2016 |

OTHER PUBLICATIONS

Invitation to Pay Additional Fees and Partial Search Report, dated Sep. 26, 2017 for PCT/US2017/033869.

*Primary Examiner* — Bijan Ahvazi
(74) *Attorney, Agent, or Firm* — Thomas M. Finetti; Charney IP Law LLC

(57) ABSTRACT

The present disclosure is directed to resins and to polymers, copolymers, and blends formed therefrom.

14 Claims, No Drawings

RESIN COMPOSITIONS

CROSS REFERENCE TO RELATED APPLICATIONS

The present application claims the benefit of the filing date of U.S. patent application Ser. No. 15/601,880 filed May 22, 2017, and claims the benefit of the filing date of U.S. Provisional Patent Application 62/435,369 filed Dec. 16, 2016, the disclosure of which is hereby incorporated by reference herein in its entirety.

FIELD OF THE DISCLOSURE

The present disclosure is directed to thermosetting resin compositions that are useful for the next-generation wireless standard (i.e. namely 5th generation mobile networks or "5G").

BACKGROUND OF THE DISCLOSURE 5G is the follow-up to the current wireless standard known as 4G or long term evolution (LTE). It is believed to be able to enable data transmission rates of more than 10 Gbps or 100 times the throughput of LTE. Basically, 5G technology consists of three separate elements—enhanced mobile broadband (1,000 times more capacity and one-tenth the latency), the Internet of Things (IOT) and other Wi-Fi based technology, and machine-to-machine (M2M) type communications.

Today's LTE networks (servers, router base station, etc.) are believed to operate from 700 MHz to 3.5 GHz. In comparison, 5G will not only co-exist with LTE, but will also operate in unlicensed or millimeter wave bands. This involves the spectrum band between 30 GHz and 300 GHz, which in turn enables more data capabilities.

Proposed next-generation technologies (5G) have higher performance requirements that cannot be achieved with many of the composite materials currently used in device production. The higher signal intensities required for 5G technologies will demand new composite materials that can maintain signal integrity (e.g. very low dielectric loss) and small circuit size (e.g. low dielectric constant) while maintaining the thermal, physical and mechanical properties desirable for PCB and other mobile devices.

BRIEF SUMMARY OF THE DISCLOSURE

In one aspect of the present disclosure is a resin having a general structure defined by Formulas (IA) and (IB):

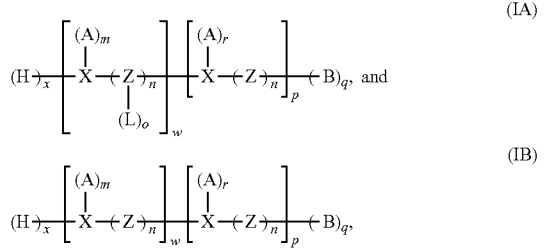

wherein X is a moiety comprising a cyclopentadiene-based ring; B is H or $X(A)_s$; L is a leaving group; each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms; Z is a bond or a straight-chain or branched, substituted or unsubstituted, aliphatic group having between 1 and 20 carbon atoms; m is an integer ranging from 1 to 5; n is 0 or 1; o is 0 or 1; p is 0 or an integer ranging from 1 to 150; q is 0 or 1; r is an integer ranging from 1 to 4; s is an integer ranging from 1 to 5; w is 0 or an integer ranging from 1 to 150; and x is 0 or 1.

In some embodiments, a dielectric value (Dk) of the resin ranges from about 1.5 to about 3. In some embodiments, the Dk value ranges from about 2.0 to about 2.8. In some embodiments, the Dk value is less than 2.6. In some embodiments, the Dk value is less than 2.4. In some embodiments, a dissipation value (Df) of the resin ranges from about 0.0001 to about 0.004. In some embodiments, the Df value ranges from about 0.0009 to about 0.003. In some embodiments, the Df value is less than about 0.002. In some embodiments, the Df value is less than about 0.001. In some embodiments, a glass transition temperature (Tg) of the resin is greater than 100° C. In some embodiments, a glass transition temperature (Tg) of the resin is at least 150° C.

In some embodiments, the resins of any of Formulas (IA) or (IB) may be reacted with a dienophile or heterodienophile. In some embodiments, the resins of any of Formulas (IA) or (IB) may be reacted with a compound having a maleimide group. In some embodiments, the resins of any of Formulas (IA) or (IB) may be reacted with bis-maleimide or an analog or derivative thereof. In some embodiments, the resins of any of Formulas (IA) or (IB) may be reacted with benzoquinone or an analog or derivative thereof. In some embodiments, the resins of any of Formulas (IA) or (IB) may be reacted with an acrylate or a bis-acrylate.

In some embodiments, the resins of any of Formulas (IA) or (IB) have a molecular weight ranging from between about 100 g/mol and about 500 g/mol. Of course, the skilled artisan will recognize that oligomers of the resins of Formulas (IA) or (IB) may have a molecular weight of greater than 500 g/mol. In other embodiments, the resins of any of Formulas (IA) or (IB) have a molecular weight ranging from between about 100 g/mol and about 400 g/mol. In yet other embodiments, the resins of any of Formulas (IA) or (IB) have a molecular weight ranging from between about 100 g/mol and about 200 g/mol. In some embodiments, the resins of any of Formulas (IA) or (IB) may be blended with another polymer or copolymer. In some embodiments, the resins of any of Formulas (IA) or (IB) may be reacted with a crosslinking agent.

In some embodiments, the moiety A has the general structure defined by Formula (IIB):

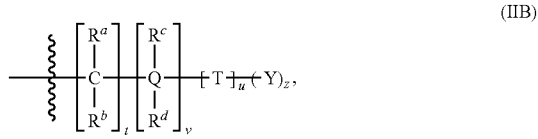

wherein Q is C, O, N, or S; $R^a$, $R^b$, $R^c$, $R^d$ are independently selected from H, F, a $C_1$ to $C_{10}$ linear or cyclic, saturated or unsaturated, branched or straight chain aromatic or aliphatic group; T is —$CH_2$—, -phenyl, or —$CH_2$-phenyl; Y is H, —$CH_3$, —CH=$CH_2$, —CH=CH—$CH_3$, or an alkyne group; t and v are independently 0 or an integer ranging from 1 to 20; u is 0 or 1; and z is an integer ranging from 1 to 5. In some embodiments, when T is -phenyl, or —$CH_2$-phenyl, and Y is —CH=$CH_2$, —CH=CH—$CH_3$, or an alkyne group, z is 1. In some embodiments, at least one of t or v is at least 1, and Y is selected from the group consisting of —CH=$CH_2$, —CH=CH—$CH_3$, or an alkyne group. In some embodiments, t, u, and v are each 0, and Y is selected from the group consisting of —CH=$CH_2$, —CH=CH—$CH_3$, or an alkyne group.

In some embodiments, the moiety A has the general structure defined by Formula (IID):

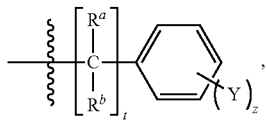

wherein $R^a$ and $R^b$ are independently selected from H, F, a $C_1$ to $C_{10}$ linear or cyclic, branched or straight chain aliphatic group; Y is H, —$CH_3$, —CH=$CH_2$, —CH=CH—$CH_3$, or alkyne; and t is 0 or an integer ranging from 1 to 20; z is an integer ranging from 1 to 5. In some embodiments, when Y is —CH=$CH_2$, —CH=CH—$CH_3$, or alkyne, z is 1. In some embodiments, the $R^a$ and $R^b$ are independently a $C_1$ to $C_6$ linear or cyclic, branched or straight chain aliphatic group. In some embodiments, z is 1 or 2. In other embodiments, z is 1.

In another aspect of the present disclosure are resins having the general structure defined by Formulas (IVA), (IVB), (IVC):

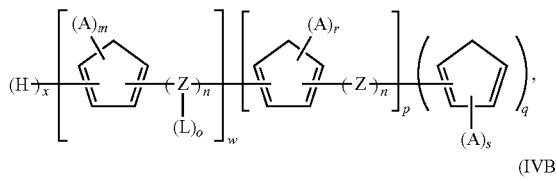

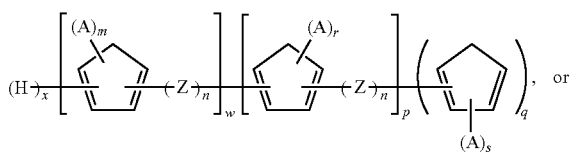

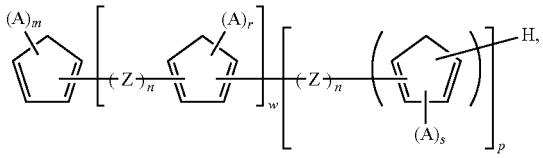

wherein L is a leaving group; each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms; Z is a bond or straight-chain or branched, substituted or unsubstituted, aliphatic group having between 1 and 20 carbon atoms; m is an integer ranging from 1 to 5; n is 0 or 1; o is 0 or 1; p is 0 or an integer ranging from 1 to 150; q is 0 or 1; r is an integer ranging from 1 to 4; s is an integer ranging from 1 to 5; w is 0 or an integer ranging from 1 to 150; and x is 0 or 1.

In some embodiments, each moiety A independently has the structure defined by Formula (IIA):

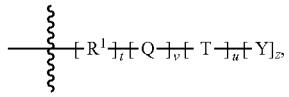

wherein $R^1$ is a bond, or a saturated or unsaturated straight-chain or branched, linear or cyclic, substituted or unsubstituted, aliphatic or aromatic group having from about 1 to about 10 carbon atoms, Q is a bond or a linking group optionally comprising a heteroatom; T is a bond or —$CH_2$—, -phenyl, or —$CH_2$-phenyl; Y is H, —$CH_3$, —CH=$CH_2$, —CH=CH—$CH_3$, or an alkyne group; t and v are independently 0 or an integer ranging from 1 to 20; u is 0 or 1; and z is an integer ranging from 1 to 5.

In some embodiments, each of the groups $(A)_r$, $(A)_m$ and $(A)_s$ of any of Formulas (IVA), (IVB), or (IVC) are different. In some embodiments, $(A)_m$ comprises a substituted or unsubstituted vinyl benzyl group; and wherein $(A)_s$ is —$CH_2$—CH=$CH_2$. In some embodiments, $(Z)_n$ is an unsubstituted alkyl group having from 2 to 6 carbon atoms. In some embodiments, the resin of Formulas (IVA), (IVB), (IVC) has the general structure:

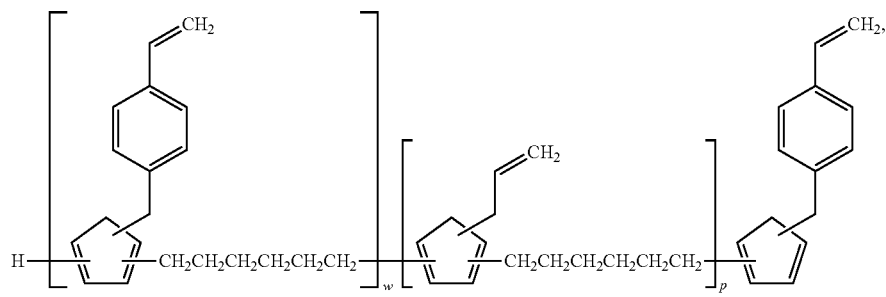

where w and p are independently an integer ranging from 1 to 150.

In some embodiments of the resins of Formulas (IVA), (IVB), and (IVC), n, q, and w and p are 1; o is 0 and x is 1; A comprises a moiety which terminates in a group selected from —CH=CH$_2$, —CH=CH—CH$_3$ or alkyne; and Z comprises an aliphatic group having at least three carbon atoms. In other embodiments of the compounds of Formulas (IVA), (IVB), and (IVC), n, q, and w are 1; o is 0 and x is 1 A comprises a moiety which terminates in a group selected from H or —CH$_3$; and Z comprises an aliphatic group having at least three carbon atoms. In other embodiments of the compounds of Formulas (IVA), (IVB), and (IVC), n, q, and w are 1; o is 0 and x is 1; A comprises a moiety which terminates in an alkyne group; and Z comprises an aliphatic group having at least three carbon atoms.

In some embodiments, the resins of any of Formulas (IVA), (IVB) or (IVC) may be reacted with a dienophile or heterodienophile. In some embodiments, the resins of any of Formulas (IVA) (IVB) or (IVC) may be reacted with a reagent having a maleimide group. In some embodiments, the resins of any of Formulas (IVB) or (IVC) may be reacted with bis-maleimide or an analog or derivative thereof. In some embodiments, the resins of any of Formulas (IVB) or (IVC) may be reacted with benzoquinone or an analog or derivative thereof. In some embodiments, the resins of any of Formulas (IVB) or (IVC) may be reacted with an acrylate or a bis-acrylate. In some embodiments, the resins of any of Formulas (IVA) (IVB) or (IVC) may be blended with another polymer or copolymer. In some embodiments, the resins of any of Formulas (IA) or (IB) may be reacted with a crosslinking agent.

In another aspect of the present disclosure are resins having the general structure defined by Formulas (VA) or (VB):

(VA)

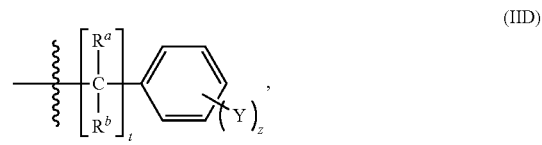

(VB)

wherein each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms; Z is a bond or straight-chain or branched, substituted or unsubstituted, aliphatic group having between 1 and 20 carbon atoms; m is an integer ranging from 1 to 5; n is 0 or 1; o is 0 or 1; p is 0 or an integer ranging from 1 to 150; q is 0 or 1; r is an integer ranging from 1 to 4; s is an integer ranging from 1 to 5; w is 0 or an integer ranging from 1 to 150; and x is 0 or 1.

In some embodiments, p is an integer ranging from between 1 and 20, A is hydrogen, X is derived from cyclopentadiene, and (Z)$_n$ is a straight-chain or branched aliphatic group having between 1 and 6 carbon atoms. In some embodiments, p is an integer ranging from between 1 and 20, X is derived from cyclopentadiene substituted with one (A) moiety that is other than hydrogen, and B is X(A)$_1$.

In some embodiments, the resins of any of Formulas (VA) or (VB) may be reacted with a dienophile or heterodienophile. In some embodiments, the resins of any of Formulas (VA) or (VB) may be reacted with a compound having a maleimide group. In some embodiments, the resins of any of Formulas (VA) or (VB) may be reacted with bis-maleimide or an analog or derivative thereof. In some embodiments, the resins of any of Formulas (VA) or (VB) may be reacted with benzoquinone or an analog or derivative thereof. In some embodiments, the resins of any of Formulas (VA) or (VB) may be reacted with an acrylate or a bis-acrylate. In some embodiments, the resins of any of Formulas (VA) or (VB) may be blended with another polymer or copolymer. In some embodiments, the resins of any of Formulas (IA) or (IB) may be reacted with a crosslinking agent.

In another aspect of the present disclosure is a resin having a structure defined by Formula (VI):

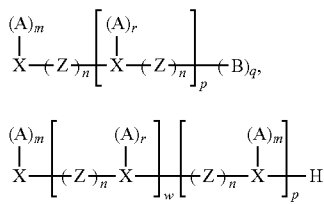

(VI)

wherein X is cyclopentadiene; B is H; (Z)$_n$ is a bond; m is ranges from 1 to 5; and A has the structure defined by Formula (IID):

(IID)

$R^a$ and $R^b$ are independently selected from H, F, a C$_1$ to C$_{10}$ linear or cyclic, branched or straight chain aliphatic group; Y is H, —CH$_3$, —CH=CH$_2$, —CH=CH—CH$_3$, or alkyne; and t is 0 or an integer ranging from 1 to 20. In some embodiments, t is 1; and $R^a$ and $R^b$ are each H. In some embodiments, Y is —CH=CH$_2$. In some embodiments, m is 2, and a first A group comprises a vinyl benzyl moiety; and wherein a second A group is —CH$_2$—CH=CH$_2$.

In some embodiments, the resin has the structure:

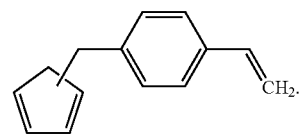

In some embodiments, the resins of Formula (VI) may be reacted with a dienophile or heterodienophile. In some embodiments, the resins of Formula (VI) may be reacted with a compound having a maleimide group. In some embodiments, the resins of Formula (VI) may be reacted with bis-maleimide or an analog or derivative thereof. In some embodiments, the resins of Formula (VI) may be reacted with benzoquinone or an analog or derivative thereof. In some embodiments, the resins of Formula (VI) may be reacted with an acrylate.

In another aspect of the present disclosure is a resin having a structure defined by Formula (VII):

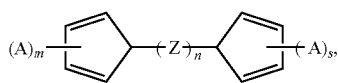
(VII)

wherein Z has the structure defined by Formula (IIIA):

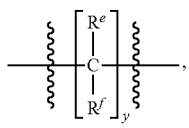
(IIIA)

wherein $R^e$ and $R^f$ are independently selected from H, F, or a straight chain or branched alkyl group having between 1 and 6 carbon atoms; and y is an integer ranging from between 1 and about 20; m and s are independently an integer ranging from between 1 and about 5; each A is independently selected from H or a moiety having a structure defined by Formula (IIC):

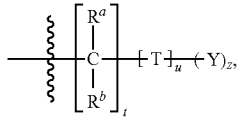
(IIC)

wherein $R^a$ and $R^b$ are independently selected from H, F, a $C_1$ to $C_{10}$ linear or cyclic, branched or straight chain aliphatic group; T is —$CH_2$—, -phenyl, or —$CH_2$-phenyl; Y is H, —$CH_3$, —$CH$=$CH_2$, —$CH$=$CH$—$CH_3$, or alkyne; t is 0 or an integer ranging from 1 to 20; u is 0 or 1; and z is an integer ranging from 1 to 5. In some embodiments, n is 1, and $R^e$ and $R^f$ are each H. In some embodiments, A is H. In some embodiments, y is 6. In some embodiments, y is 3. In some embodiments, the resin has the structure selected from the group consisting of:

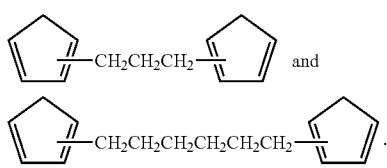

In some embodiments, at least one of $(A)_m$ or $(A)_s$ comprise a moiety having the structure defined by Formula (IIC):

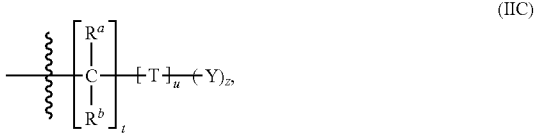
(IIC)

where $R^a$ and $R^b$ are each H. In some embodiments, Y is —$CH$=$CH_2$. In some embodiments, $R^e$ and $R^f$ are each H. In some embodiments, y is 6. In some embodiments, m is 1 and s is 0. In some embodiments, the resin has the structure:

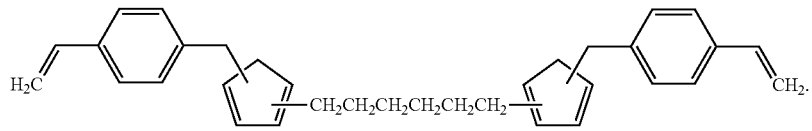

In some embodiments, $(A)_m$ and $(A)_s$ each comprise a different moiety defined by Formula (IIC):

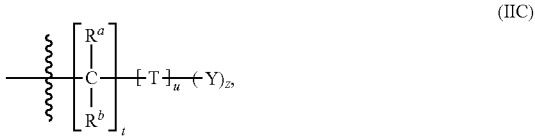
(IIC)

wherein $R^a$ and $R^b$ are independently selected from H, F, a $C_1$ to $C_{10}$ linear or cyclic, branched or straight chain aliphatic group; T is —$CH_2$—, -phenyl, or —$CH_2$-phenyl; Y is H, —$CH_3$, —$CH$=$CH_2$, —$CH$=$CH$—$CH_3$, or alkyne; t is 0 or an integer ranging from 1 to 20; u is 0 or 1; and z is an integer ranging from 1 to 5.

In some embodiments, for $(A)_m$, t is 1 and T is phenyl; and for $(A)_s$ t is 1 and u is 0. In some embodiments, for $(A)_m$, t is 1; T is phenyl, and Y is —$CH$=$CH_2$; and for $(A)_s$ t is 1, u is 0, and Y is —$CH$=$CH_2$. In some embodiments, the resin has the structure:

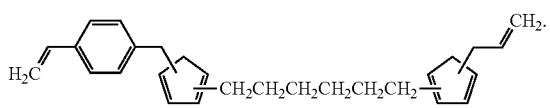

In another aspect of the present disclosure are low dielectric materials having such characteristics which particularly useful as materials for use in the aerospace industry, communications industry, and electronics industry. For example, the resins, polymers, blends, etc. disclosed herein may be used in printed circuit boards, as substrates for integrated circuits, or as substrates or packaging for other microelectronic circuits or applications.

In another aspect of the present disclosure is a composition comprising a first resin of Formulas (IA) or (IB) and a second resin of Formulas (IA) or (IB), wherein each of the first and second resins are different (e.g. differing in at least one moiety and/or the number of repeat groups and/or the positioning of any moiety on any ring). In some embodiments, the first resin is present in the composition in an amount ranging from between about 1% to about 99% by weight of the composition. In some embodiments, the first resin is present in the composition in an amount ranging from between about 10% to about 90% by weight of the composition. In some embodiments, the first resin is present in the composition in an amount ranging from between about 20% to about 80% by weight of the composition. In some embodiments, the first resin is present in the composition in an amount ranging from between about 30% to about 70% by weight of the composition. In some embodiments, the first resin is present in the composition in an amount ranging from between about 40% to about 60% by weight of the composition. In some embodiments, the first resin is present in the composition in an amount ranging from between about 50% to about 50% by weight of the composition. In some embodiments, the first resin is present in the composition in an amount ranging from between about 60% to about 40% by weight of the composition. In some embodiments, the first resin is present in the composition in an amount ranging from between about 70% to about 30% by weight of the composition. In some embodiments, the first resin is present in the composition in an amount ranging from between about 80% to about 20% by weight of the composition. In some embodiments, the first resin is present in the composition in an amount ranging from between about 90% to about 10% by weight of the composition. In some embodiments, the first resin is present in the composition in an amount ranging from between about 99% to about 1% by weight of the composition.

In some embodiments, the composition further comprises at least a third resin of Formulas (IA) or (IB), wherein the third resin is different than the first and second resins. Of course, the skilled artisan will appreciate that the first resin component and the second resin component may be provided in any ratio relative to one another. Likewise, any additional resins (nth resins) that are added to the composition may also be present in any ratio.

In another aspect of the present disclosure is a polymer (including copolymers and interpenetrating polymer networks, as defined herein) derived from one or more resins of Formulas (IA) or (IB). In some embodiments, the at least one of the resins of Formulas (IA) or (IB) comprises at least one A moiety terminating in one of a —CH=CH$_2$ group, alkyne group, or a —CH=CH—CH$_3$ group. In some embodiments, the polymer further comprises an additive selected from the group consisting of adhesion agents, peroxides/crosslinking agents, antioxidants, flame retardants, diluents and fillers. In some embodiments, the polymers derived from one or more resins of Formulas (IA) or (IB) may be reacted with a dienophile or a crosslinking agent. In some embodiments, the polymers derived from one or more resins of Formulas (IA) or (IB) may be blended with another polymer that is not derived from one or more resins of Formulas (IA) or (IB). In some embodiments, the Dk value ranges from about 2.0 to about 2.8. In some embodiments, the Df value ranges from about 0.0001 to about 0.004.

In another aspect of the present disclosure is a co-polymer derived from a first resin of Formulas (IA) or (IB) and a second resin of Formulas (IA) or (IB), wherein the first and second resins are different.

In another aspect of the present disclosure is a co-polymer (including interpenetrating polymer networks, as defined herein) derived from a resin of any of Formulas (IA) or (IB), and a second component that differs from the resin of Formulas (IA) or (IB). In some embodiments, the second component is selected from the group consisting of polyethylenes, polypropylenes, polybutylenes, low vinyl polybutadienes (predominantly 1,3 addition), high vinyl polybutadienes (significant 1,2 addition), polystyrenes, butadiene-styrene copolymers, SMA polymers, ABS polymers, polydicyclopentadienes, epoxies, polyurethanes, cyanate esters, poly(phenylene oxide), EPDM polymers, cyclic olefin copolymers (COC), polyimides, bismaleimides, phosphazenes, olefin-modified phosphazenes, acrylates, vinyl esters, polylactones, polycarbonates, polysulfones, polythioethers, polyetheretherketones (PEEK), polydimethylsiloxanes (PDMS), polyethylene terephthalates (PET), polybutylene terephthalates (PBT), and other commercially-available polymers. In some other embodiments, the second component is selected from the group consisting of styrene, divinylbenzene, 1,2-bis(vinylphenyl)ethane, vinylbenzyl ether compounds, vinyl ether compounds, allyl ether compounds, vinylphenyl monomers, vinyl monomers, allyl monomers, or derivatives of such components.

In another aspect of the present disclosure is a composition comprising (a) either (i) a resin of any of Formulas (IA) or (IB); (ii) a polymer formed from a resin of any of Formulas (IA) or (IB); or (iii) an oligomer formed from a resin of any of Formulas (IA) or (IB); and (b) a suitable solvent, the solvent being present in an amount ranging from about 1% to about 99% by total weight of the composition.

In another aspect of the present disclosure is a resin having the general structure defined by any of Formulas (XIIC) or (XIID):

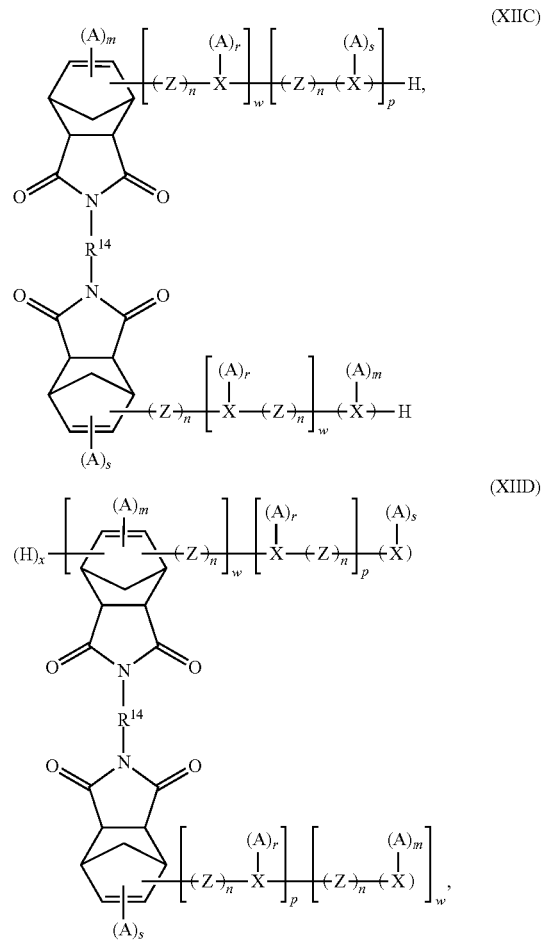

wherein X is a moiety comprising a cyclopentadiene-based ring;

Z has the structure defined by Formula (IIIA):

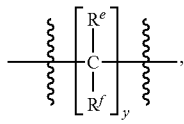

(IIIA)

where $R^e$ and $R^f$ are independently selected from H, F, or a straight chain or branched alkyl group having between 1 and 6 carbon atoms; and y is an integer ranging from between 1 and about 20;

the moiety A is H or a moiety having a structure defined by Formula (IIC):

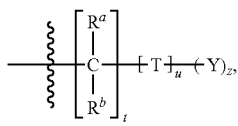

(IIC)

wherein $R^a$ and $R^b$ are independently selected from H, F, a $C_1$ to $C_{10}$ linear or cyclic, branched or straight chain aliphatic group; T is $-CH_2-$, -phenyl, or $-CH_2$-phenyl; Y is H, $-CH_3$, $-CH=CH_2$, $-CH=CH-CH_3$, or alkyne; m is an integer ranging from 1 to 5; n is 0 or 1; p is 0 or an integer ranging from 1 to 150; r is an integer ranging from 1 to 4; t is 0 or an integer ranging from 1 to 20; u is 0 or 1; and w is 0 or an integer ranging from 1 to 150; x is 0 or 1, z is an integer ranging from 1 to 5;

$R^{13}$ is a saturated or unsaturated, straight-chain or branched, linear or cyclic, substituted or unsubstituted, aliphatic or aromatic group having between 1 and 50 carbon atoms, and which may be substituted with one or more heteroatoms selected from O, N, or S;

$R^{14}$ is a saturated or unsaturated, straight-chain or branched, linear or cyclic, substituted or unsubstituted, aliphatic or aromatic group having between 1 and 40 carbon atoms; $-(R^{13})_k-R^{15}-$, $-R^{15}-(R^{13})_k-$ or $-R^{15}-(R^{13})_k-R^{15}-$;

each $R^{15}$ is independently a saturated or unsaturated, straight-chain or branched, linear or cyclic, substituted or unsubstituted, aliphatic or aromatic group having between 1 and 40 carbon atoms; and k is an integer ranging from 1 to 10.

In some embodiments, $R^{14}$ comprises -[Aryl]-[Alkyl]-[Aryl], where each aryl group may be independently substituted or unsubstituted, and where the alkyl group comprises between 1 and 20 carbon atoms. In some embodiments, each [Aryl] group is optionally substituted with a $C_1$-$C_{10}$ straight chain or branched alkyl group.

In some embodiments, $R^{14}$ has the structure defined by Formula (XIVa):

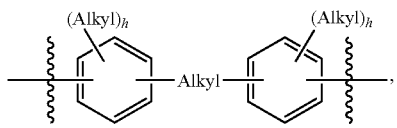

(XIVa)

wherein each alkyl group is independently straight chain or branched and comprises between 1 and 10 carbon atoms; and where each h is independently 0 or an integer ranging from 1 to 4.

In some embodiments, the resins any of Formulas (XIIC) or (XIID) have a dielectric value (Dk) ranging from about 1.5 to about 3. In some embodiments, the resins of any of Formulas (XIIC) or (XIID) have a dissipation value (Df) ranging from about 0.0001 to about 0.004.

In another aspect of the present disclosure is a composition comprising a blend of one or more compounds of any of Formulas (XIIC) or (XIID) In some embodiments, a ratio of a first compound of any of Formulas (XIIC) or (XIID) to a second compound of any of any of Formulas (XIIC) or (XIID) ranges from about 1:10 to about 10:1. In some embodiments, the ratio ranges from about 1:5 to about 5:1. In some embodiments, the ratio ranges from about 1:2 to about 2:1.

In another aspect of the present disclosure is a compound having a structure defined by Formula (XIIE):

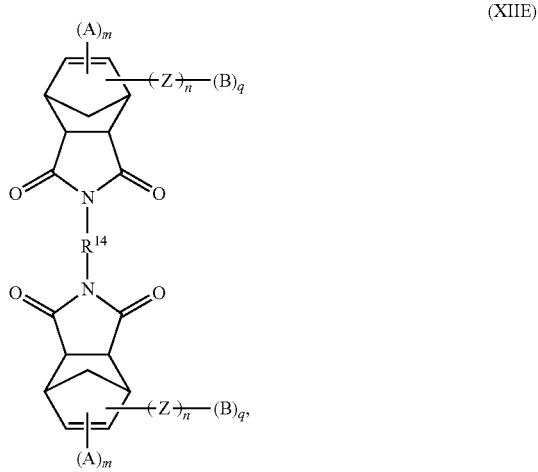

(XIIE)

wherein $R^{14}$ is a saturated or unsaturated, straight-chain or branched, linear or cyclic, substituted or unsubstituted, aliphatic or aromatic group having between 1 and 40 carbon atoms; $-(R^{13})_k-R^{15}-$, $-R^{15}-(R^{13})_k-$ or $-R^{15}-(R^{13})_k-R^{15}-$;

$R^{13}$ is a saturated or unsaturated, straight-chain or branched, linear or cyclic, substituted or unsubstituted, aliphatic or aromatic group having between 1 and 50 carbon atoms, and which may be substituted with one or more heteroatoms selected from O, N, or S; each $R^{15}$ is independently a saturated or unsaturated, straight-chain or branched, linear or cyclic, substituted or unsubstituted, aliphatic or aromatic group having between 1 and 40 carbon atoms; k is an integer ranging from 1 to 10;

each B is H or $X(A)_s$;

X is a moiety comprising a cyclopentadiene-based ring;

each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

each Z is a bond or straight-chain or branched, substituted or unsubstituted, aliphatic group having between 1 and 20 carbon atoms; each m is an integer ranging from 1 to 5; each n is 0 or 1; each q is 0 or 1; and each s is an integer ranging from 1 to 5.

In some embodiments, each A within Formula (XIIE) is independently H or a moiety having a structure defined by Formula (IIC):

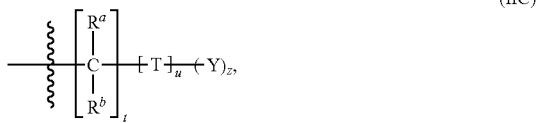

wherein $R^a$ and $R^b$ are independently selected from H, F, a $C_1$ to $C_{10}$ linear or cyclic, branched or straight chain aliphatic group; T is —$CH_2$—, -phenyl, or —$CH_2$-phenyl; Y is H, —$CH_3$, —$CH=CH_2$, —$CH=CH$—$CH_3$, or alkyne; t is 0 or an integer ranging from 1 to 20; u is 0 or 1; and z is an integer ranging from 1 to 5. In some embodiments, t is 1; $R^a$ and $R^b$ are each H; and Y is —$CH=CH_2$. In some embodiments, T is phenyl and u is 1.

In some embodiments, $R^{14}$ has the structure defined by Formula (XIVa):

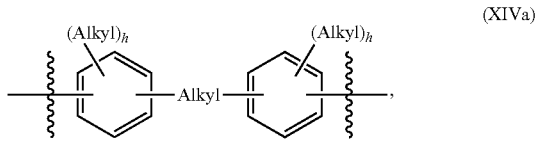

wherein each -[Alkyl]- group is independently straight chain or branched and comprises between 1 and 10 carbon atoms; and where each h is independently 0 or an integer ranging from 1 to 4. In some embodiments, at least one (Alkyl)$_h$ group is —$CH_3$. In some embodiments, $R^{14}$ comprises a substituted phenyl group. In some embodiments, $R^{14}$ comprises a branched alkyl group comprising between 1 and 10 carbon atoms.

In some embodiments, the compound of Formula (XIIE) has the structure defined by Formula (XIIF):

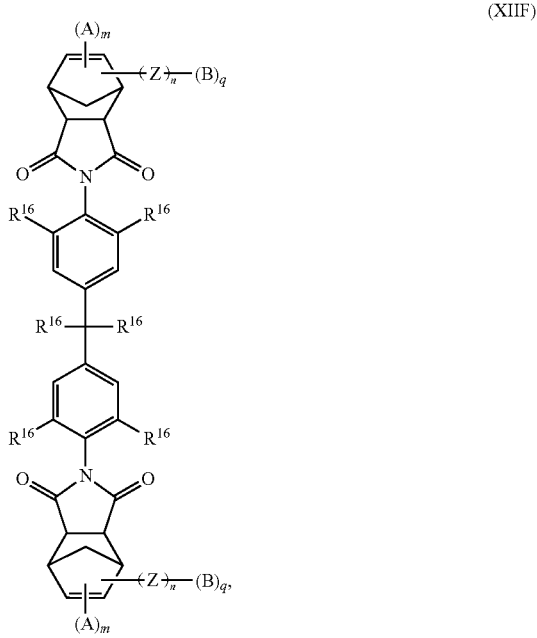

wherein each $R^{16}$ is independently H or a substituted or unsubstituted, linear or branched, linear or cyclic alkyl group having between 1 and 10 carbon atoms.

In some embodiments, each $R^{16}$ is independently H or a straight chain or branched alkyl group having from 1 to 4 carbons. In some embodiments, n and q are 0, and wherein at least one (A)$_m$ moiety comprises a vinyl benzyl group. In some embodiments, the compound has a Dk value ranging from about 1.5 to about 3.

In some embodiments, the compound has a Df value ranging from about 0.0001 to 0.004. In some embodiments, the compound has a Tg value of greater than 100° C.

In another aspect of the present disclosure is a composition comprising a blend of one or more compounds of any of Formulas (XIIE) or (XIIF). In some embodiments, a ratio of a first compound of any of Formulas (XIIE) or (XIIF) to a second compound of any of any of Formulas (XIIE) or (XIIF) ranges from about 1:10 to about 10:1. In some embodiments, the ratio ranges from about 1:5 to about 5:1. In some embodiments, the ratio ranges from about 1:2 to about 2:1.

In another aspect of the present disclosure is a reaction product of:

(i) a compound defined by Formulas (IA) or (IB):

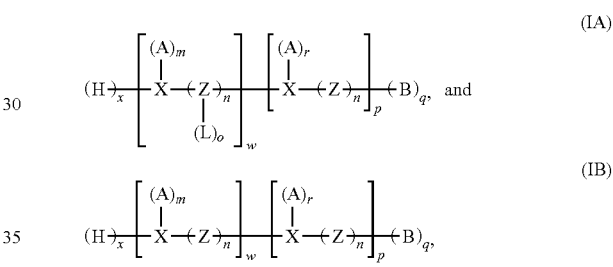

wherein X is a moiety comprising a cyclopentadiene-based ring; B is H or X(A)$_s$; L is a leaving group; each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms; Z is a bond or straight-chain or branched, substituted or unsubstituted, aliphatic group having between 1 and 20 carbon atoms; m is an integer ranging from 1 to 5; n is 0 or 1; o is 0 or 1; p is 0 or an integer ranging from 1 to 150; q is 0 or 1; r is an integer ranging from 1 to 4; s is an integer ranging from 1 to 5; w is 0 or an integer ranging from 1 to 150; x is 0 or 1; and (ii) a dienophile. In some embodiments, the dienophile is selected from the group consisting of a bis-maleimide, a derivative of a bis-maleimide, a maleic anhydride, a derivative of a maleic anhydride, a benzoquinone, a derivative of a benzoquinone, bis-acrylate, and an acrylate. In some embodiments, the reaction products have a dielectric value ranging from about 1.5 to about 3. In some embodiments, the reaction products have a dissipation value ranging from about 0.0001 to about 0.004.

In another aspect of the present disclosure is a product formed by reacting:

(i) a resin having the structure defined by Formula (VI):

wherein X is a moiety comprising a cyclopentadiene-based ring; B is H or $X(A)_s$; each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms; Z is a bond or straight-chain or branched, substituted or unsubstituted, aliphatic group having between 1 and 20 carbon atoms; m is an integer ranging from 1 to 5; n is 0 or 1; q is 0 or 1; and s is an integer ranging from 1 to 5; and
(ii) a bis-maleimide.

In some embodiments, the bis-maleimide has a structure selected from the group consisting of:

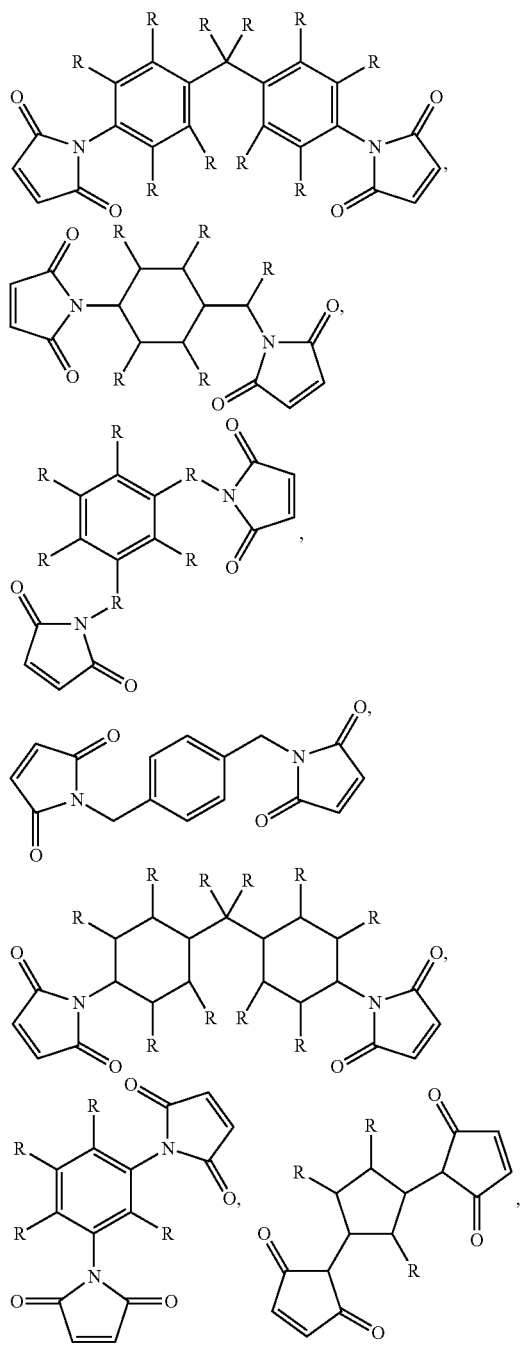

wherein each R is independently selected from hydrogen, an aryl group, a substituted aryl group, an aliphatic group, a substituted aliphatic group, a cyclic aliphatic group, and a substituted cyclic aliphatic group.

In some embodiments, the bis-maleimide is selected from the group consisting of 1,6'-bismaleimide-(2,2,4-trimethyl) hexane, 4,4'-Diphenylmethanebismaleimide, Polyphenylmethanebismaleimide, N,N'-(4-methyl-m-phenylene)-bismaleimide, N,N'-m-phenylenebismaleimide, bisphenol A diphenyl ether bismaleimide, 3,3'-dimethyl-5,5'-diethyl-4,4'-diphenylmethane bismaleimide, N,N'-[Methylenebis(2,6-diethyl-4,1-phenylene)]bis(maleimide), N,N'-[Methylenebis (2-isopropyl-6-methyl-4,1-phenylene)]bis(maleimide), 1,2-bis(maleimido)ethane, 1,4-bis(maleimido)butane, and 1,6-bis(maleimido)hexane; Bismaleimides derived from C30-C40 dimer acids; and bismaleimides with longer alkyl bridging groups such as those sold by Designer Molecules Inc. (BMI-689 and BMI-3000).

In some embodiments, the product has a Dk value ranging from about 1.5 to about 3. In some embodiments, product has a Df value ranging from about 0.0001 to 0.004.

In another aspect of the present disclosure are kits comprising any of the resins, polymers, blends, etc. disclosed herein. In some embodiments, the resins, polymers, blends, etc. are mixed with a suitable solvent. In some embodiments, the kits comprise multiple resins, polymers, blends, etc., where each of the resins, polymers, blends, etc. are provided in a separate container. In some embodiments, the kits include a resin and other reactants, reagents, or solvents. For example, a kit may include a resin of any of Formulas (IA) or (IB) and also may include a bis-maleimide, such that the resin and the bis-maleimide may be reacted to form a product. In some embodiments, the kits further comprise instructions.

Applicants have surprisingly discovered that the resins, polymers, copolymers, and compositions described herein have a dielectric value ranging from about 1.5 to about 3, and/or a dissipation value ranging from about 0.0001 to about 0.004, allowing the resins, polymers, copolymers, and compositions to be materials suitable for use various applications across many industries. Applicants have also surprisingly discovered that the resins, polymers, copolymers, and compositions are suitable for use in high speed communications applications (e.g. 5G communication systems, devices, and networks).

DETAILED DESCRIPTION

An object of the disclosure is to provide a dielectric material with low dielectric loss, which has excellent dielectric properties, low coefficient of thermal expansion and low water absorption.

Definitions

It should also be understood that, unless clearly indicated to the contrary, in any methods claimed herein that include more than one step or act, the order of the steps or acts of the method is not necessarily limited to the order in which the steps or acts of the method are recited. It should also be understood that where a variable (e.g. "w") is used more than once in any formula or chemical structure, that each use of the variable in the formula or chemical structure is independent from any other use, unless explicitly noted otherwise. For example, if the variable "w" is used twice within the same formula, each "w" may be the same or different, i.e. if "w" is defined as 0 or an integer ranging from 1 to 150, each "w" may independently be selected from 0 or an integer ranging from 1 to 150. Likewise, and again by way of example, if the moiety "$R^5$" is defined as —CH— or —C—$R^{12}$, then each time $R^5$ is used in a formula or chemical structure, each $R^5$ may independently be selected from —CH— or —C—$R^{12}$.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of."

As used herein, the term "alkyl" refers to a straight or branched hydrocarbon chain that comprises a fully saturated (no double or triple bonds) hydrocarbon group. By way of example only, the alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). As noted further herein, the alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "alkenyl" refers to an alkyl group that contains in the straight or branched hydrocarbon chain one or more double bonds. An alkenyl group may be unsubstituted or substituted.

As used herein, the term "alkynyl" refers to an alkyl group that contains in the straight or branched hydrocarbon chain one or more triple bonds. An alkynyl group may be unsubstituted or substituted.

As used herein, the term "aryl" means an aromatic carbocyclic radical or a substituted carbocyclic radical containing preferably from 6 to 10 carbon atoms, such as phenyl or naphtyl or phenyl or naphtyl, optionally substituted by at least one of the substituents selected in the group constituted by alkyl, alkenyl, alkynyl, aryl, aralkyl, hydroxy, alkoxy, aryloxy, aralkoxy, carboxy, aroyl, halo, nitro, trihalomethyl, cyano, alkoxy carbonyl, aryloxycarbonyl, aralkoxycarbonyl, acylamino, aroylamino, carbamoyl, alkylcarbamoyl, dialkylcarbamoyl, alkylthio, arylthio, alkylene or —NYY' where Y and Y' are independently hydrogen, alkyl, aryl, or aralkyl.

As used herein, the term "blend" refers, in some embodiments, to a mixture of two or more different species of resins or a resin and another polymer or copolymer.

As used herein, the terms "cure" or "curing" refer to processes of hardening a resin material.

As used herein, "cycloalkyl" of like terms (e.g. a cyclic alkyl group) refer to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl or aryl group, or the total number of carbon atoms and heteroatoms in a heteroalkyl, heterocyclyl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, the terms "halogen atom" or "halogen" mean any one of the radio-stable atoms of column 7 of the Periodic Table of the Elements, such as, fluorine, chlorine, bromine and iodine.

As used herein, the term "interpenetrating network," in accordance with the definition adopted by the IUPAC, refers to a polymeric system comprising two or more networks which are at least partially interlaced on a molecular scale, to form both chemical and physical bonds between the networks. The networks of an IPN cannot be separated unless chemical bonds are broken. In other words, an IPN structure represents two or more polymer networks that are partially chemically cross-linked and/or partially physically entangled.

As used herein, the term "polymer" is defined as being inclusive of homopolymers, copolymers, interpenetrating networks, and oligomers. Thus, the term polymer may be used interchangeably herein with the term homopolymers, copolymers, interpenetrating polymer networks, etc. The term "homopolymer" is defined as a polymer derived from a single species of monomer. The term "copolymer" is defined as a polymer derived from more than one species of monomer, including copolymers that are obtained by copolymerization of two monomer species, those obtained from three monomers species ("terpolymers"), those obtained from four monomers species ("quaterpolymers"), etc. The term "oligomer" is defined as a low molecular weight polymer in which the number of repeating units does not exceed twenty. The term "copolymer" is further defined as being inclusive of random copolymers, alternating copolymers, graft copolymers, and block copolymers. Copolymers, as that term is used generally, include interpenetrating polymer networks. The term "random copolymer" is defined as a copolymer comprising macromolecules in which the probability of finding a given monomeric unit at any given site in the chain is independent of the nature of the adjacent units. In a random copolymer, the sequence distribution of monomeric units follows Bernoullian statistics. The term "alternating copolymer" is defined as a copolymer comprising macromolecules that include two species of monomeric units in alternating sequence.

Whenever a group or moiety is described as being "substituted" or "optionally substituted" (or "optionally having" or "optionally comprising") that group may be unsubstituted or substituted with one or more of the indicated substituents. Likewise, when a group is described as being "substituted or unsubstituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, cyanate, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, ether, amino (e.g. a mono-substituted amino group or a di-substituted amino group), and protected derivatives thereof. Any of the above groups may include one or more heteroatoms, including O, N, or S. For example, where a moiety is substituted with an alkyl group, that alkyl group may comprise a heteroatom selected from O, N, or S (e.g. —($CH_2$—$CH_2$—O—$CH_2$—$CH_2$)—).

The term "prepreg" as used herein refers to a reinforcing fabric which has been pre-impregnated with a resin system.

Resins or Compositions Comprising More than One Resin

In one aspect of the present disclosure are resins, including resins defined by Formulas (IA) and (IB). In another aspect of the present disclosure are compositions comprising mixtures of the resins of Formulas (IA) and (IB). For example, a composition may comprise a first resin of Formula (IA) and a second resin of Formula (IB), wherein the first and second resins differ in at least one substituent or moiety or in the number of any repeating groups. Of course, the skilled artisan will appreciate that any composition may comprise any number of resins of Formulas (IA) or (IB), and any of the different resins may be present in the same or differing amounts within the composition. By way of a further example, a composition may comprise a first resin of Formulas (IA) or (IB), a second resin of Formulas (IA) or (IB), and a third resin of Formulas (IA) or (IB), wherein each of the first, second, and third resins differ in at least one substituent, and where the first resin is present in an amount ranging from between about 20% to about 40% by weight of the composition, the second resin is present in an amount ranging from 10% to about 30% by weight of the composition, and the third resin constitutes the remainder of the composition by weight of the composition.

In one aspect of the present disclosure are resins having the structure defined by Formulas (IA) and (IB):

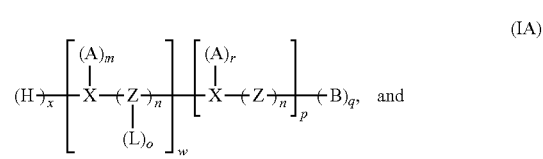

(IA)

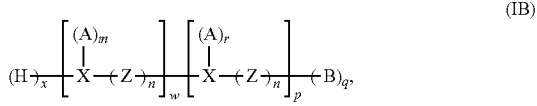

wherein

X is a moiety comprising a cyclopentadiene-based ring;
B is H or $X(A)_s$;
L is a leaving group.

each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

Z is a bond or straight-chain or branched, substituted or unsubstituted, aliphatic group having between 1 and 20 carbon atoms;

m is an integer ranging from 1 to 5;
n is 0 or 1;
o is 0 or 1;
p is 0 or an integer ranging from 1 to 150;
q is 0 or 1;
r is an integer ranging from 1 to 4;
s is an integer ranging from 1 to 5;
w is 0 or an integer ranging from 1 to 150; and
x is 0 or 1.

The skilled artisan will appreciate that in certain embodiments of Formula (IA) or (IB) where n is 0, Z may be a bond.

When it is denoted that any of the resins of Formulas (IA) or (IB) may differ from one another, it is meant that the resins may differ (i) in any moiety constituting the resin; (ii) the number of any of the repeat groups of the moiety that are present, (iii) the positioning of any moiety along any cyclic or aromatic group; and/or (iv) isomeric or stereochemical differences between the various moieties and/or groups.

The skilled artisan will appreciate that any group X, or for that matter any group B when B is $X(A)_s$, may be substituted with any number of A groups as denoted in Formulas (IA) and (IB). Where any single X group comprises multiple A groups, each of the A groups may be the same or different. For example, where X is derived from cyclopentadiene and m is 2, X may be substituted with a first A group and with a second A group, where the first and second A groups are different. Likewise, different X groups may comprise a same or a different number of A groups and, of course, the same or different A groups, without limitation.

In some embodiments, p is an integer ranging from 1 to 100. In other embodiments, p is an integer ranging from 1 to 75. In yet other embodiments, p is an integer ranging from 1 to 50. In further embodiments, p is an integer ranging from 1 to 20. In even further embodiments, p is an integer ranging from 1 to 10. In yet further embodiments, p is 0. In some embodiments, w is an integer ranging from 1 to 100. In other embodiments, w is an integer ranging from 1 to 75. In yet other embodiments, w is an integer ranging from 1 to 50. In further embodiments, w is an integer ranging from 1 to 20. In even further embodiments, w is an integer ranging from 1 to 10. In yet further embodiments, w is 0.

In some embodiments, L is a halide or —OH. In other embodiments, L is selected from the group consisting of F, Cl, Br and —OH.

As used herein, the terms "cyclopentadiene-based ring" or "cyclopentadiene" (used interchangeably herein) is not limited to cyclopentadiene, but includes derivatives of cyclopentadiene, i.e. those containing substituents other than hydrogen, or those capable of being substituted with A groups as defined in Formulas (IA) or (IB). The terms "cyclopentadiene-based ring" or "cyclopentadiene" are also intended to include fused ring systems comprising, in part, a cyclopentadiene ring, e.g. an indene. By way of example, X may encompasses cyclopentadiene; indene; an indene substituted with one or more $C_1$ to $C_4$ straight-chain or branched alkyl groups; fluorene; and fluorene substituted with one or more $C_1$ to $C_4$ straight-chain or branched alkyl groups. By way of a further example, where it is denoted that X is a cyclopentadiene ring, this may refer to the base structure of X and, as will appreciated by those of ordinary skill in the art, any of the "implicit" hydrogens of the cyclopentadiene ring may be substituted with any number of A groups, as denoted in Formulas (IA) or (IB).

In some embodiments, each —$X(A)_r(Z)_n$— group may be the same or different. Likewise, each —$X(A)_r(Z)_n$— group may be the same or different. In some embodiments, the compounds of Formula (IA) or (IB) comprise different —$X(A)_r(Z)_u$— groups or different —$X(A)_m(Z)_n$— groups, where each —$X(A)_r(Z)_n$— group or —$X(A)_m(Z)_n$— group is provided randomly, in blocks, or in random blocks.

For example, the compounds of Formulas (IA) or (IB) may comprise two different —$X(A)_r(Z)_n$— groups, wherein at least one of the —X(A)r(Z)n- groups comprises a different (A) moiety. By way of a further example, the compounds of Formulas (IA) or (IB) may comprise a first —$X(A)_r(Z)_n$— group substituted with a vinyl benzyl group, and a second —$X(A)_r(Z)_n$— group substituted with an allyl group, where each of the first and second —$X(A)_r(Z)_n$— groups may be distributed randomly, in blocks, or in random blocks.

By way of yet another example, the compounds of Formulas (IA) or (IB) having different —$X(A)_r(Z)_n$— groups may have the structure provided by Formula (IC):

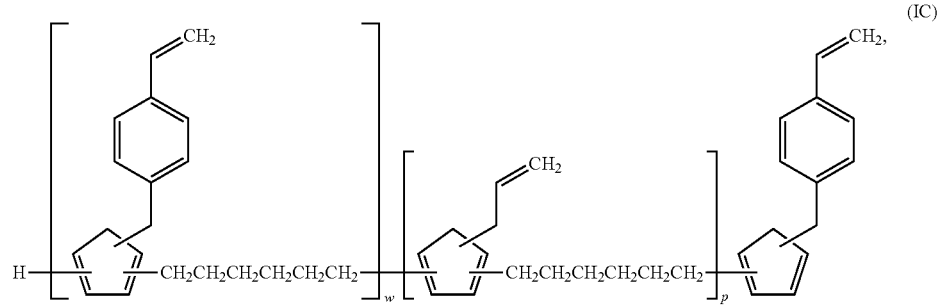

where w and p are each independently an integer ranging from 1 to 150.

In some embodiments, the resins of Formulas (IA) or (IB) may have two, three or more different —X(A)$_m$(Z)$_n$— groups or two, three, or more different —X(A)$_r$(Z)$_n$— groups, which may be provided randomly within the resin. In addition, while the skilled artisan will appreciate that any two or more different —X(A)$_m$(Z)$_n$-groups or —X(A)$_r$(Z)$_n$— groups may differ in the (A) moiety included, the different —X(A)$_m$(Z)$_n$— groups or —X(A)$_r$(Z)$_n$— groups may instead differ by virtue of the (Z) group included, or any combination of (A) and/or (Z) groups.

In some embodiments, A has the structure defined by Formula (IIA):

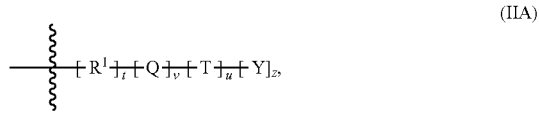

wherein R$^1$ is a bond, or a saturated or unsaturated straight-chain or branched, linear or cyclic, substituted or unsubstituted, aliphatic or aromatic group having from about 1 to about 10 carbon atoms, Q is a bond or a linking group optionally comprising a heteroatom;

T is a bond or —CH$_2$—, -phenyl, or —CH$_2$-phenyl;

Y is H, —CH$_3$, —CH═CH$_2$, —CH═CH—CH$_3$, or an alkyne group;

t and v are independently 0 or an integer ranging from 1 to 20;

u is 0 or 1; and z is an integer ranging from 1 to 5.

In some embodiments, when T is -phenyl, or —CH$_2$-phenyl, and Y is —CH═CH$_2$, —CH═CH—CH$_3$, or an alkyne group, z is 1.

In some embodiments, R$^1$ is —CH$_2$—. In other embodiments, R$^1$ is —C(CH$_3$)$_2$—.

In some embodiments, A has the structure defined by Formula (IIB):

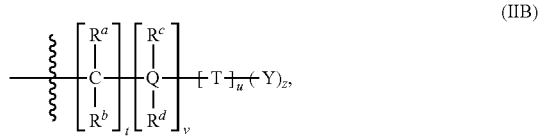

wherein
Q is C, O, N, or S;
R$^a$, R$^b$, R$^c$, R$^d$ are independently selected from H, F, a C$_1$ to C$_{10}$ linear or cyclic, saturated or unsaturated, branched or straight chain aromatic or aliphatic group;
T is —CH$_2$—, -phenyl, or —CH$_2$-phenyl;
Y is H, —CH$_3$, —CH═CH$_2$, —CH═CH—CH$_3$, or an alkyne group;
t and v are independently 0 or an integer ranging from 1 to 20;
u is 0 or 1; and
z is an integer ranging from 1 to 5.

In some embodiments, wherein when T is -phenyl, or —CH$_2$-phenyl, and Y is —CH═CH$_2$, —CH═CH—CH$_3$, or an alkyne group, z is 1.

In some embodiments of the moieties of Formula (IIB), v is 0 or 1.

In some embodiments, at least one of t or v is at least 1. In some embodiments, at least one of t or v is 1, u is 1, and Y is selected from the group consisting of —CH═CH$_2$, —CH═CH—CH$_3$, or an alkyne group. In some embodiments, at least one of t is 1, u is 0, v is 0, and Y is selected from the group consisting of —CH═CH$_2$, —CH═CH—CH$_3$, or an alkyne group.

In other embodiments, t, u, and v are each 0, and Y is selected from the group consisting of —CH═CH$_2$, —CH═CH—CH$_3$, or an alkyne group.

In some embodiments, R$^a$, R$^b$, R$^c$, R$^d$ are independently selected from H, F, a C$_1$ to C$_6$ straight chain or branched alkyl group; a cyclopentadiene, —CH$_2$-cyclopentadiene, or —CH$_2$—CH$_2$-cyclopentadiene.

In some embodiments, Q is C, R$^a$ and R$^b$ are —CH$_3$, R$^c$ and R$^d$ are H, u is 0, and Y is —CH$_3$. In other embodiments, Q is C, R$^a$ and R$^b$ are —CH$_3$, R$^c$ and R$^d$ are H, u is 0, Y is —CH$_3$, and t is an integer ranging from 1 to 6.

In some embodiments, Q is C, R$^a$ and R$^b$ are H, one of R$^c$ and R$^d$ is —CH$_2$—CH$_3$ or —CH$_3$, the other of R$^c$ and R$^d$ is —CH$_2$—CH$_2$—CH$_2$—CH$_3$ or —CH$_2$—CH$_2$—CH$_2$—CH$_2$—CH$_3$, u is 0, and Y is H. In other embodiments, Q is C, R$^a$ and R$^b$ are H, one of R$^c$ and R$^d$ is —CH$_2$—CH$_3$ or —CH$_3$, the other of R$^c$ and R$^d$ is —CH$_2$—CH$_2$—CH$_2$—CH$_3$ or —CH$_2$—CH$_2$—CH$_2$—CH$_2$—CH$_3$, u is 0, Y is H, and t is an integer ranging from 1 to 6.

In some embodiments, Q is C, R$^a$ and R$^b$ are H, one of R$^c$ and R$^d$ is —CH$_2$—CH$_3$ or —CH$_3$, the other of R$^c$ and R$^d$ is —CH$_2$—CH$_2$—CH$_2$—CH$_3$ or —CH$_2$—CH$_2$—CH$_2$—CH$_2$—CH$_3$, u is 0, and Y is —CH$_3$. In other embodiments, Q is C, R$^a$ and R$^b$ are H, one of R$^c$ and R$^d$ is —CH$_2$—CH$_3$ or —CH$_3$, the other of R$^c$ and R$^d$ is —CH$_2$—CH$_2$—CH$_2$—CH$_3$ or —CH$_2$—CH$_2$—CH$_2$—CH$_2$—CH$_3$, u is 0, Y is —CH$_3$, and t is an integer ranging from 1 to 6.

In some embodiments, Q is C, R$^a$ and R$^b$ are H, R$^c$ and R$^d$ are both —CH$_3$, u is 0, and Y is H. In some embodiments, Q is C, R$^a$ and R$^b$ are H, R$^c$ and R$^d$ are both —CH$_3$, u is 0, Y is H, and t is an integer ranging from 1 to 6. In other embodiments, Q is C, R$^a$ and R$^b$ are H, R$^c$ and R$^d$ are both —CH$_3$, u is 0, and Y is —CH$_3$. In other embodiments, Q is C, R$^a$ and R$^b$ are H, R$^c$ and R$^d$ are both —CH$_3$, u is 0, Y is —CH$_3$, and t is an integer ranging from 1 to 6.

In some embodiments, Q is C, R$^a$ and R$^b$ are H, R$^c$ and R$^d$ are independently selected from a cyclopentadiene or —CH$_2$-cyclopentadiene, u is 0, v is 1, and Y is CH$_3$. In other embodiments, Q is C, R$^a$ and R$^b$ are H, R$^c$ and R$^d$ are independently selected from a cyclopentadiene or —CH$_2$-cyclopentadiene, u is 0, v is 1, and Y is H.

In some embodiments, A has the structure defined by Formula (IIC):

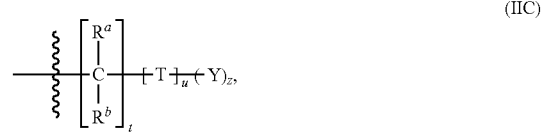

wherein
R$^a$ and R$^b$ are independently selected from H, F, a C$_1$ to C$_{10}$ linear or cyclic, branched or straight chain aliphatic group;

T is —CH$_2$—, -phenyl, or —CH$_2$-phenyl;

Y is H, —CH$_3$, —CH=CH$_2$, —CH=CH—CH$_3$, or alkyne;

t is 0 or an integer ranging from 1 to 20;

u is 0 or 1; and z is an integer ranging from 1 to 5.

In some embodiments, when T is -phenyl, or —CH$_2$-phenyl, and Y is —CH=CH$_2$, —CH=CH—CH$_3$, or alkyne, z is 1.

In some embodiments, the R$^a$ and R$^b$ are independently a C$_1$ to C$_6$ linear or cyclic, branched or straight chain aliphatic group. In some embodiments, the R$^a$ and R$^b$ are independently a C$_1$ to C$_6$ alkyl group. In some embodiments, the R$^a$ and R$^b$ are independently a C$_1$ to C$_4$ alkyl group.

In some embodiments, t is 1, u is 1, and Y is —CH=CH$_2$. In other embodiments, t is 0, u is 1, and Y is —CH=CH$_2$. In yet other embodiments, t ranges from 1 to 10, R$^a$ and R$^b$ are independently H, —CH$_2$—CH$_3$, —CH(CH$_3$)—CH$_3$ or —CH$_3$ and u is 0. In further embodiments, t ranges from 1 to 10, R$^a$ and R$^b$ are independently H, —CH$_2$—CH$_3$, —CH(CH$_3$)—CH$_3$ or —CH$_3$ and u is 1. In yet further embodiments, t is 0, u is 1, and Y is —CH=CH—CH$_3$. In yet further embodiments, t is 0, u is 1, and Y is alkyne. In even other embodiments, u is 1 and T is phenyl. In yet even further embodiments, t is 1, u is 1, T is phenyl, and R$^a$ and R$^b$ are both H.

In some embodiments, A has the structure defined by Formula (IID):

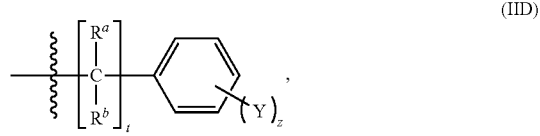

(IID)

wherein

R$^a$ and R$^b$ are independently selected from H, F, a C$_1$ to C$_{10}$ linear or cyclic, branched or straight chain aliphatic group; Y is H, —CH$_3$, —CH=CH$_2$, —CH=CH—CH$_3$, or alkyne; and t is 0 or an integer ranging from 1 to 20; z is an integer ranging from 1 to about 5. In some embodiments, when Y is —CH=CH$_2$, —CH=CH—CH$_3$, or alkyne, z is 1. In some embodiments, the R$^a$ and R$^b$ are independently a C$_1$ to C$_6$ linear or cyclic, branched or straight chain aliphatic group. In some embodiments, z is 1 or 2. In other embodiments, z is 1.

In some embodiments, the R$^a$ and R$^b$ are independently a C$_1$ to C$_6$ alkyl group. In some embodiments, the R$^a$ and R$^b$ are independently a C$_1$ to C$_4$ alkyl group.

The skilled artisan will appreciate that the group Y may be present at any position(s) along the phenyl ring. Of course, any resin of Formulas (IA) or (IB) may comprise different Y groups. Likewise, any resin of Formulas (IA) or (IB) may comprise the same Y group, but the Y group may be located at different positions along the phenyl ring. In addition, some A groups may comprise a single Y group while other A groups may contain multiple Y groups, which may be the same or different or differ in their positioning.

In some embodiments, t is an integer ranging from 1 to 6, R$^a$ and R$^b$ are both H, and Y is —CH=CH$_2$. In other embodiments, t is 1 or 2, R$^a$ and R$^b$ are both H, and Y is —CH=CH$_2$. In yet other embodiments, t is an integer ranging from 1 to 6, R$^a$ and R$^b$ are both H, and Y is —CH=CH$_2$. In other embodiments, t is 1 or 2, R$^a$ and R$^b$ are both H, and Y is —CH=CH$_2$. In yet further embodiments, t is 1 or 2, R$^a$ and R$^b$ are both —CH$_3$, and Y is —CH=CH$_2$.

In some embodiments, Z has the structure defined by Formula (IIIA):

(IIIA)

wherein

R$^e$ and R$^f$ are independently selected from H, F, or a straight chain or branched alkyl group having between 1 and 6 carbon atoms; and y is an integer ranging from between 1 and about 20.

In some embodiments, R$^e$ and R$^f$ are independently selected from H or a straight chain or branched alkyl group having between 1 and 4 carbon atoms; and y is an integer ranging from between 1 and about 10. In other embodiments, R$^e$ and R$^f$ are independently selected from H or a straight chain alkyl group having between 1 and 4 carbon atoms; and y is an integer ranging from between 1 and about 6.

In yet other embodiments, R$^e$ and R$^f$ are both H; and y is an integer ranging from between 1 and about 10. In further embodiments, R$^e$ and R$^f$ are both H; and y is an integer ranging from between 1 and about 6. In even further embodiments, R$^e$ and R$^f$ are both H; and y is an integer ranging from between 2 and about 6. In yet even further embodiments, R$^e$ and R$^f$ are both H; and y is an integer ranging from between 3 and about 6. In even further embodiments, R$^e$ and R$^f$ are both H; and y is 3. In even further embodiments, R$^e$ and R$^f$ are both H; and y is 6.

In some embodiments, R$^e$ and R$^f$ are independently selected from H, —CH$_2$—CH$_3$, or —CH$_3$. In other embodiments, one of R$^e$ and R$^f$ is selected from H or —CH$_3$, and the other of R$^e$ and R$^f$ is H. In yet other embodiments, R$^e$ and R$^f$ are both H.

In some embodiments, Z has the structure defined by Formula (IIIB):

(IIIB)

where y is an integer ranging from between 1 and about 20. In some embodiments of the moieties of Formula y ranges from 1 to 6. In some embodiments of the moieties of Formula (IIIB), y ranges from 1 to 4. In some embodiments of the moieties of Formula (IIIB), y ranges from 1 to 3. In some embodiments of the moieties of Formula (IIIB), y ranges from 2 to 6. In some embodiments of the moieties of Formula (IIIB), y ranges from 2 to 4.

In some embodiments, Z has the structure defined by Formula (IIIC):

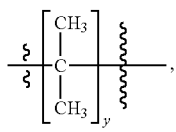
(IIIC)

where y is as defined above. In some embodiments of the moieties of Formula (IIIC), y ranges from 1 to 6. In some embodiments of the moieties of Formula (IIIC), y ranges from 1 to 4. In some embodiments of the moieties of Formula (IIIC), y ranges from 1 to 3. In some embodiments of the moieties of Formula (IIIC), y ranges from 2 to 6. In some embodiments of the moieties of Formula (IIIC), y ranges from 2 to 4.

In some embodiments, the compounds of Formula (IA) or (IB) have the structure defined by Formulas (IVA), (IVB), or (IVC):

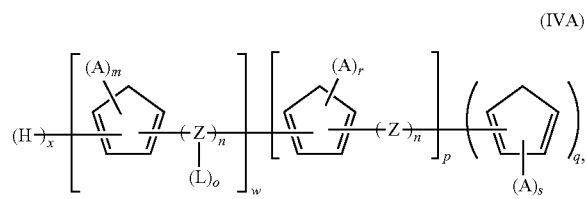
(IVA)

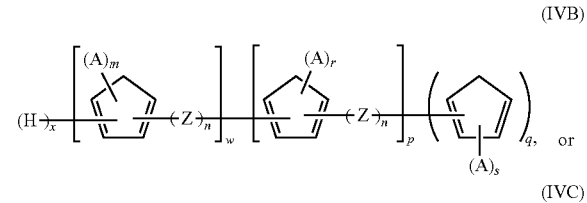
(IVB)

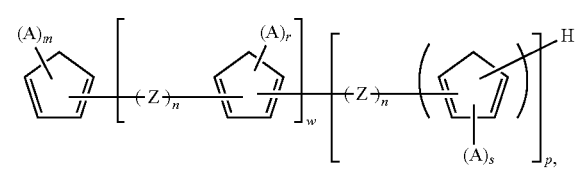
(IVC)

wherein
L is a leaving group;
each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;
Z is a bond or straight-chain or branched, substituted or unsubstituted, aliphatic group having between 1 and 20 carbon atoms;
m is an integer ranging from 1 to 5;
n is 0 or 1;
o is 0 or 1;
p is 0 or an integer ranging from 1 to 150;
q is 0 or 1;
r is an integer ranging from 1 to 4;
w is 0 or an integer ranging from 1 to 150; and
x is 0 or 1.

The skilled artisan will appreciate that the A groups, i.e. $(A)_m$, $(A)_r$ or $(A)_s$, may be in any position along any of the cyclopentadiene-based group. The skilled artisan will also appreciate that when more than one A group is present along any of the cyclopentadiene-based rings, that the A groups may be located on the same or different positions in each cyclopentadiene-based based group. For example, one

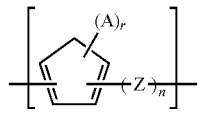

group may comprise an A group at a first ring position (e.g. one carbon away from the carbon bearing the $Z_n$ group) while another

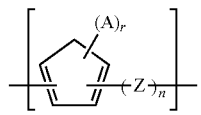

group may comprise an A group at a second or third ring position (e.g. two or three carbons away from the carbon bearing the $Z_n$ group). Likewise, and again by way of example, one

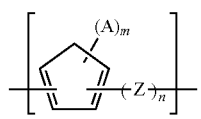

group may comprise an A group at a first ring position (e.g. one carbon away from the carbon bearing the $Z_n$ group) while another

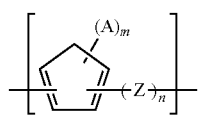

group may comprise an A group at a second or third ring position (e.g. two or three carbons away from the carbon bearing the $Z_n$ group).

In some embodiments of the compounds of Formula (IVA), (IVB), or (IVC), m, p, q, and x are 0; $(Z)_n$ is a straight-chain or branched aliphatic group having between 1 and 20 carbon atoms; o is 1; and L is a leaving group. In other embodiments, m, p, q, and x are 0; $(Z)_n$ is a straight-chain or branched aliphatic group having between 1 and 10 carbon atoms, o is 1, and L is a leaving group. In yet other embodiments, m, p, q, and x are 0; $(Z)_n$ is a straight-chain or branched aliphatic group having between 1 and 6 carbon atoms, o is 1, and L is a leaving group. In further embodiments, m, p, q, and x are 0; $(Z)_n$ is a straight-chain alkyl group having between 1 and 6 carbon atoms, o is 1, and L is a leaving group. In further embodiments, m, p, q, and x are 0; $(Z)_n$ is a straight-chain alkyl group having between 1 and 4 carbon atoms, o is 1, and L is a leaving group. In some embodiment of the compounds of Formula (IVA), (IVB), or (IVC), m, p, q, and x are 0; Z is an aliphatic group having between 1 and 6 carbon atoms; and L is a halide or —OH group.

In some embodiments of the compounds of Formula (IVA), (IVB), or (IVC), n, q, and w are 1; o is 0, x is 1; A comprises a moiety which terminates in a group selected from —CH=CH$_2$, —CH=CH—CH$_3$ or alkyne; and Z comprises an aliphatic group having at least three carbon atoms. In other embodiments of the compounds of Formula (IVA), (IVB), or (IVC), n, q, and w are 1; o is 0, x is 1; A comprises a moiety which terminates in a group selected from H or —CH$_3$; and Z comprises an aliphatic group having at least three carbon atoms. In other embodiments of the compounds of Formula (IVA), (IVB), or (IVC), n, q, and w are 1; o is 0, x is 1; A comprises a moiety which terminates in an alkyne group; and Z comprises an aliphatic group having at least three carbon atoms.

In some embodiments of the compounds of Formula (IVA), (IVB), or (IVC), n, q, and w are 1; o is 0, x is 1; A comprises a moiety which terminates in hydrogen or a group selected from —CH=CH$_2$, —CH=CH—CH$_3$ or alkyne; and wherein the compounds of Formula (IVA), (IVB), or (IVC), comprise at least two different

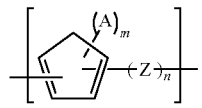

groups.

In some embodiments of the compounds of Formula (IVA), (IVB), or (IVC), n, q, and w are 1; o is 0, x is 1; and where the compounds of Formula (IV) comprise at least two different

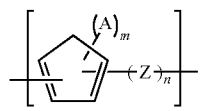

groups, wherein a first subset of

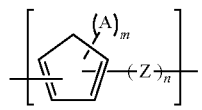

groups comprise vinyl styrene moieties, and wherein a second subset of

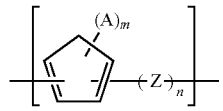

groups comprise allyl moieties.

Likewise, in other embodiments of the compounds of Formula (IVA), (IVB), or (IVC), n, q, and w are 1; o is 0, x is 1; A comprises a moiety which terminates in hydrogen or a group selected from —CH=CH$_2$, —CH=CH—CH$_3$ or alkyne; and wherein the compounds of Formula (IVA), (IVB), or (IVC), comprise at least two different

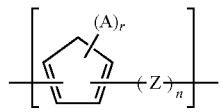

groups.

In some embodiments of the compounds of Formula (IVA), (IVB), or (IVC), n, q, and w are 1; o is 0, x is 1; and where the compounds of Formula (IV) comprise at least two different

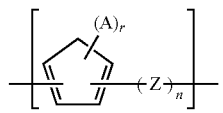

groups, wherein a first subset of

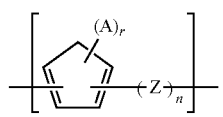

groups comprise vinyl styrene moieties, and wherein a second subset of

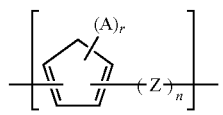

groups comprise allyl moieties.

In some embodiments, the compounds of Formula (IA) or (IB) have the structure defined by Formulas (VA) or (VB):

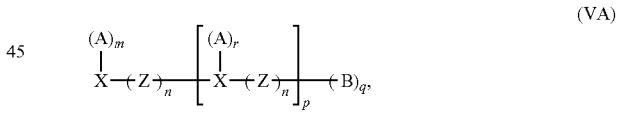
(VA)

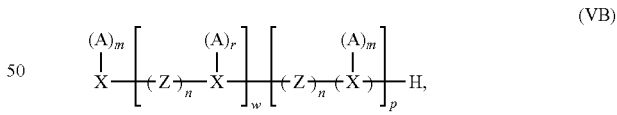
(VB)

wherein
X is a moiety comprising a cyclopentadiene-based ring;
B is H or X(A)$_s$;
each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;
Z is a bond or straight-chain or branched, substituted or unsubstituted, aliphatic group having between 1 and 20 carbon atoms;
m is an integer ranging from 1 to 5;
n is 0 or 1;
p is 0 or an integer ranging from 1 to 150;

q is 0 or 1;
r is an integer ranging from 1 to 4;
s is an integer ranging from 1 to 5; and
w is 0 or an integer ranging from 1 to 150.

In some embodiments of the compounds of Formula (VA) or (VB), p is an integer ranging from between 1 and 20, and B is X(A)$_s$. In some embodiments, p is an integer ranging from between 1 and 20, A is hydrogen, and X is cyclopentadiene or derived from cyclopentadiene. In some embodiments, p is an integer ranging from between 1 and 20, A is hydrogen, X is cyclopentadiene or derived from cyclopentadiene, and (Z)$_n$ is a straight-chain or branched aliphatic group having between 1 and 6 carbon atoms. In some embodiments, p is an integer ranging from between 1 and 20, X is cyclopentadiene substituted with one (A) moiety that is other than hydrogen, and B is X(A)$_1$. In some embodiments, p is an integer ranging from between 1 and 20, X is cyclopentadiene substituted with one (A) moiety that is other than hydrogen, B is X(A)$_1$, and (Z)$_n$ is a straight-chain or branched aliphatic group having between 1 and 6 carbon atoms.

In some embodiments, the compounds of Formula (IA) or (IB) have the structure defined by Formula (VI):

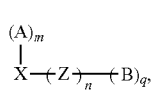

(VI)

wherein
X is a moiety comprising a cyclopentadiene-based ring;
B is H or X(A)$_s$;
each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;
Z is a bond or straight-chain or branched, substituted or unsubstituted, aliphatic group having between 1 and 20 carbon atoms;
m is an integer ranging from 1 to 5;
n is 0 or 1;
q is 0 or 1; and
s is an integer ranging from 1 to 5.

In some embodiments of the compounds of Formula (VI), (Z)$_n$ is a bond. In some embodiments of the compounds of Formula (VI), m is 2 and where each A group is different. In some embodiments, m is 2 and a first A group comprises a vinyl benzyl group and a second A group is —CH$_2$—CH=CH$_2$.

In some embodiments, X is cyclopentadiene, B is H; (Z)$_n$ is a bond; m is ranges from 1 to 5; and A is as defined herein. In some embodiments, A is a moiety having the structure defined by Formula (IID).

In some embodiments, A is hydrogen, and X and B are both cyclopentadiene or derived from cyclopentadiene. In other embodiments, A is hydrogen, X and B are both cyclopentadiene or derived from cyclopentadiene, and (Z)$_n$ is a straight-chain or branched aliphatic group having between 1 and 6 carbon atoms. In yet other embodiments, X is cyclopentadiene substituted with one (A) moiety that is other than hydrogen, and B is X(A)$_1$. In further embodiments, X is cyclopentadiene substituted with one (A) moiety that is other than hydrogen, B is X(A)$_1$, and (Z)$_n$ is a straight-chain or branched aliphatic group having between 1 and 6 carbon atoms.

In some embodiments, n and q are both 0. In some embodiments, n and q are both 0, and m is 1. In some embodiments, n and q are both 0, and m is 2. In some embodiments, n and q are both 0, and A terminates in a moiety selected from the group consisting a —CH=CH$_2$ group, a —CH=CH—CH$_3$ group, and an alkyne group. In some embodiments, n and q are both 0, and A terminates in a moiety selected from the group consisting a —CH=CH$_2$ group, a —CH=CH—CH$_3$ group, and an alkyne group, and m is 1. In some embodiments, n and q are both 0, and A terminates in a moiety selected from the group consisting a —CH=CH$_2$ group, a —CH=CH—CH$_3$ group, and an alkyne group, and m is an integer ranging from 1 to 3. In some embodiments, n and q are both 0, and A terminates in a moiety selected from the group consisting a —CH=CH$_2$ group, a —CH=CH—CH$_3$ group, and an alkyne group, and m is an integer ranging from 2 to 4. In some embodiments, n and q are both 0, and A terminates in a moiety selected from the group consisting a —CH=CH$_2$ group, a —CH=CH—CH$_3$ group, and an alkyne group, and m is 2.

In some embodiments, the compounds of Formula (VI) have the structure defined by Formula (VII):

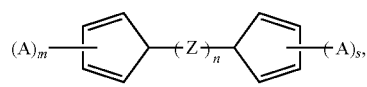

(VII)

wherein each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;
Z is a bond or straight-chain or branched, substituted or unsubstituted, aliphatic group having between 1 and 20 carbon atoms;
m is an integer ranging from 1 to 5;
n is 0 or 1;
q is 0 or 1; and
s is an integer ranging from 1 to 5.

In some embodiments, the compounds of Formula (IVA) have the structure defined by Formula (VIII):

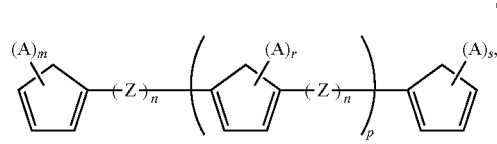

(VIII)

wherein
each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;
Z is a bond or straight-chain or branched, substituted or unsubstituted, aliphatic group having between 1 and 20 carbon atoms;
m is an integer ranging from 1 to 5;
n is 0 or 1;
p is 0 or an integer ranging from 1 to 150;
r is an integer ranging from 1 to 4; and
s is an integer ranging from 1 to 5.

Specific non-limiting examples of the compounds of Formulas (IA) or (IB) are set forth below, each of which may be (i) blended with another polymer, copolymer, or filler material; (ii) crosslinked with a crosslinking agent; (iii) polymerized to form homopolymers, copolymers, or interpenetrating polymer networks; and/or (iv) reacted with a dienophile (as disclosed further herein). In some embodiments, each of the non-limiting examples of resins set forth below have a dielectric value (Dk) of the resin ranges from about 1.5 to about 3. In some embodiments, each of the non-limiting examples of resins set forth below have a dissipation value (Df) of the resin ranges from about 0.0001 to about 0.004. In some embodiments, each of the non-limiting examples of resins set forth below have a glass transition temperature (Tg) of greater than 100° C. In some embodiments, each of the non-limiting examples of resins set forth below have a glass transition temperature (Tg) of at least 150° C. Of course, each of the non-limiting resins recited below may be included within a kit and/or may be supplied in a suitable solvent.

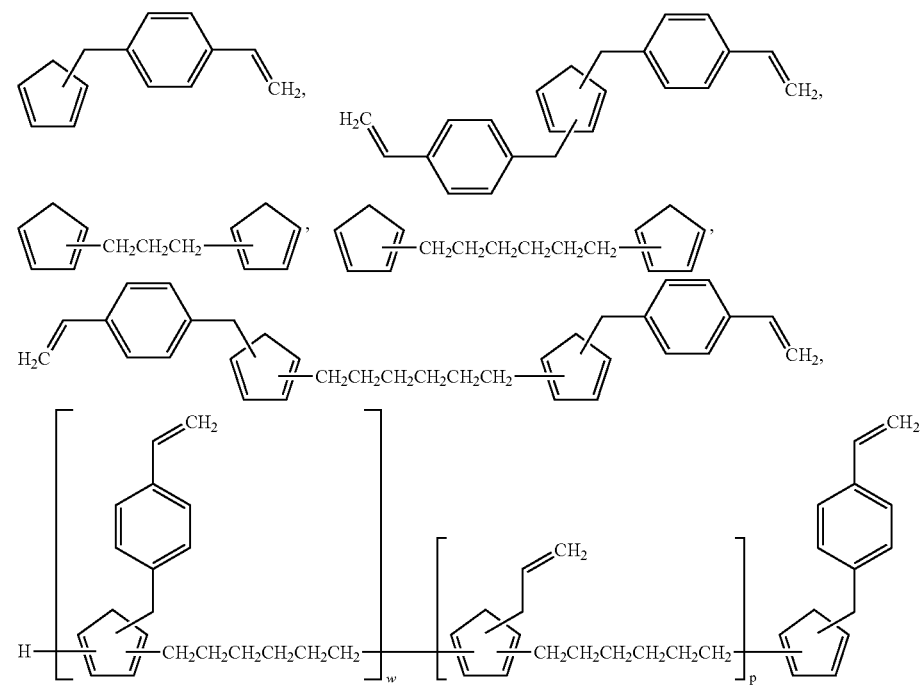

where w and p are independently an integer ranging from 1 to 150,

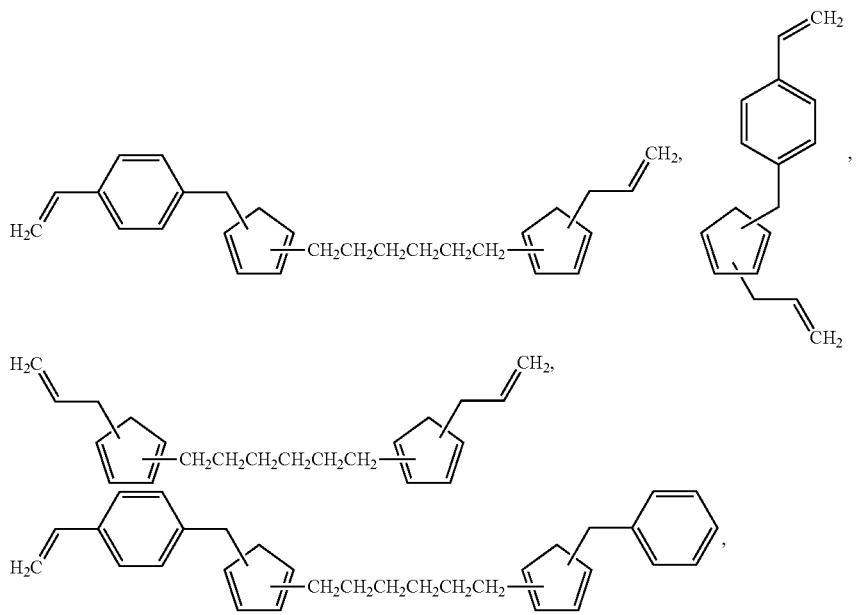

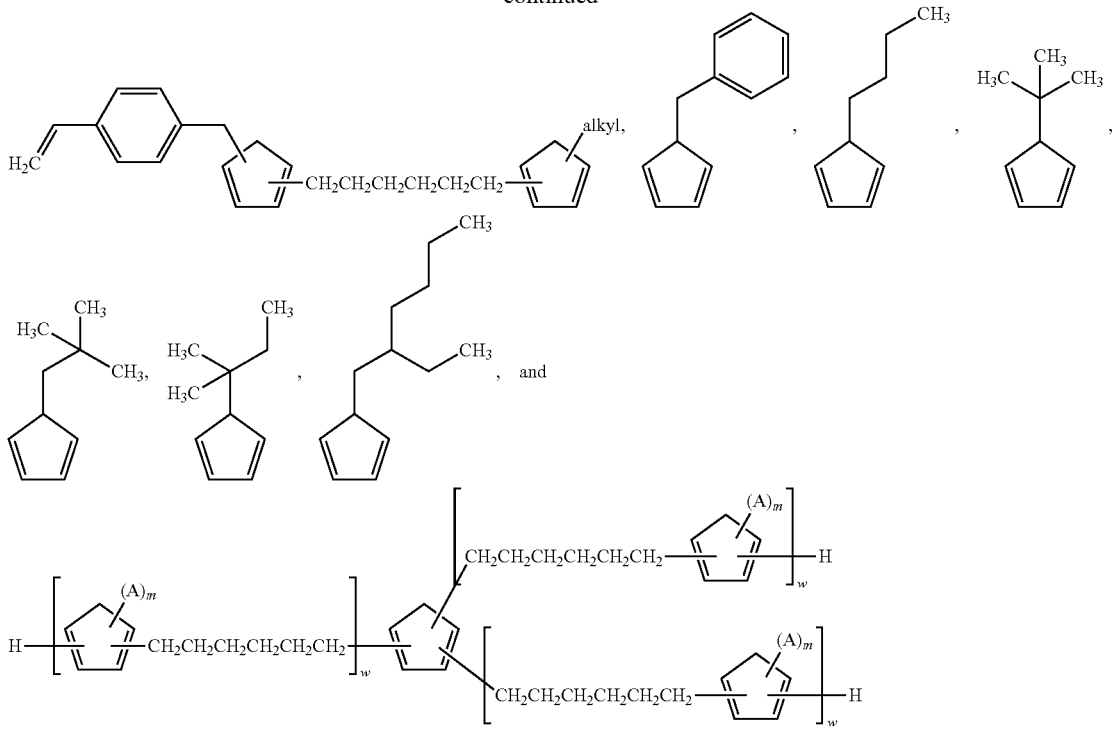

where w and p are each independently an integer ranging from 1 to 150.

General Synthetic Methods for Preparing the Compounds of Formulas (IA) and (IB)

In some embodiments, cyclopentadiene, a cyclopentadiene derivative, a moiety comprising a cyclopentadiene group, or a moiety comprising a cyclopentadiene derivative is provided as a starting material which, in the presence of a base (e.g. NaH), may be converted to the respective anion. Suitable bases may also include hydroxides and alkoxides, if suitable reaction conditions, catalysts, and equipment (such as in a phase-transfer process) are used in such a way as to allow for formation of the cyclopentadiene anion.

In some embodiments, the resins of Formulas (IA) or IB may be synthesized from the starting materials of any of Formulas (IXA), (IXB), or (IXC):

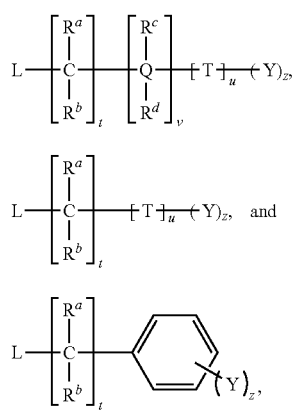

wherein $R^a$ and $R^b$ are independently selected from H, F, a $C_1$ to $C_{10}$ linear or cyclic, saturated or unsaturated, branched or straight chain aromatic or aliphatic group; T is $-CH_2-$, -phenyl, or $-CH_2$-phenyl; Y is H, $-CH_3$, $-CH=CH_2$, $-CH=CH-CH_3$, or an alkyne group; t is an integer ranging from 1 to 20; u is 0 or 1; and L is a leaving group.

In some embodiments, a cyclopentadiene anion is generated by combination of a compound including a cyclopentadiene group with an excess of a strong base, e.g. sodium hydride, in a suitable solvent (e.g. THF) at moderate temperatures (typically between about 0° C. and about 100° C.). This cyclopentadiene anion solution can then be combined with desired molar equivalents of one or more starting materials of Formulas (IXA), (IXB), (IXC), (XA), (XB), and (XC) and allowed to react at moderate temperature for about 30 minutes or until satisfactory conversion to product is achieved. Unreacted base can be neutralized or diluted by addition of water, alcohol or acidic aqueous solution. Crude product mixtures may be isolated by in vacuo removal of reaction solvent. Higher purity product mixtures may be achieved through combinations of dilution in hydrocarbon solvents, filtration of insoluble reaction byproducts, washings with neutral or acidic aqueous solutions to remove reaction byproducts, and removal of solvent in vacuo to produce high yields of resins of Formulas (IA) or (IB). In other embodiments, a combination of a compound including a cyclopentadiene; the desired molar equivalents of one or more starting materials of Formulas (IXA), (IXB), (IXC), (XA), (XB), and (XC); and a tetra-alkyl ammonium chloride phase-transfer catalyst are mixed with a strong aqueous base solution (such as about 50 weight % potassium hydroxide in water), and stirred vigorously until product formation is complete. This biphasic reaction mixture generates cyclopentadiene anion in the presence of the reactive starting materials, yielding desired product. Product may be isolated by separation of the organic layer, followed by washings with neutral or acidic aqueous solutions to remove reaction byproducts and catalyst to give high yields of resin of Formula (IA) or (IB).

For example, a compound including a cyclopentadiene group (e.g. such as those defined herein as "X") may first be treated with a base and subsequently reacted with a compound of any of Formulas (IXA), (IXB), or (IXC) to provide a resin of Formulas (IA) or (IB).

A compound including a cyclopentadiene group may first be treated with a base and subsequently reacted with a compound of any of Formulas (XA), (XB), and (XC) to provide a resin of Formula (IA) or (IB):

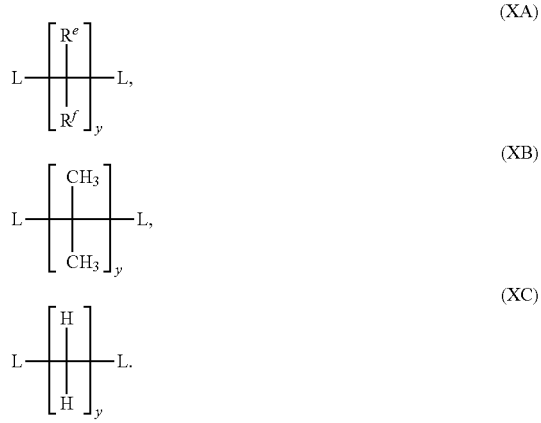

The starting materials of Formulas (IXA), (IXB), (IXC), (XA), (XB), and (XC) and cyclopentadiene or a derivative thereof may be combined in any order to generate a thermosetting resin formulation meeting desired characteristics. Preparation of the anion of cyclopentadiene or a derivative thereof can be completed before reaction with a compound of any of Formulas (IXA), (IXB), (IXC), (XA), (XB), and (XC) and any additional reactive compounds. Alternatively, the anion of cyclopentadiene or a derivative thereof can be generated in the presence of a compound of any of Formulas (IXA), (IXB), (IXC), (XA), (XB), and (XC) and any additional reactive compounds such that the anion reacts quickly after formation.

Furthermore, after reaction of an anion of a cyclopentadiene or a derivative thereof and a compound of any of Formulas (IXA), (IXB), (IXC), (XA), (XB), and (XC) an initial reaction product is formed having Formula (IA) or (IB). If sufficient strong base remains available the generated resin of Formulas (IA) or (IB) serving as an intermediate, may become further deprotonated, regenerating a stable anion capable of further reaction with additional compounds of any of Formulas (IXA), (IXB), (IXC), (XA), (XB), and (XC) to form yet a different product having any of Formula (IA) or (IB). This process can repeat multiple times. Likewise, reaction components can be combined in various ways to affect the overall product distribution, as understood by those skilled in the art. If desired, one or more of the reactive components of the disclosure can be formed in situ during the reaction process.

The viscosity of the thermosetting resin formulation can be tuned as desired by moderation of the molar ratios of the reactive components and molar equivalents of base. Increasing the base-to-cyclopentadiene or a derivative thereof molar ratio promotes multiple reactions between the cyclopentadiene or a derivative thereof and other reactive components, when the specific structure of the cyclopentadiene or a derivative thereof is capable of more than one formation of the reactive anion and the viscosity of the product composition typically increases with an increase in the average number of reactions per cyclopentadiene or a derivative thereof. Reaction of a cyclopentadiene or a derivative thereof with a compound of any of Formulas (IXA), (IXB), (IXC), (XA), (XB), and (XC) in molar ratios that favor formation of smaller molecules lead to product compositions with lower viscosity, whereas higher-viscosity oligomeric compound distributions can be favored by usage of a compound of any of Formulas (IXA), (IXB), (IXC), (XA), (XB), and (XC) possessing more than one reactive leaving group per molecule. In some embodiments, about 1 equivalent of a cyclopentadiene or a derivative thereof is reacted with 2 or more equivalents of a compound of any of Formulas (IXA), (IXB), (IXC), (XA), (XB), and (XC) in the presence of 2 or more equivalents of strong base to form a product composition featuring 2 or more moieties capable of carbon-carbon bond forming reactions per cyclopentadiene or a derivative unit.

Reaction compounds may be combined at any temperature suitable to effect formation of an appropriate resin formulation. Reaction of cyclopentadiene or a derivative thereof with strong base is typically performed at temperatures from about −70° C. to about 200° C., with optimal reaction temperatures depending heavily on properties of solvent and equipment used in the chemistry. In some embodiments, the reaction is conducted at temperatures between about 20° C. to about 100° C.

The reaction may be conducted in any suitable solvent, including ethers (tetrahydrofuran, diglyme) and hydrocarbon solvents (xylene, toluene). The reaction may also be conducted in the absence of solvent, if reaction components are sufficiently miscible to generate desired products. Reactions may be conducted in biphasic systems of aqueous base and organic reactants, with and without additional organic solvents, and with or without added phase-transfer catalysts such as tetra-substituted ammonium salts. Product mixtures may be isolated by filtration of solid reaction byproducts (salts), solvent extractions to remove aqueous-soluble material, and removal of solvent by evaporation, distillation, or vacuum distillation.

Resins Formed as Reaction Product between a Compound of Formula (IA) or Formula (IB) and a Dienophile In another aspect of the present disclosure are resins formed as a reaction product between (i) a resin of Formulas (IA) or (IB) containing a diene, and (ii) a dienophile (or a heterodienophile) (i.e. a Diels-Alder reaction product). The term "dienophile" refers to an alkene that is reactive toward a diene to provide a 4+2 cycloaddition product. Dienophiles useful in the present methods and composition include, but are not limited to, carbon-containing dienophiles (e.g. alkenes or alkynes) with reduced electron density due to electronegative or resonance effects of adjacent electron-withdrawing groups—such as substituents containing nitroso, carbonyl, or imido groups. In some embodiments, the dienophile is an alkene such as ethylene, propylene or other straight chain alkene (e.g. an acrylate), or a cyclic alkene (e.g. cyclopentadiene), as described herein.

In some embodiments, the dienophile is a bis-maleimide. The term bis-maleimide as used herein includes mono-, bis-, tris-, tetrakis-, and higher functional maleimides and their mixtures. In some embodiments, bis-maleimide resins may be prepared by the reaction of maleic anhydride or a substituted maleic anhydride such as methylmaleic anhydride, with an aromatic or aliphatic di- or polyamine.

Examples of suitable bis-maleimides include, but are not limited to: 1,6'-bismaleimide-(2,2,4-trimethyl)hexane (CAS 39979-46-9), BMI-3000 (a imide-extended BMI oligomer, available from Designer Molecules Inc.), BMI-689 (bismaleimide of dimer diamine, CAS-No. 682800-79-9), 4,4'-Diphenylmethanebismaleimide (CAS-No. 13676-54-5), Polyphenylmethanebismaleimide (CAS-No. 28630-26-4), N,N'-(4-methyl-m-phenylene)-bismaleimide (CAS-No. 6422-83-9), N,N'-m-phenylenebismaleimide (CAS-No. 3006-93-7), Prepolymer bismaleimide resins (e.g. Hos-Technik Homide 250 available as CAS-No. 26140-67-0), bisphenol A diphenyl ether bismaleimide (CAS-No. 79922-55-7), 3,3'-dimethyl-5,5'-diethyl-4,4'-diphenylmethane bismaleimide, (CAS-No. 105391-33-1), N,N'-[Methylenebis(2,6-diethyl-4,1-phenylene)]bis(maleimide) (CAS-No. 105357-12-8), N,N'-[Methylenebis(2-isopropyl-6-methyl-4,1-phenylene)]bis(maleimide), 1,2-bis(maleimido)ethane (CAS-No. 5132-30-9), 1,4-bis(maleimido)butane (CAS-No. 28537-70-4), and 1,6-bis(maleimido)hexane (CAS-No. 4856-78-5).

In some embodiments, suitable bis-maleimides have the structure depicted by the following examples:

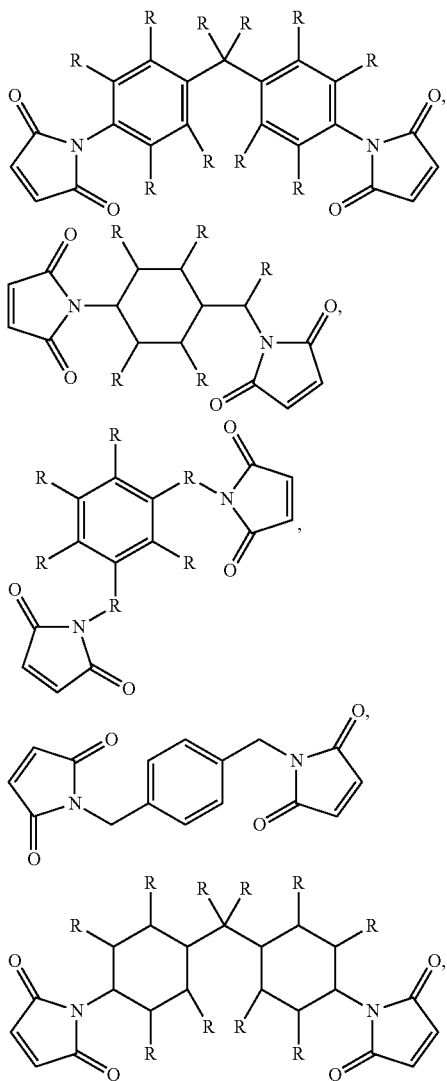

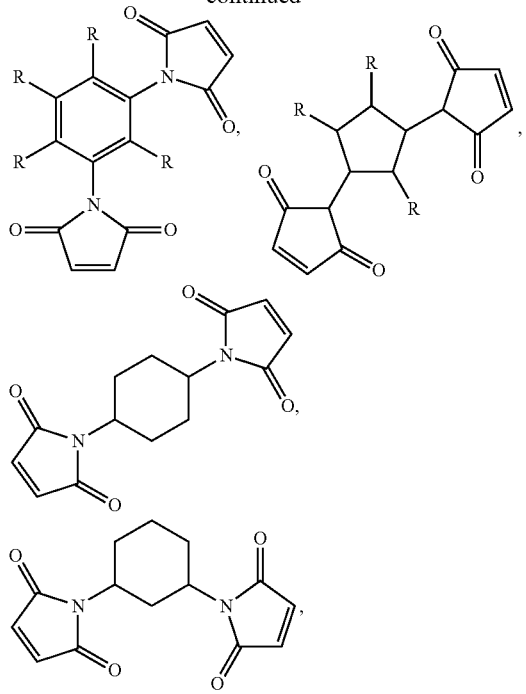

where the R functional groups are independently selected from hydrogen, aromatics, substituted aromatics, aliphatics, substituted aliphatics, cyclo-aliphatics, and substituted cyclo-aliphatics.

Other suitable dienophiles include, but are not limited to, maleic anhydride, derivatives of maleic anhydride, benzoquinone, and derivatives of benzoquinone. Examples of suitable benzoquinone derivatives include 1,4-benzoquinone, 2-methylbenzoquinone, 2,3-dimethylbenzoquinone, 2,5-dimethylbenzoquinone, 2,6-dimethylbenzoquinone, 2,3,5-trimethylbenzoquinone, 2,3,5,6-tetramethylbenzoquinone, and the like and combinations thereof. Examples of suitable maleic derivatives include, but are not limited to, maleic anhydride, methyl maleic anhydride, dimethyl maleic anhydride, maleimide, N-methyl maleimide, N-ethyl maleimide, methyl maleimide, dimethyl maleimide, methyl-N-methyl maleimide, dimethyl-N-methyl maleimide, and the like and combinations thereof.

In some embodiments, the dienophile is a bis-acrylate or an acrylate. In other embodiments, the dienophile is a dialkyl fumarate, a dialkyl maleate, a dialkylacetylenedicarboxylate. In some embodiments, the dienophile is selected from the group consisting of methyl acrylate, ethyl acrylate, methyl methacrylate, ethyl methacrylate, vinyl acrylate, dimethyl fumarate, dimethyl maleate, diethyl fumarate, diethyl maleate, diphenyl fumarate, divinyl fumarate, divinylmaleate, acrolein, methyl vinyl ketone, divinylketone, acrylamide, N,N-dimethyl acrylamide, N,N-dimethyl methacrylamide, N,N-diethyl acrylamide, N,N-diethyl acrylamide, acrylonitrile, methacrylonitrile, 1,1-dicyanoethylene, maleonitrile, fumaronitrile, and tetracyanoethylene. Other acrylates include hexane diol diacrylate and other $C_4$-$C_{10}$ alkane diacrylates, bisphenol A diacrylate, pentaerythritol tetraacrylate, propylene glycol diacrylate, ethylene glycol diacrylate, trimethylol propane triacrylate, cyclohexane dimethanol diacrylate, tricyclodecane dimethanol diacrylate, neopentyl glycol diacrylate, tris(2-hydroxyethyl) isocyanurate triacrylate, and polybutadiene diacrylate, or the ethoxylated or propoxylated derivatives thereof. Yet other acrylates include hexane diol di(meth)acrylate and other $C_4$-$C_{10}$ alkane di(meth)acrylates, bisphenol A di(meth)acrylate, pentaerythritol tetra(meth)acrylate, propylene glycol di(meth)acrylate, ethylene glycol di(meth)acrylate, trimethylol propane tri(meth)acrylate, cyclohexane dimethanol di(meth)acrylate, tricyclodecane dimethanol d(meth)acrylate, neopentyl glycol di(meth)acrylate, tris(2-hydroxyethyl) isocyanurate tri(meth)acrylate, and polybutadiene di(meth)acrylate, or the ethoxylated or propoxylated derivatives thereof.

In some embodiments, the present disclosure provides for a reaction product between (i) a resin having one of the following structures:

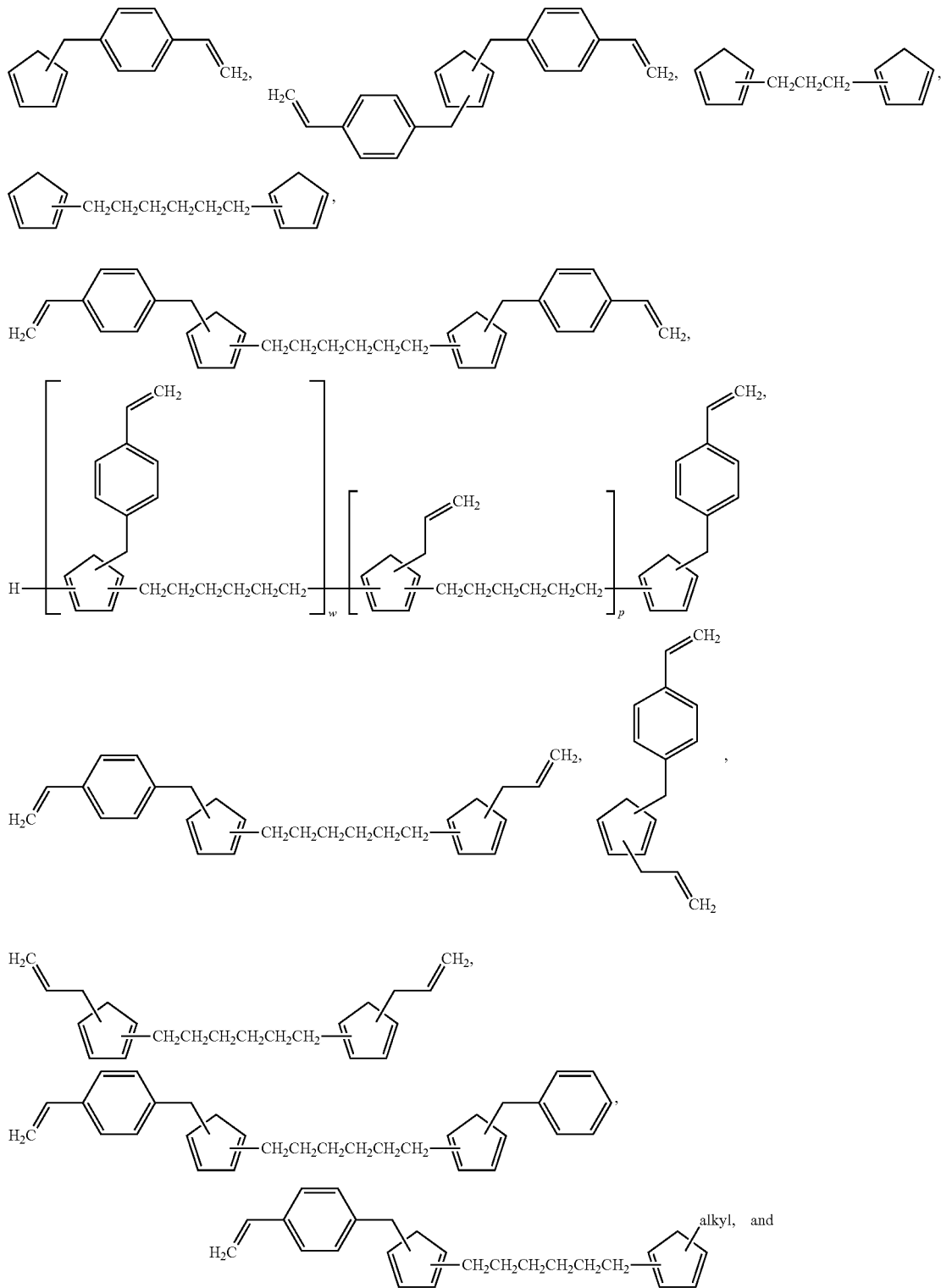

-continued

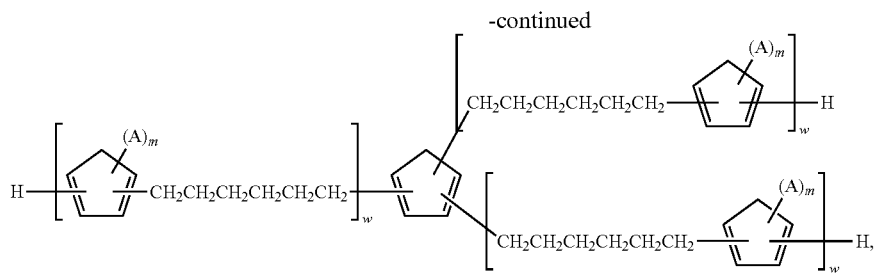

where w and p each are independently an integer ranging from 1 to 150;

and (ii) a dienophile, wherein the dienophile is selected from the group consisting of a bis-maleimide, a derivative of a bis-maleimide, a maleic anhydride, a derivative of a maleic anhydride, a benzoquinone, a derivative of a benzoquinone, and an acrylate.

In some embodiments, a composition is provided, the composition comprising at least two of the reaction products described above. In some embodiments, a ratio of a first reaction product to a second reaction product ranges from about 1:10 to about 10:1. In some embodiments, the ratio ranges from about 1:5 to about 5:1. In some embodiments, the ratio ranges from about 1:2 to about 2:1.

In some embodiments, reaction products between a compound of any of Formulas (IA) or (IB) and a dienophile have the structure set forth in Formulas (XIA) and (XIB):

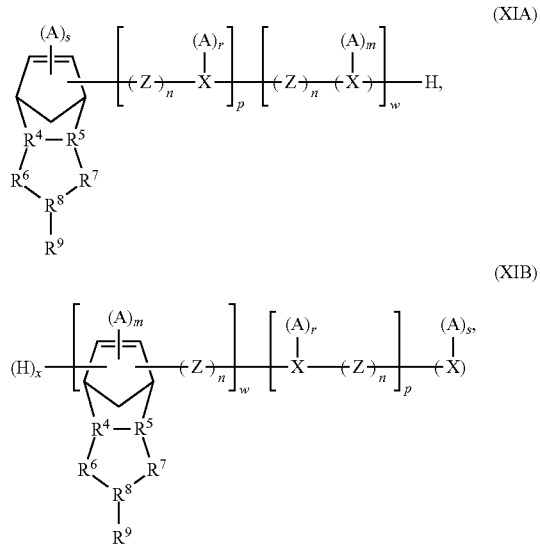

wherein $R^4$ and $R^5$ are independently —CH— or —C—$R^{12}$;

$R^6$ and $R^7$ are independently —C(O), —CH$_2$—, —CH$_2$—CH$_2$—, —C(O)CH$_2$—, or —CH$_2$—C(O)—;

$R^8$ is —C(H), O, N, or S; and $R^9$ is H, a saturated or unsaturated, straight-chain or branched, linear or cyclic, substituted or unsubstituted, aliphatic or aromatic group having between 1 and 40 carbon atoms, $R^{10}$—$R^{11}$, $R^{10}$—($R^{13}$)$_k$—$R^{11}$, or $R^{10}$—($R^{13}$)$_k$— $R^{10}$—$R^{11}$; or when $R^8$ is O or S, $R^9$ is one or more pairs of electrons;

each $R^{10}$ is independently a saturated or unsaturated, straight-chain or branched, linear or cyclic, substituted or unsubstituted, aliphatic or aromatic group having between 1 and 40 carbon atoms;

$R^{11}$ has the structure defined by Formula (XIC):

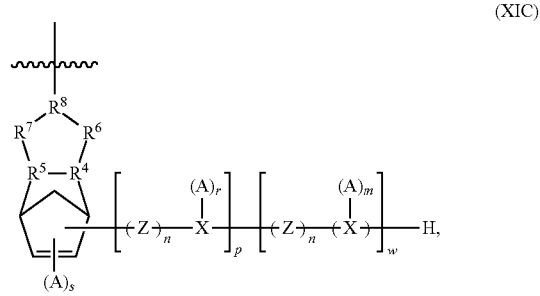

$R^{12}$ is F or a $C_1$-$C_4$ alkyl group;

$R^{13}$ is a saturated or unsaturated, straight-chain or branched, linear or cyclic, substituted or unsubstituted, aliphatic or aromatic group having between 1 and 50 carbon atoms, and which may be substituted with one or more heteroatoms selected from O, N, or S;

k is an integer ranging from 1 to 10; and where

X is a moiety comprising a cyclopentadiene-based ring;

each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

Z is a bond or straight-chain or branched, substituted or unsubstituted, aliphatic group having between 1 and 20 carbon atoms;

each m is an integer ranging from 1 to 5;

each n is 0 or 1;

each p is 0 or an integer ranging from 1 to 150;

each r is an integer ranging from 1 to 4;

each s is an integer ranging from 1 to 5;

each w is 0 or an integer ranging from 1 to 150; and x is 0 or 1.

In some embodiments of the resins of Formulas (XIA) and (XIB), $R^9$ or $R^{10}$ is a straight chain or branched, linear or cyclic, alkyl group having between 1 and 20 carbon atoms, which may be optionally substituted with one or more heteroatoms (e.g. O, N, or S). In some embodiments, $R^9$ or $R^{10}$ is a moiety having between 1 and 20 carbon atoms and having at least one aromatic or heteroaromatic group, and where the aromatic or heteroaromatic groups may be substituted or unsubstituted. By way of example, one of $R^9$ or $R^{10}$ may be -phenyl-[$C_1$-$C_4$ alkyl group]-phenyl-.

In some embodiments, $R^{10}$ comprises -[Aryl]-[Alkyl]-[Aryl], where each aryl group may be independently substituted or unsubstituted, and where the alkyl group comprises between 1 and 20 carbon atoms. In some embodiments, each [Aryl] group is optionally substituted with a $C_1$-$C_{10}$ straight chain or branched alkyl group.

In some embodiments, $R^{10}$ has the structure defined by Formula (XIVa):

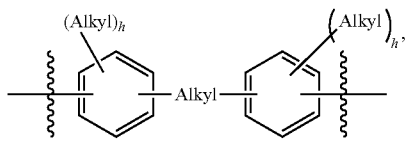

(XIVa)

wherein each alkyl group is independently straight chain or branched and comprises between 1 and 10 carbon atoms; and where each h is independently 0 or an integer ranging from 1 to 4. In some embodiments, each alkyl group independently comprises between 1 and 6 carbon atoms. In some embodiments, each alkyl group independently comprises between 1 and 4 carbon atoms. In some embodiments, each alkyl group independently comprises between 1 or 2 carbon atoms.

In some embodiments, at least one $(Alkyl)_h$ group is $-CH_3$. In some embodiments, at least one $(Alkyl)_h$ group is $-CH_2-CH_3$. In some embodiments, at least one $(Alkyl)_h$ group is $-C(H)(CH_3)_2$.

In some embodiments, each $(Alkyl)_h$ group is $-CH_2-CH_3$. In some embodiments, each aryl group comprises two $(Alkyl)_h$ groups, and each $(Alkyl)_h$ group is $-CH_2-CH_3$.

In some embodiments, each aryl group comprises two $(Alkyl)_h$ groups, where a first $(Alkyl)_h$ group is $-CH_3$ and another $(Alkyl)_h$ group is $-C(H)(CH_3)_2$.

In some embodiments, $R^{10}$ has the structure

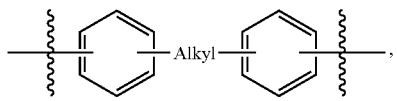

wherein the alkyl group is a straight chain or branched and comprises between 1 and 10 carbon atoms. In some embodiments, the alkyl group comprises between 1 and 4 carbon atoms. In some embodiments, the alkyl group is $-CH_2-$.

In some embodiments, $R^{10}$ is a branched alkyl group comprising between 1 and 12 carbon atoms. In some embodiments, $R^{10}$ is a branched alkyl group comprising between 1 and 10 carbon atoms. In some embodiments, $R^{10}$ is a branched alkyl group comprising between 1 and 9 carbon atoms. In some embodiments, $R^{10}$ is $-CH_2-C(CH_3)_2-CH_2-CH(CH_3)-CH_2-CH_2-$.

In some embodiments, $R^{10}$ is a 6-membered aromatic ring, optionally substituted with up to four alkyl groups.

In some embodiments, $R^{10}$ is a six-membered cycloalkyl group, optionally substituted with up to four alkyl groups.

In some embodiments, $R^{10}$ is -[Alkyl]-[Cycloalkyl]-[Alkyl]-, where each alkyl group is linear or branched and comprises from 1 to 10 carbon atoms; and where the cycloalkyl group comprises between 4 and 8 carbon atoms, the cycloalkyl group being optionally substituted with one or more straight chain or branched alkyl groups, each having between 1 and 10 carbon atoms.

In some embodiments, reaction products between a compound of any of Formulas (IA) or (IB) and a dienophile have the structure set forth in Formulas (XID) and (XIE):

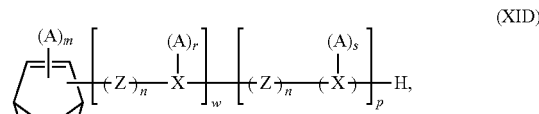

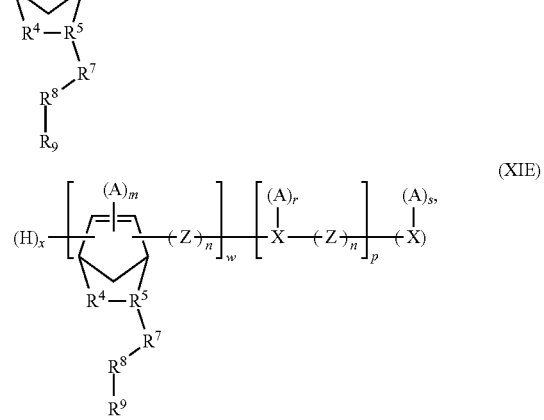

wherein $R^4$ and $R^5$ are independently —CH— or —C—$R^{12}$;

$R^7$ is —C(O), —$CH_2$—, —$CH_2$—$CH_2$—, —C(O)$CH_2$—, or —$CH_2$—C(O)—;

$R^8$ is —C(H)—, O, N, or S; and $R^9$ is H, a saturated or unsaturated, straight-chain or branched, linear or cyclic, substituted or unsubstituted, aliphatic or aromatic group having between 1 and 40 carbon atoms;

$R^{12}$ is F or a $C_1$-$C_4$ alkyl group;

X is a moiety comprising a cyclopentadiene-based ring;

each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

Z is a bond or straight-chain or branched, substituted or unsubstituted, aliphatic group having between 1 and 20 carbon atoms;

m is an integer ranging from 1 to 5;

n is 0 or 1;

p is 0 or an integer ranging from 1 to 150;

r is an integer ranging from 1 to 4;

s is an integer ranging from 1 to 5; and w is 0 or an integer ranging from 1 to 150; and x is 0 or 1.

In some embodiments, reaction products between a compound of any of Formulas (IA) or (IB) and a dienophile have the structure set forth in Formulas (XIF) and (XIG):

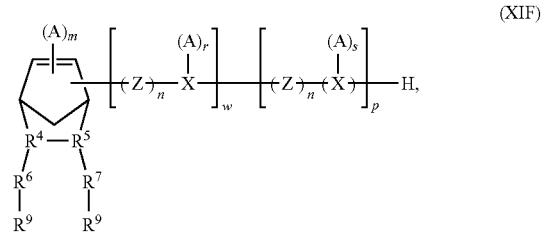

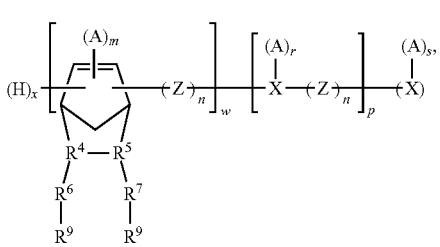

(XIG)

wherein
$R^4$ and $R^5$ are independently —CH— or —C—$R^{12}$;
$R^6$ and $R^7$ each are —C(O)—,
each $R^9$ is independently H, a saturated or unsaturated, straight-chain or branched, linear or cyclic, substituted or unsubstituted, aliphatic group having between 1 and 40 carbon atoms and optionally substituted with O, N, or S;
$R^{12}$ is F or a $C_1$-$C_4$ alkyl group; and
where
X is a moiety comprising a cyclopentadiene-based ring;
each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;
Z is a bond or straight-chain or branched, substituted or unsubstituted, aliphatic group having between 1 and 20 carbon atoms;
m is an integer ranging from 1 to 5;
n is 0 or 1;
p is 0 or an integer ranging from 1 to 150;
r is an integer ranging from 1 to 4;
s is an integer ranging from 1 to 5; and
w is 0 or an integer ranging from 1 to 150; and
x is 0 or 1.

In some embodiments, each $R^9$ is independently selected from —O-alkyl. In some embodiments, each $R^9$ is independently selected from —O—($C_1$-$C_{20}$)—. In some embodiments, each $R^9$ is independently selected from —O—($C_1$-$C_{10}$). In some embodiments, each $R^9$ is independently selected from —O—($C_1$-$C_6$). In some embodiments, each $R^9$ is independently selected from —O—($C_1$-$C_4$). In some embodiments, each $R^9$ is independently selected from —O—($C_1$-$C_3$).

In some embodiments, reaction products between a compound of any of Formulas (IA) or (IB) and a dienophile have the structure set forth in Formulas (XIIA) or (XIIB).

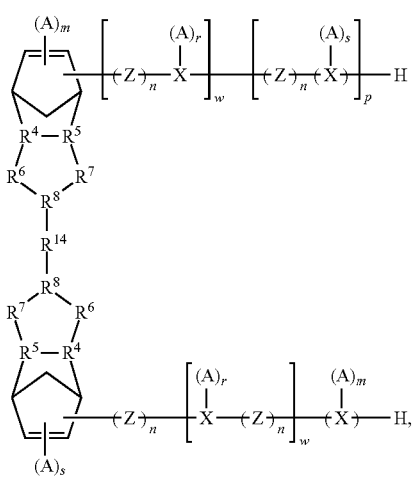

(XIIA)

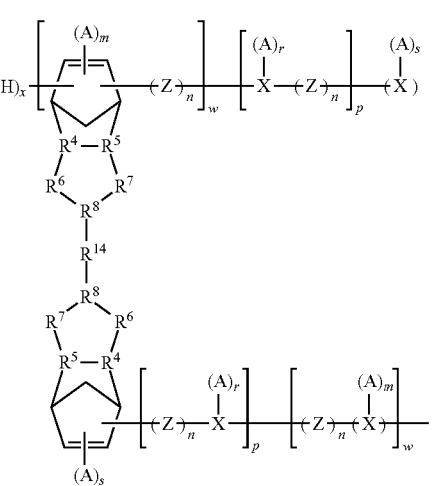

(XIIB)

wherein
$R^4$ and $R^5$ are independently —CH— or —C—$R^{12}$;
$R^6$ and $R^7$ are independently —C(O), —$CH_2$—, —$CH_2$—$CH_2$—, —C(O)$CH_2$—, or —$CH_2$—C(O)—;
$R^8$ is —CH— or —N—;
$R^{12}$ is F or a $C_1$-$C_4$ alkyl group;
$R^{13}$ is a saturated or unsaturated, straight-chain or branched, linear or cyclic, substituted or unsubstituted, aliphatic or aromatic group having between 1 and 50 carbon atoms, and which may be substituted with one or more heteroatoms selected from O, N, or S;
$R^{14}$ is a saturated or unsaturated, straight-chain or branched, linear or cyclic, substituted or unsubstituted, aliphatic or aromatic group having between 1 and 40 carbon atoms; —($R^{13}$)$_k$—$R^{15}$—, —$R^{15}$—($R^{13}$)$_k$— or —$R^{15}$—($R^{13}$)$_k$—$R^{15}$—;
each $R^{15}$ is independently a saturated or unsaturated, straight-chain or branched, linear or cyclic, substituted or unsubstituted, aliphatic or aromatic group having between 1 and 40 carbon atoms;
k is an integer ranging from 1 to 10;
where
X is a moiety comprising a cyclopentadiene-based ring;
each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;
Z is a bond or straight-chain or branched, substituted or unsubstituted, aliphatic group having between 1 and 20 carbon atoms;
each m is an integer ranging from 1 to 5;
each n is 0 or 1;
each p is 0 or an integer ranging from 1 to 150;
each r is an integer ranging from 1 to 4;
each s is an integer ranging from 1 to 5; and
each w is 0 or an integer ranging from 1 to 150; and
x is 0 or 1.

In some embodiments, $R^{14}$ comprises -[Aryl]-[Alkyl]-[Aryl]-, where each aryl group may be independently substituted or unsubstituted, and where the alkyl group comprises between 1 and 20 carbon atoms. In some embodiments, each [Aryl] group is optionally substituted with a $C_1$-$C_{10}$ straight chain or branched alkyl group.

In some embodiments, $R^{14}$ has the structure defined by Formula (XIVa):

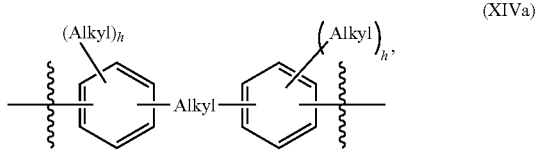
(XIVa)

wherein each alkyl group is independently straight chain or branched and comprises between 1 and 10 carbon atoms; and where each h is independently 0 or an integer ranging from 1 to 4. In some embodiments, each alkyl group independently comprises between 1 and 6 carbon atoms. In some embodiments, each alkyl group independently comprises between 1 and 4 carbon atoms. In some embodiments, each alkyl group independently comprises between 1 or 2 carbon atoms.

In some embodiments, at least one (Alkyl)$_h$ group is —CH$_3$. In some embodiments, at least one (Alkyl)$_h$ group is —CH$_2$—CH$_3$. In some embodiments, at least one (Alkyl)$_h$ group is —C(H)(CH$_3$)$_2$.

In some embodiments, each (Alkyl)$_h$ group is —CH$_2$—CH$_3$. In some embodiments, each aryl group comprises two (Alkyl)$_h$ groups, and each (Alkyl)$_h$ group is —CH$_2$—CH$_3$.

In some embodiments, each aryl group comprises two (Alkyl)$_h$ groups, where a first (Alkyl)$_h$ group is —CH$_3$ and another (Alkyl)$_h$ group is —C(H)(CH$_3$)$_2$.

In some embodiments, $R^{14}$ has the structure

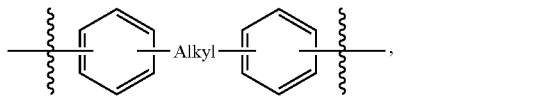

wherein the alkyl group is a straight chain or branched and comprises between 1 and 10 carbon atoms. In some embodiments, the alkyl group comprises between 1 and 4 carbon atoms. In some embodiments, the alkyl group is —CH$_2$—.

In some embodiments, $R^{14}$ is a branched alkyl group comprising between 1 and 12 carbon atoms. In some embodiments, $R^{14}$ is a branched alkyl group comprising between 1 and 10 carbon atoms. In some embodiments, $R^{14}$ is a branched alkyl group comprising between 1 and 9 carbon atoms. In some embodiments, $R^{14}$ is —CH$_2$—C(CH$_3$)$_2$—CH$_2$—CH(CH$_3$)—CH$_2$—CH$_2$—.

In some embodiments, $R^{14}$ is a six-membered cycloalkyl group, optionally substituted with up to four alkyl groups. In some embodiments, $R^{14}$ is a six-membered cycloalkyl group, optionally substituted with up to four —CH$_3$ groups. In some embodiments, $R^{14}$ is a six-membered cycloalkyl group, optionally substituted with up to two —CH$_3$ groups.

In some embodiments, $R^{14}$ is a six-membered cycloalkyl group, optionally substituted with up to four alkyl groups.

In some embodiments, $R^{14}$ is -[Alkyl]-[Cycloalkyl]-[Alkyl]-, where each alkyl group is linear or branched and comprises from 1 to 10 carbon atoms; and where the cycloalkyl group comprises between 4 and 8 carbon atoms, the cycloalkyl group being optionally substituted with one or more straight chain or branched alkyl groups, each having between 1 and 10 carbon atoms.

In another aspect of the present disclosure is a composition comprising a blend of one or more compounds of any of Formulas (XIIA) or (XIIB) In some embodiments, a ratio of a first compound of any of Formulas (XIIA) or (XIIB) to a second compound of any of any of Formulas (XIIA) or (XIIB) ranges from about 1:10 to about 10:1. In some embodiments, the ratio ranges from about 1:5 to about 5:1. In some embodiments, the ratio ranges from about 1:2 to about 2:1.

In some embodiments, reaction products between a compound of any of Formulas (IA) or (IB) and a dienophile have the structure set forth in Formulas (XIIC) or (XIID).

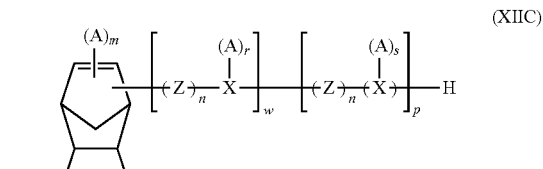
(XIIC)

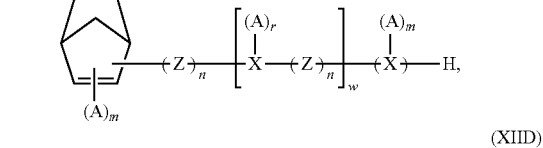

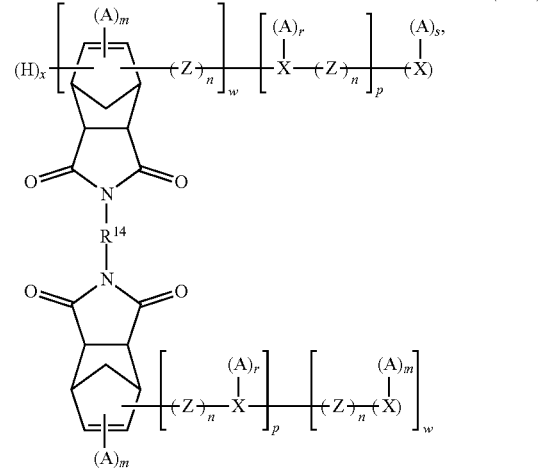
(XIID)

wherein
$R^{13}$ is a saturated or unsaturated, straight-chain or branched, linear or cyclic, substituted or unsubstituted, aliphatic or aromatic group having between 1 and 50 carbon atoms, and which may be substituted with one or more heteroatoms selected from O, N, or S;

$R^{14}$ is a saturated or unsaturated, straight-chain or branched, linear or cyclic, substituted or unsubstituted, aliphatic or aromatic group having between 1 and 40 carbon atoms; —(R$^{13}$)$_k$—R$^{15}$—, —R$^{15}$—(R$^{13}$)$_k$— or —R$^{15}$—(R$^{13}$)$_k$—R$^{15}$—;

each $R^{15}$ is independently a saturated or unsaturated, straight-chain or branched, linear or cyclic, substituted or unsubstituted, aliphatic or aromatic group having between 1 and 40 carbon atoms;

k is an integer ranging from 1 to 10;

where

X is a moiety comprising a cyclopentadiene-based ring;

each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

Z is a bond or straight-chain or branched, substituted or unsubstituted, aliphatic group having between 1 and 20 carbon atoms;

each m is an integer ranging from 1 to 5;
each n is 0 or 1;
each p is 0 or an integer ranging from 1 to 150;
each r is an integer ranging from 1 to 4;
each s is an integer ranging from 1 to 5; and
each w is 0 or an integer ranging from 1 to 150; and
x is 0 or 1.

In some embodiments, $R^{14}$ is comprises -[Aryl]-[Alkyl]-[Aryl]-, where each aryl group may be independently substituted or unsubstituted, and where the alkyl group comprises between 1 and 20 carbon atoms. In some embodiments, each [Aryl] group is optionally substituted with a $C_1$-$C_{10}$ straight chain or branched alkyl group.

In some embodiments, $R^{14}$ has the structure defined by Formula (XIVa):

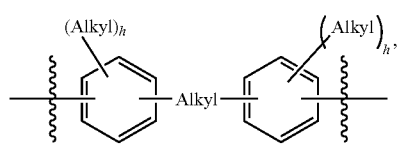

wherein each alkyl group is independently straight chain or branched and comprises between 1 and 10 carbon atoms; and where each h is independently 0 or an integer ranging from 1 to 4. In some embodiments, each alkyl group independently comprises between 1 and 6 carbon atoms. In some embodiments, each alkyl group independently comprises between 1 and 4 carbon atoms. In some embodiments, each alkyl group independently comprises between 1 or 2 carbon atoms.

In some embodiments, at least one $(Alkyl)_h$ group is —$CH_3$. In some embodiments, at least one $(Alkyl)_h$ group is —$CH_2$—$CH_3$—. In some embodiments, at least one $(Alkyl)_h$ group is —$C(H)(CH_3)_2$.

In some embodiments, each $(Alkyl)_h$ group is —$CH_2$—$CH_3$. In some embodiments, each aryl group comprises two $(Alkyl)_h$ groups, and each $(Alkyl)_h$ group is —$CH_2$—$CH_3$.

In some embodiments, each aryl group comprises two $(Alkyl)_h$ groups, where a first $(Alkyl)_h$ group is —$CH_3$ and another $(Alkyl)_h$ group is —$C(H)(CH_3)_2$.

In some embodiments, $R^{14}$ has the structure

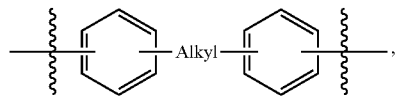

wherein the alkyl group is a straight chain or branched and comprises between 1 and 10 carbon atoms. In some embodiments, the alkyl group comprises between 1 and 4 carbon atoms. In some embodiments, the alkyl group is —$CH_2$—.

In some embodiments, $R^{14}$ is a branched alkyl group comprising between 1 and 12 carbon atoms. In some embodiments, $R^{14}$ is a branched alkyl group comprising between 1 and 10 carbon atoms. In some embodiments, $R^{14}$ is a branched alkyl group comprising between 1 and 9 carbon atoms. In some embodiments, $R^{14}$ is —$CH_2$—$C(CH_3)_2$—$CH_2$—$CH(CH_3)$—$CH_2$—$CH_2$—.

In some embodiments, $R^{14}$ is a six-membered cycloalkyl group, optionally substituted with up to four alkyl groups. In some embodiments, $R^{14}$ is a six-membered cycloalkyl group, optionally substituted with up to four —$CH_3$ groups. In some embodiments, $R^{14}$ is a six-membered cycloalkyl group, optionally substituted with up to two —$CH_3$ groups.

In some embodiments, $R^{14}$ is a six-membered cycloalkyl group, optionally substituted with up to four alkyl groups.

In some embodiments, $R^{14}$ is -[Alkyl]-[Cycloalkyl]-[Alkyl]-, where each alkyl group is linear or branched and comprises from 1 to 10 carbon atoms; and where the cycloalkyl group comprises between 4 and 8 carbon atoms, the cycloalkyl group being optionally substituted with one or more straight chain or branched alkyl groups, each having between 1 and 10 carbon atoms.

In some embodiments, reaction products between a compound of any of Formulas (IA) or (IB) and a dienophile have the structure set forth in Formula (XIIE).

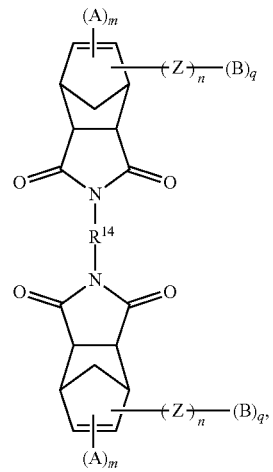

wherein
$R^{13}$ is a saturated or unsaturated, straight-chain or branched, linear or cyclic, substituted or unsubstituted, aliphatic or aromatic group having between 1 and 50 carbon atoms, and which may be substituted with one or more heteroatoms selected from O, N, or S;

$R^{14}$ is a saturated or unsaturated, straight-chain or branched, linear or cyclic, substituted or unsubstituted, aliphatic or aromatic group having between 1 and 40 carbon atoms; —$(R^{13})_k$—$R^{15}$—, —$R^{14}$—$(R^{13})_k$— or —$R^{15}$—$(R^{13})_k$—$R^{15}$—;

each $R^{15}$ is independently a saturated or unsaturated, straight-chain or branched, linear or cyclic, substituted or unsubstituted, aliphatic or aromatic group having between 1 and 40 carbon atoms;

k is an integer ranging from 1 to 10;
B is H or $X(A)_s$;
X is a moiety comprising a cyclopentadiene-based ring;
each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

Z is a bond or straight-chain or branched, substituted or unsubstituted, aliphatic group having between 1 and 20 carbon atoms;

each m is an integer ranging from 1 to 5;
each n is 0 or 1;
each q is 0 or 1; and
each s is an integer ranging from 1 to 5.

In some embodiments, $R^{14}$ is comprises -[Aryl]-[Alkyl]-[Aryl]-, where each aryl group may be independently substituted or unsubstituted, and where the alkyl group comprises between 1 and 20 carbon atoms. In some embodiments, each [Aryl] group is optionally substituted with a $C_1$-$C_{10}$ straight chain or branched alkyl group.

In some embodiments, $R^{14}$ has the structure defined by Formula (XIVa):

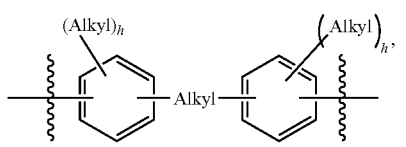

(XIVa)

wherein each alkyl group is independently straight chain or branched and comprises between 1 and 10 carbon atoms; and where each h is independently 0 or an integer ranging from 1 to 4. In some embodiments, each alkyl group independently comprises between 1 and 6 carbon atoms. In some embodiments, each alkyl group independently comprises between 1 and 4 carbon atoms. In some embodiments, each alkyl group independently comprises between 1 or 2 carbon atoms. In some embodiments, at least one $(Alkyl)_h$ group is —$CH_3$. In some embodiments, at least one $(Alkyl)_h$ group is —$CH_2$—$CH_3$. In some embodiments, at least one $(Alkyl)_h$ group is —$C(H)(CH_3)_2$. In some embodiments, each $(Alkyl)_h$ group is —$CH_2$—$CH_3$. In some embodiments, each aryl group comprises two $(Alkyl)_h$ groups, and each $(Alkyl)_h$ group is —$CH_2$—$CH_3$. In some embodiments, each aryl group comprises two $(Alkyl)_h$ groups, where a first $(Alkyl)_h$ group is —$CH_3$ and another $(Alkyl)_h$ group is —$C(H)(CH_3)_2$.

In some embodiments, $R^{14}$ has the structure

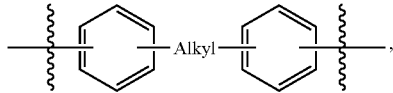

wherein the alkyl group is a straight chain or branched and comprises between 1 and 10 carbon atoms. In some embodiments, the alkyl group comprises between 1 and 4 carbon atoms. In some embodiments, the alkyl group is —$CH_2$—.

In some embodiments, $R^{14}$ is a branched alkyl group comprising between 1 and 12 carbon atoms. In some embodiments, $R^{14}$ is a branched alkyl group comprising between 1 and 10 carbon atoms. In some embodiments, $R^{14}$ is a branched alkyl group comprising between 1 and 9 carbon atoms. In some embodiments, $R^{14}$ is —$CH_2$—$C(CH_3)_2$—$CH_2$—$CH(CH_3)$—$CH_2$—$CH_2$—.

In some embodiments, $R^{14}$ is a 6-membered aromatic ring, optionally substituted with up to four alkyl groups.

In some embodiments, $R^{14}$ is a six-membered cycloalkyl group, optionally substituted with up to four alkyl groups. In some embodiments, $R^{14}$ is a six-membered cycloalkyl group, optionally substituted with up to four —$CH_3$ groups. In some embodiments, $R^{14}$ is a six-membered cycloalkyl group, optionally substituted with up to two —$CH_3$ groups.

In some embodiments, $R^{14}$ is -[Alkyl]-[Cycloalkyl]-[Alkyl]-, where each alkyl group is linear or branched and comprises from 1 to 10 carbon atoms; and where the cycloalkyl group comprises between 4 and 8 carbon atoms, the cycloalkyl group being optionally substituted with one or more straight chain or branched alkyl groups, each having between 1 and 10 carbon atoms.

In some embodiments, $R^{14}$ is -[Aryl]-$(R^{13})_k$-[Aryl]-, where each aryl group may be independently substituted or unsubstituted. In some embodiments, each -[Aryl]- group is optionally substituted with a $C_1$-$C_{10}$ straight chain or branched alkyl group. In some embodiments, each -[Aryl]- group is unsubstituted.

In some embodiments, $R^{14}$ is -[alkyl]-$(R^{13})_k$—, where the alkyl group may comprises between 1 and 40 carbon atoms. In some embodiments, $R^{14}$ is -[alkyl]-[cycloalkyl][alkyl]-$(R^{13})_k$—, the cycloalkyl group comprising between 4 and 8 carbon atoms, the cycloalkyl group being optionally substituted with one or more straight chain or branched alkyl groups, each having between 1 and 10 carbon atoms.

In some embodiments, $R^{13}$ comprises a moiety including a substituted phenyl group.

In some embodiments, reaction products between a compound of any of Formulas (IA) or (IB) and a dienophile have the structure set forth in Formula (XIIF):

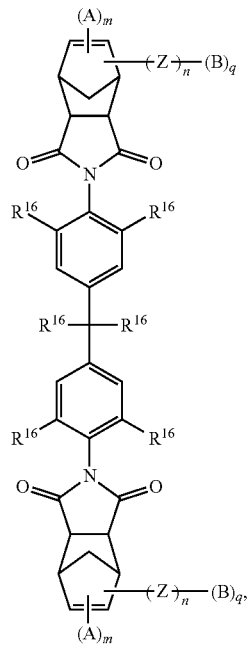

(XIIF)

wherein
each $R^{16}$ is independently H or a substituted or unsubstituted, linear or branched, linear or cyclic alkyl group having between 1 and 10 carbon atoms;

B is H or $X(A)_s$;

X is a moiety comprising a cyclopentadiene-based ring;

each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

Z is a bond or straight-chain or branched, substituted or unsubstituted, aliphatic group having between 1 and 20 carbon atoms;

each m is an integer ranging from 1 to 5;

each n is 0 or 1;

each q is 0 or 1; and each s is an integer ranging from 1 to 5.

In some embodiments, each $R^{16}$ is independently H or a $C_1$-$C_4$ alkyl group.

In some embodiments, reaction products between a compound of any of Formulas (IA) or (IB) and a dienophile have the structure set forth in Formula (XIII):

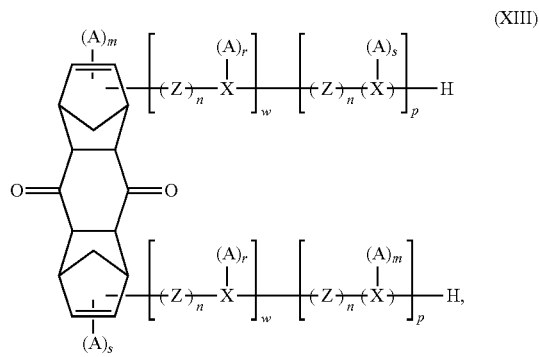

wherein

X is a moiety comprising a cyclopentadiene-based ring;

each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

Z is a bond or straight-chain or branched, substituted or unsubstituted, aliphatic group having between 1 and 20 carbon atoms;

each m is an integer ranging from 1 to 5;

each n is 0 or 1;

each p is 0 or an integer ranging from 1 to 150;

each r is an integer ranging from 1 to 4; and w is 0 or an integer ranging from 1 to 150; and x is 0 or 1.

In some embodiments of the compounds of Formula (XIII), one of w or p is 0. In other embodiments, w and p are both 0.

Specific examples of the reaction products of a resin of any of Formulas (IA) or (IB) and a dienophile are illustrated within the synthetic examples herein.

Synthesis of the Compounds of Any of Formulas (XIA), (XIB), (XID) to (XIG), (XIIA) to (XIIF), and (XIII)

In some embodiments, the compounds of Formulas (XIA), (XIB), (XID) to (XIG), (XIIA) to (XIIF), and (XIII) may be prepared by neat blending combination of resins of Formulas (IA) or (IB) with one or more suitable dienophiles, including those described herein. In other embodiments, compounds of Formulas (XIA), (XIB), (XID) to (XIG), (XIIA) to (XIIF), and (XIII) may be prepared by combination of resins of Formula (IA) or (IB) with one or more suitable dienophiles in an organic solvent at moderate temperatures (typically between 0° C. and 100° C.). Reactions between resins of Formulas (IA) or (IB) and suitable dienophiles are typically rapid and self-initiating, and compounds of Formulas (XIA), (XIB), (XID) to (XIG), (XIIA) to (XIIF), and (XIII) can be used as-generated, or purified by removal of reaction solvent in vacuo as desired.

In some embodiments, an excess of diene is used compared to an amount of dienophile. In other embodiments, a ratio of an amount of diene to dienophile ranges from about 1:1 to about 1:4. In other embodiments, a ratio of an amount of diene to dienophile ranges from about 1:1 to about 1:2.

In some embodiments, the compounds of Formulas (XIA), (XIB), (XID) to (XIG), (XIIA) to (XIIF), and (XIII) may be prepared according to the methods outlined in the following non-limiting synthetic schemes:

Scheme 1: General Synthesis of a Resin Utilizing a Bismaleimide

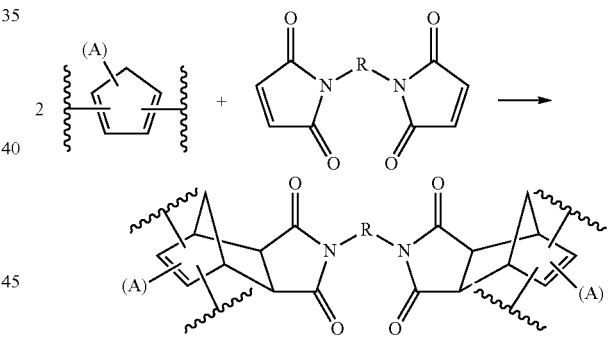

where R is $R^{14}$ as defined herein.

Scheme 2: Synthesis of a Resin Utilizing 4,4′methylenebis(2,6-diethylaniline)

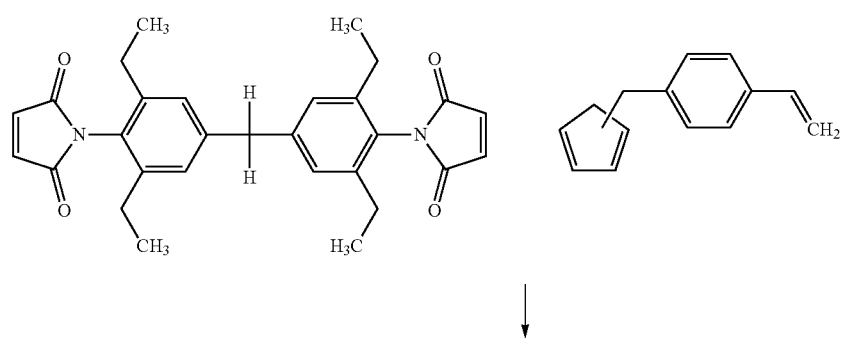

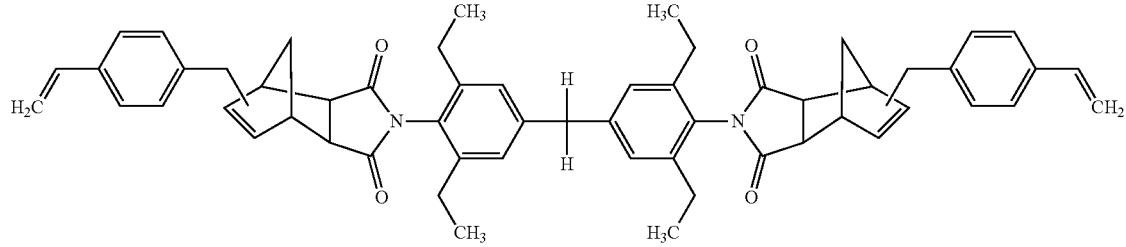
Scheme 3: Synthesis of a Resin Utilizing 4,4′methylenebis(2-iropropyl-6-methylaniline)
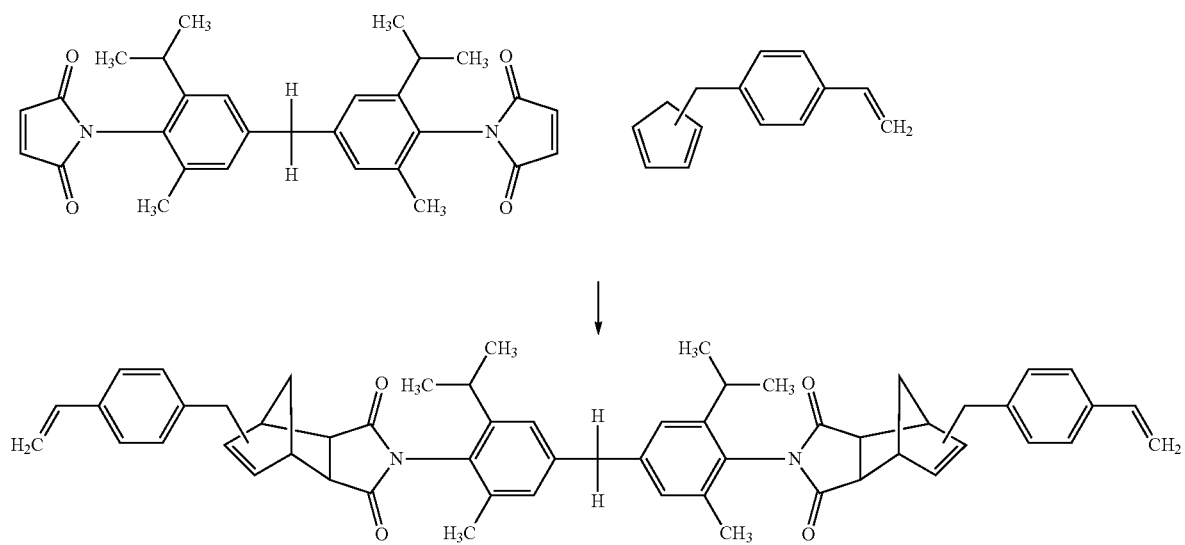
Scheme 4: Synthesis of Resin Utilizing a Maleic Anhydride
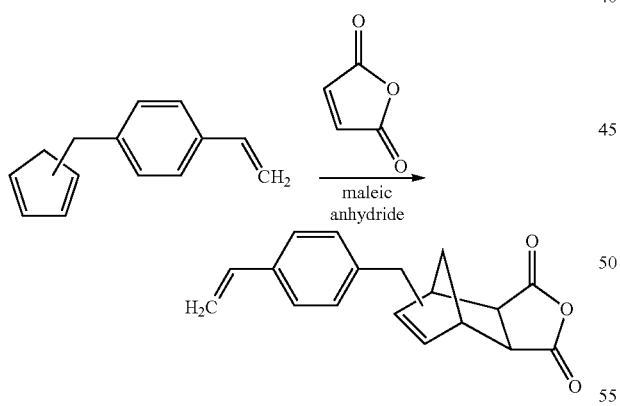
Alternate structure view
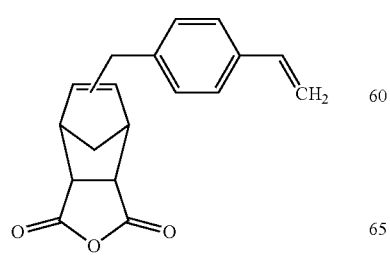

Scheme 5: Synthesis of a Resin from an Oligomerized Dimer Diamine
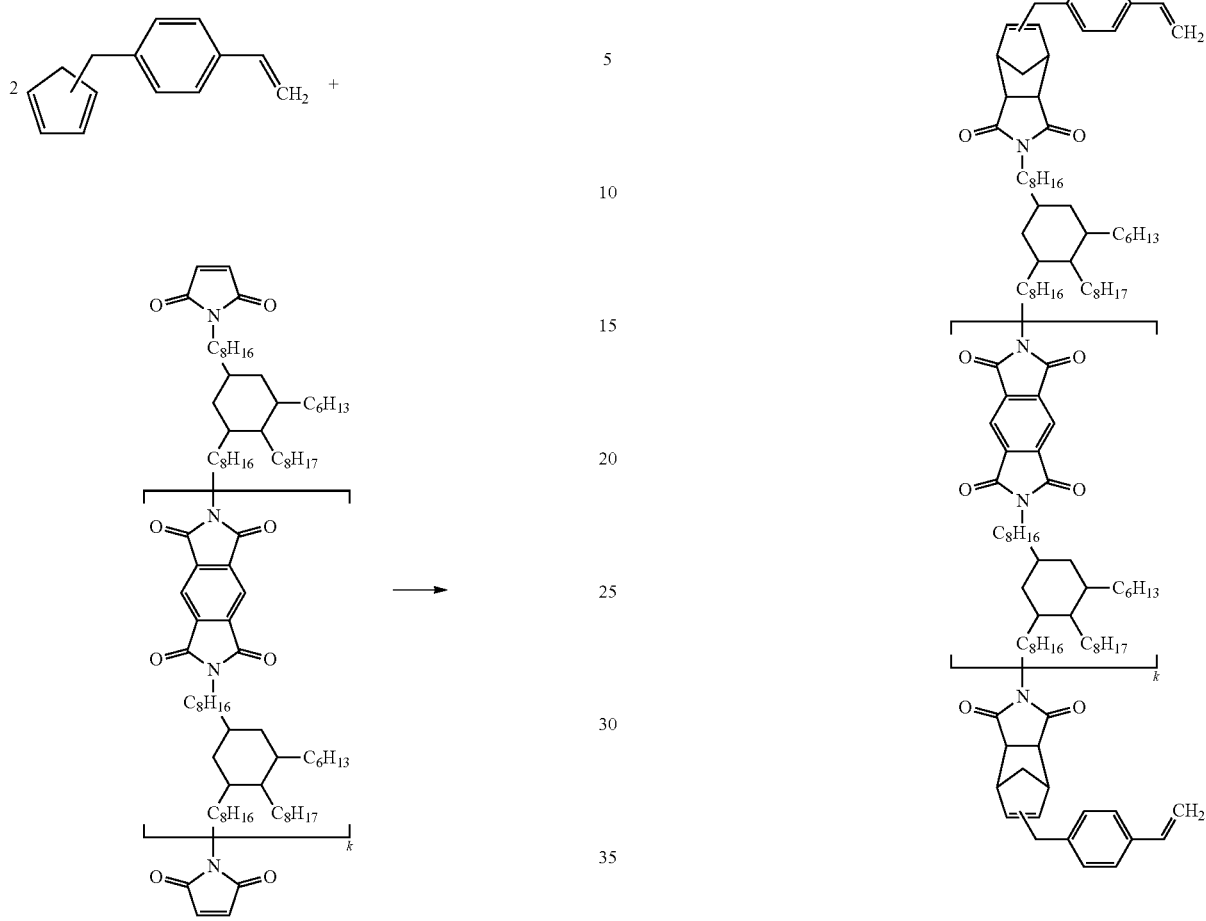
where n is an integer ranging from 1 to 10.
Scheme 6: Synthesis of a Resin using 1,6-bismalemidie-(2,2,4-trimethyl)hexane
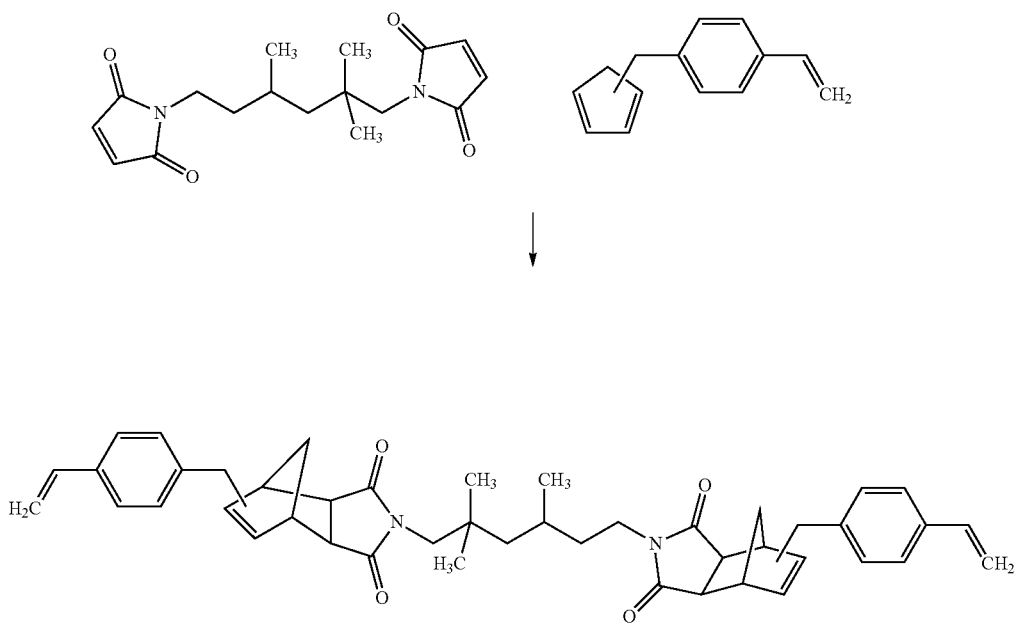

Scheme 7: Synthesis of a Resin using Polyphenylmethanebismaleimide
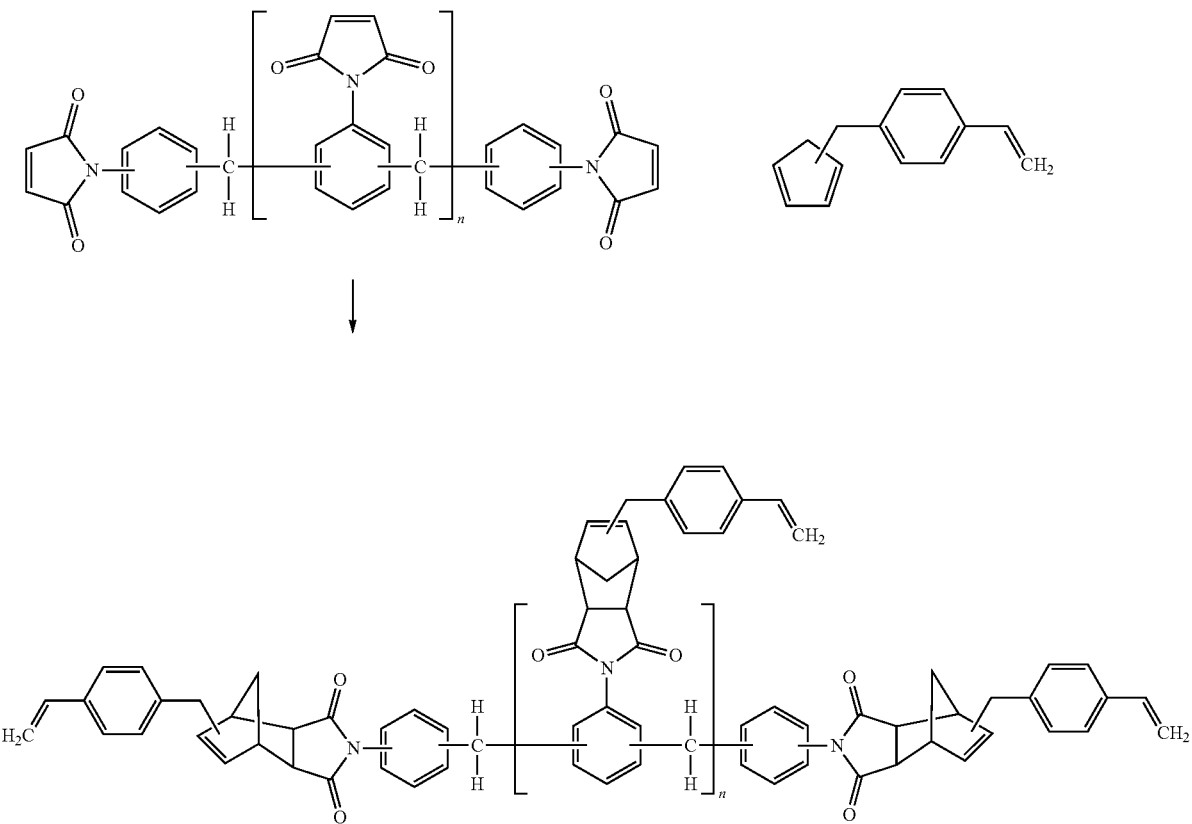
where n is an integer ranging from 1 to 10.
Scheme 8: Synthesis of a Resin Utilizing 4,4-diphenylmethane bismalemide
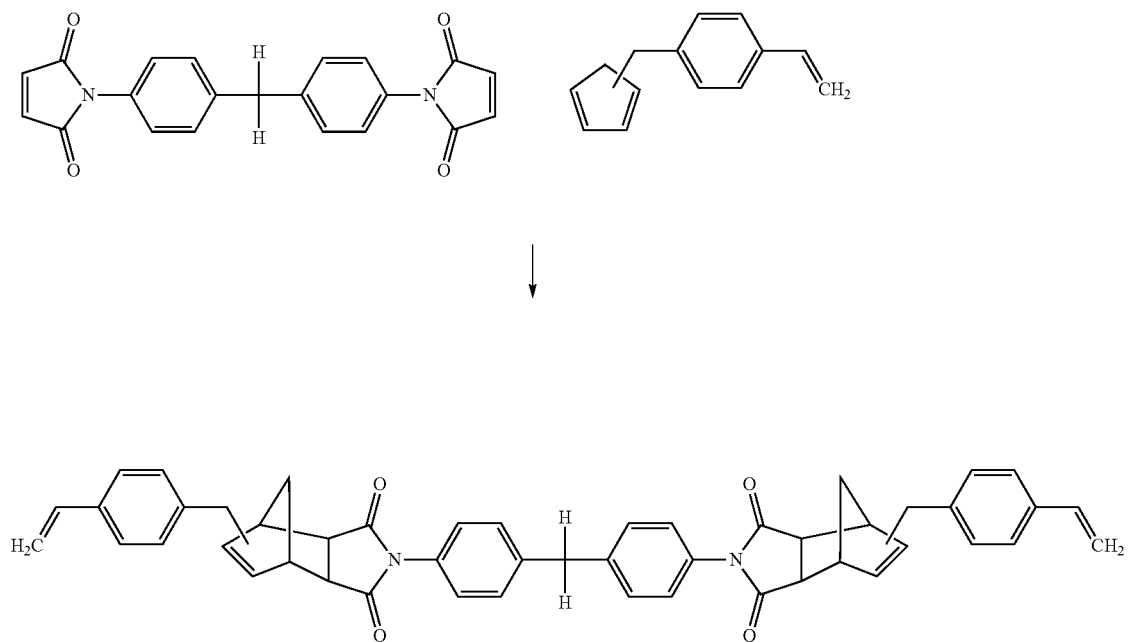

Scheme 9: Synthesis of a Resin Utilizing N,N'-(4-methyl-m-phenylene)-bismalemide
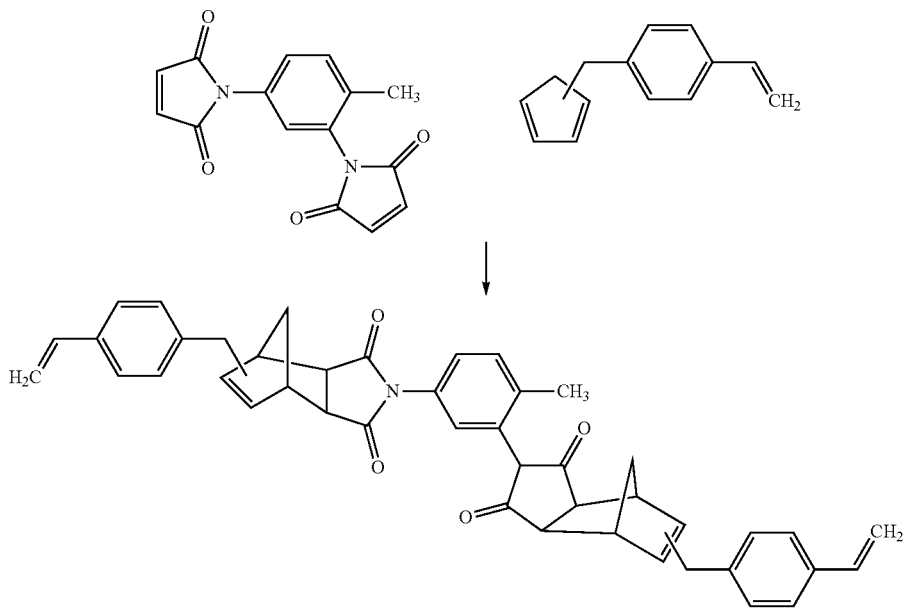
Scheme 10: Synthesis of a Resin (self-Diels Alder reaction)
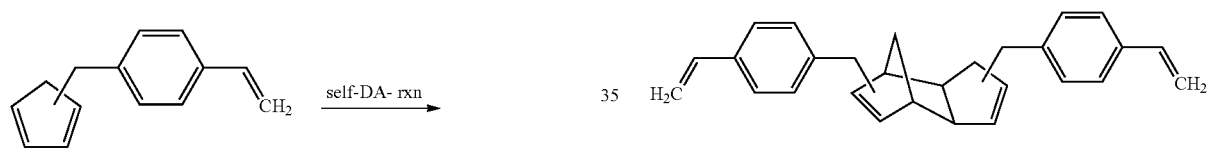
Scheme 11: Synthesis of a Resin Utilizing N,N'm-phenylenebismalemide
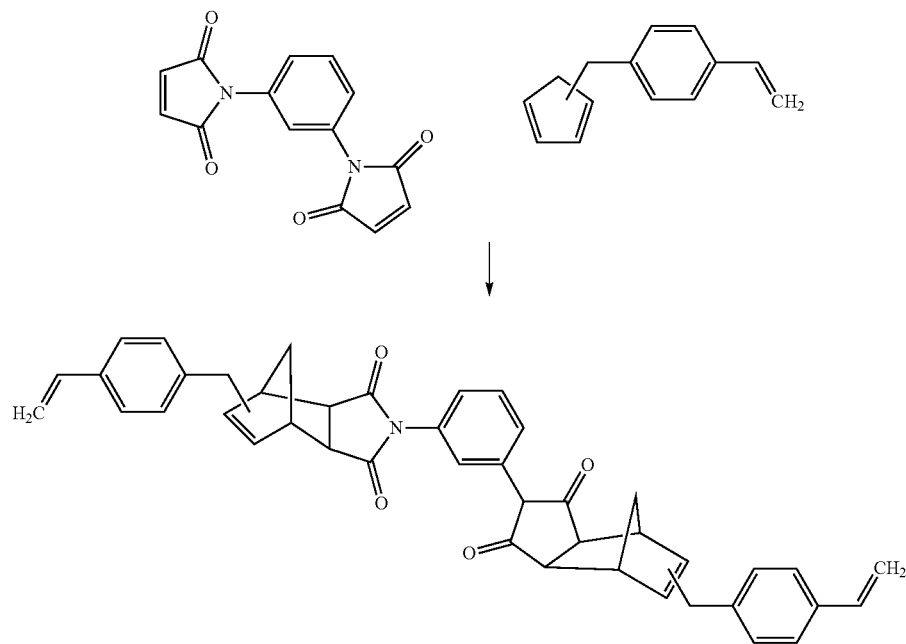

Scheme 12: Synthesis of a Resin using bismaleimide of a dimer diamine

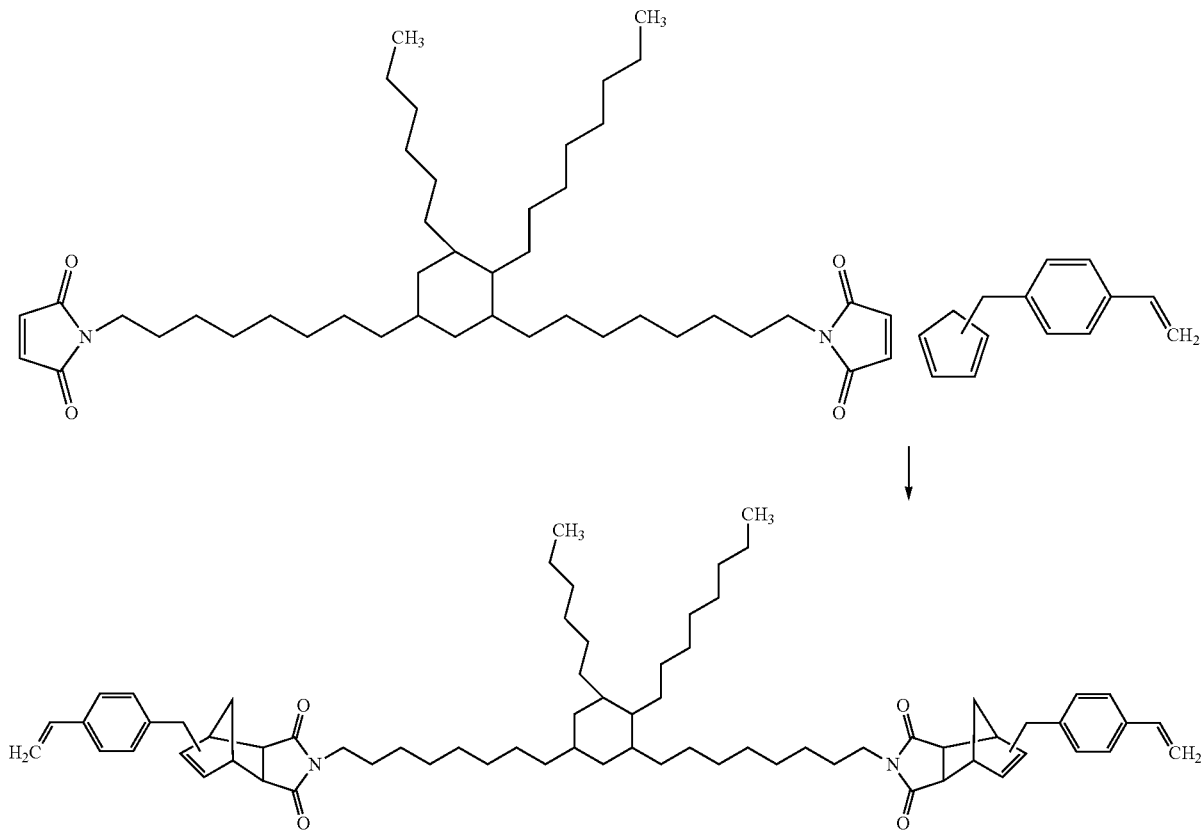

Scheme 13: Synthesis of Resin using a mono-maleimide

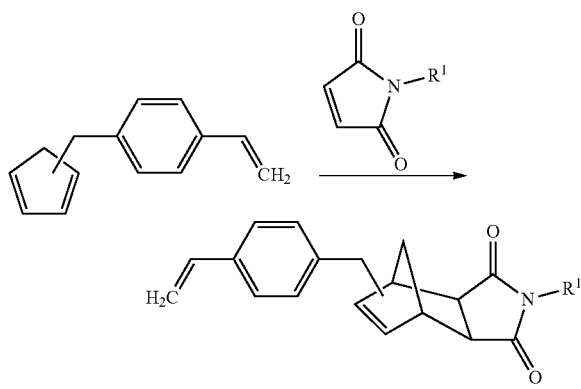

Polymers, Copolymers, and Blends of Resins

In some embodiments, a polymer is provided, the polymer being derived from one or more resins of Formulas (IA) or (IB) (or any like resin disclosed herein). In some embodiments, the at least one of the resins of Formulas (IA) or (IB) comprises at least one A moiety terminating in one of a —CH=CH$_2$ group, a —CH=CH—CH$_3$, or alkyne group. In some embodiments, the polymer further comprises an additive selected from the group consisting of adhesion agents, peroxides/crosslinking agents, antioxidants, flame retardants, diluents and fillers.

In some embodiments, a co-polymer is provided, the co-polymer derived from a first resin of Formulas (IA) or (IB) and a second resin of Formulas (IA) or (IB), wherein the first and second resins are different. In some embodiments, an interpenetrating polymer network is provided, the interpenetrating polymer network derived from a first resin of Formulas (IA) or (IB) and a second resin of Formulas (IA) or (IB), wherein the first and second resins are different.

In some embodiments, a co-polymer or an interpenetrating polymer network is provided, the co-polymer or the interpenetrating polymer network being derived from a resin of Formulas (IA) or (IB), and a second component that differs from the resin of Formulas (IA) or (IB). In some embodiments, the second component is selected from the group consisting of polyethylenes, polypropylenes, polybutylenes, low vinyl polybutadienes (predominantly 1,3 addition), high vinyl polybutadienes (significant 1,2 addition), polystyrenes, butadiene-styrene copolymers, SMA polymers, ABS polymers, polydicyclopentadienes, epoxies, polyurethanes, cyanate esters, poly(phenylene oxide), EPDM polymers, cyclic olefin copolymers (COC), polyimides, bismaleimides, phosphazenes, olefin-modified phosphazenes, acrylates, vinyl esters, polylactones, polycarbonates, polysulfones, polythioethers, polyetheretherketones (PEEK), polydimethylsiloxanes (PDMS), polyethylene terephthalates (PET), polybutylene terephthalates (PBT), and other commercially-available polymers. In some other embodiments, the second component is selected from the group consisting of styrene, divinylbenzene, 1,2-bis(vinylphenyl)ethane, vinylbenzyl ether compounds, vinyl ether compounds, allyl ether compounds, vinylphenyl monomers, vinyl monomers, allyl monomers, or derivatives of such components. Suitable components include, but are not limited to, vinyl-functionalized cyanate ester HTL-300 (available from Lonza Chemicals), low- and high-vinyl Ricon polybutadienes (Total/Cray Valley), butadiene-styrene Ricon copolymers (Total/Cray Valley), Sartomer acrylate monomers (Arkema), olefin-containing phosphazene SPV-100 (Otsuka Chemicals), bismaleimide BMPI-300 (Lonza Chemicals), bismaleimide Cycom 5250 (Cytec Solvay), bismaleimide BMI-1700 (Designer Molecules Inc.), bismaleimide BMI-3000 (Designer Molecules, Inc.), bismaleimide BMI-689 (Designer Molecules, Inc.), bismaleimide Homide 250 (HOS-Technik GmbH), bismaleimide BMI-2300 (Daiwakaskei Industry Co., LTD), bismaleimide BMI-TMH (Daiwakaskei Industry Co., LTD), bismaleimide Compimide 353A (Evonik), bismaleimide Compimide C796 (Evonik), methacrylate-functionalized polyphenylene ether SA9000 (Sabic, Saudi Basic Industries Corporation), functionalized phenylene ether oligomers OPE-2EA and OPE-2St (MGC, Mitsubishi Gas Company), polyimide PETI 330 (UBE Industries, Ltd), Vinyl-ester resins Advalite 35070-00 (Reichhold), epoxy resins Celloxide 8000 and Celloxide 2021P (Daicel) or Araldite MY 721 and GY 281 and GY 240 (Huntsman).

Resin compositions of the present disclosure can be used as-isolated, or in blends with other copolymers, adhesion agents, peroxides/crosslinking agents, antioxidants, flame retardants, diluents and other additives or fillers known in the art.

As will be appreciated by those of ordinary skill in the art, the resins disclosed herein may be blended with other polymers. Such other polymers may be reactive such that they are copolymerized with the resin compositions of the present disclosure to form random or block copolymers. Alternately such other polymers may be formed by alternate means such that an interpenetrating polymer network or polymer phase dispersion is formed. Such other polymers include but are not limited to polyethylenes, polypropylenes, polybutylenes, low vinyl polybutadienes (predominantly 1,3 addition), high vinyl polybutadienes (significant 1,2 addition), polystyrenes, butadiene-styrene copolymers, SMA polymers (styrene maleic anhydride polymers), ABS polymers (acrylonitrile butadiene styrene polymers), polydicyclopentadienes, epoxies, polyurethanes, cyanate esters, poly (phenylene oxide), EPDM polymers (polymers derived from ethylene propylene diene monomers), cyclic olefin copolymers (COC), polyimides, bismaleimides, phosphazenes, olefin-modified phosphazenes, acrylates, vinyl esters, polylactones, polycarbonates, polysulfones, polythioethers, polyetheretherketones (PEEK), polydimethylsiloxanes (PDMS), polyethylene terephthalates (PET), polybutylene terephthalates (PBT), and other commercially-available polymers. Such polymers may be optionally modified or functionalized as desired.

In some embodiments, the resins disclosed herein may be blended with an electrical property modifier. Examples of the electrical property modifier may include cyanate ester derived compounds and bismaleimide triazine copolymers. A cyanate ester derived compound broadly refers to a chemical substance generally based on a bisphenol or novolac derivative, in which the hydrogen atom of at least one hydroxyl group of the bisphenol or novolac derivative is substituted by a cyanide group. Therefore, a cyanate ester derived compound generally has an —OCN group. In some implementations, a cyanate ester derived compound may refer to, without limitation, 4,4-ethylidenebisphenylene cyanate, 4,4-dicyanatodiphenyl, 2,2-bis(4-cyanatophenyl) propane, bis(4-cyanato-3,5-dimethylphenyl)methane, bis(4-cyanatophenyl)thioether, bis(4-cyanatophenyl)ether, prepolymer of bisphenol A dicyanate in methyl ethyl ketone, 1,1-bis(4-cyanatophenyl)ethane, 1,1-bis(4-cyanatophenyl) methane, 1,3-bis(4-cyanatophenyl-1-(methylethylidene)) benzene, bis(4-cyanatophenyl)ether, bis(4-cyanatophenyl)-2,2-butane, 1,3-bis[2-(4-cyanato phenyl)propyl]benzene, tris(4-cyanatophenyl)ethane, cyanated novolac, and cyanated phenoldicyclopentadiene adduct.

Resins of the present disclosure may be blended with various additives and adhesion agents to improve resin adhesion and compatibility with reinforcement substrates such as glass, carbon or aramid fibers. Suitable adhesion promoting additives include but are not limited to maleic anhydride, styrene maleic anhydrides, functionalized trialkoxysilanes, maleic anhydride-grafted polyolefins, as well as other polymers previously detailed in this disclosure which are capable of improved substrate adhesion.

Resin compositions of the present disclosure may be cured into a solid material by self-polymerization reactions at elevated temperatures, or by action of added radical initiators. Suitable radical initiators include but are not limited to dialkyl peroxides, diacyl peroxides, and azo compounds. Particularly suitable radical initiators include dicumyl peroxide and 2,5-Dimethyl-2,5-di-(tert-butylperoxy)hexyne-3 (Trigonox 145-E85). Radical initiators may be added at any level suitable to effect sufficient polymerization, ranging from ppm levels to 3 wt % depending on initiator used. If a radical initiator is used, it may be used in an amount ranging from about 0.5% to about 1.5% by weight of the composition.

Resin compositions of the present disclosure can be cured into a solid material at temperatures ranging from between about 120° C. to about 200° C. for between about 30 minutes and about 240 minutes. In some embodiments, the resin compositions may be cured into a solid material at temperatures ranging from between about 150° C. to about 175° C. for between about 60 minutes and about 180 minutes. The disclosure can then optionally be heated to higher temperatures for additional polymer curing as desired. In some embodiments, the resins of this disclosure, when fully cured, generate solid thermoset materials that possess glass transition temperatures (Tg) greater than 100° C. In some embodiments, the resins of this disclosure, when fully cured, generate solid thermoset materials that possess glass transition temperatures (Tg) greater than 150° C. In some embodiments, the resins of this disclosure, when fully cured, generate solid thermoset materials that possess glass transition temperatures (Tg) greater than 200° C. In some embodiments, the resins of this disclosure, when fully cured, generate solid thermoset materials that possess glass transition temperatures (Tg) ranging from about 100° C. to about 400° C. In yet other embodiments, the resins of this disclosure, when fully cured, generate solid thermoset materials that possess glass transition temperatures (Tg) ranging from about 125° C. to about 400° C. In yet other embodiments, the resins of this disclosure, when fully cured, generate solid thermoset materials that possess glass transition temperatures (Tg) ranging from about 175° C. to about 400° C.

Mechanical properties of the polymerized resin compositions of the present disclosure may be modified by incorporation of crosslinking agents. Such crosslinking agents include but are not limited to triallyl cyanurate, triallyl isocyanurate, polybutadiene dimethacrylates, polybutadiene diacrylates, divinylbenzene, 1,2-bis(vinylphenyl)ethane, vinylbenzyl ether compounds, vinyl ether compounds, allyl ether compounds, vinylphenyl monomers, vinyl monomers, allyl monomers, and similar compounds containing two or more carbon-carbon bond forming moieties per molecule.

Resin compositions of the present disclosure may be blended with solvents prior to polymerization, if desired, for certain applications. Any solvent known by one with skill in the art to be useful in conjunction with resin composition can be used. Particularly useful solvents include methyl ethyl ketone (MEK), xylene, toluene, DMF, and mixtures thereof. In some embodiments, the solvents are selected from MEK or toluene. When used, solvents are present in the resin composition in the amount ranging from between about 1% to about 99% by weight of the composition. In other embodiments, solvents are present in the resin composition in an amount ranging from between about 10% and about 60% by weight of the composition. In other embodiments, solvents are present in the resin composition in an amount ranging from between about 15% and about 30% by weight of the composition. In yet other embodiments, solvents are present in the resin composition in an amount ranging from between about 20% to about 25% by weight of the composition. Such solvent-blended resin compositions of the present disclosure are most useful for production of prepreg-style reinforcement layers.

The thermosetting resin compositions of the present disclosure may additionally be formulated with other standard antioxidants, flame retardants, fillers, diluents, stabilizers, processing aids and other additives as are commonly used in such applications. Such additives include, but are not limited to, phenolic antioxidants, dielectric fillers and commercial flame retardants. Most commercial flame retardants are suitable for use with resins of the present disclosure. Suitable flame retardants also include phosphazenes and olefin-modified phosphazenes. Also, resin laminates made from resin composition can be made V0 without halogenated flame retardant using reactive phosphorus flame retardants such as (vinyl or other radical-reactive FR), as well as non-reactive phosphorus flame retardants.

The thermosetting resin compositions of the subject disclosure may also be used to provide prepregs with and without tack. The compositions are particularly useful in preparation of high Tg laminates having ultra-low dielectric constants and ultra-low dielectric loss. These electrical properties help solve signal speed and signal integrity problems encountered with high-speed analog and digital circuitry applications. The thermosetting resin compositions of the subject disclosure are useful for making prepregs in a continuous process with and without solvent. The viscosity of the inventive compositions can be adjusted for hot/melt prepreg and present substantial cost savings for prepreg production. Prepregs are generally manufactured using a reinforcement material including but not limited to woven glass, carbon, Kevlar, spectra, aramid or quartz fibers. The thermosetting resin composition of the present disclosure may also be coated directly to any polymeric film for build-up PCB. Thermosetting resin compositions of the present disclosure may also be directly coated to copper using slot-die or other related coating techniques for resin-coated copper (RCC). The prepreg materials made from thermosetting resins of the present disclosure can also be converted to laminates. The lamination process typically follows the stack-up of one or more prepreg layers between one or more sheets of conductive foil such as copper foil. This process is often described as copper-clad laminates (CCL) and is generally well-known to persons with ordinary skill in the art. Pressure and temperature applied to the prepreg stack result in the formation of laminates. The laminates produced from the present disclosure exhibit high Tg. It is also possible to generate compositions of the present disclosure that produce laminates of moderate Tg (>150° C.) with considerable flexibility. Flexible laminates are very useful for various bendable electronic devices. Thermosetting resins of the present disclosure with sufficiently low viscosities may also be used for vacuum infusion applications, where reinforcement materials as previously defined are impregnated with resin formulations of the present disclosure by action of vacuum pressure. Resins of the present disclosure with sufficiently low viscosities may be used in solvent-less or environmentally friendly manufacturing techniques for various applications. Resins of the present disclosure may also be used in 3D printing applications, including continuous liquid interface printing (CLIP) and stereolithography (SLA) applications.

Such combinations allow for improved surface adhesion performance in coatings, adhesives, composites and laminates.

Resins of Formulas (IA) or (IB) may additionally be used as additives, reactive diluents, or copolymers for commercial polymers used in electronic applications, providing improvements in resin viscosity and dielectric properties. In some embodiments, resins of Formulas (IA) or (IB) may be combined with resins based on cyanate esters, epoxies, bismaleimides, or polyolefins to generate blends with improved manufacturing properties, mechanical performance, or electrical performance.

Kits

In another aspect of the present disclosure are kits comprising any of the resins, polymers, blends, etc. disclosed herein. In some embodiments, the resins, polymers, blends, etc. are mixed with a suitable solvent. In some embodiments, the kits comprise multiple resins, polymers, blends, etc., where each of the resins, polymers, blends, etc. are provided in a separate container. In some embodiments, the kits include a resin and other reactants, reagents, or solvents. In some embodiments, the kits further comprise instructions.

For example, a kit may include a resin of any of Formulas (IA) or (IB) and also may include a bis-maleimide, such that the resin and the bis-maleimide may be reacted to form a product. Any bis-maleimides may be included in a kit, including any of those recited herein. In some embodiments, the kit includes a bis-maleimide is selected from the group consisting of 1,6'-bismaleimide-(2,2,4-trimethyl)hexane, 4,4'-Diphenylmethanebismaleimide, Polyphenylmethanebismaleimide, N,N'-(4-methyl-m-phenylene)-bismaleimide, N,N'-m-phenylenebismaleimide, bisphenol A diphenyl ether bismaleimide, 3,3'-dimethyl-5,5'-diethyl-4,4'-diphenylmethane bismaleimide, N,N'-[Methylenebis(2,6-diethyl-4,1-phenylene)]bis(maleimide, N,N'-[Methylenebis(2-isopropyl-6-methyl-4,1-phenylene)]bis(maleimide), 1,2-bis(maleimido)ethane, 1,4-bis(maleimido)butane, and 1,6-bis(maleimido)hexane.

In some embodiments, a kit may include a resin of any of Formulas (IA) or (IB) and also may include a crosslinking agent, such as a crosslinking agent selected from the group consisting of triallyl cyanurate, triallyl isocyanurate, polybutadiene dimethacrylates, polybutadiene diacrylates, divinylbenzene, 1,2-bis(vinylphenyl)ethane, vinylbenzyl ether compounds, vinyl ether compounds, allyl ether compounds, vinylphenyl monomers, vinyl monomers, and allyl monomers.

Applications

The resins, reaction products, blends, polymers, compositions, etc. described herein may be utilized in any suitable application. For example, the resins, reaction products, blends, polymers, compositions, etc. may be used as a substrate onto which other materials may be applied. In some embodiments, resins, reaction products, blends, polymers, compositions, etc. may be applied as films onto the surface of another substrate or a laminate may be produced from the resins, reaction products, blends, polymers, compositions, etc. disclosed herein.

In some embodiments, the resins, reaction products, blends, polymers, compositions, etc. disclosed herein may be used in the manufacture of printed circuit boards or for general use in any electronic device. In other embodiments, resins, reaction products, blends, polymers, compositions, etc. disclosed herein may be used in radomes, antennas (e.g. cellular phone antennas, satellite phone antennas, antennas for 5G communication devices, etc.), or in radar structures. In yet other embodiments, the resins, reaction products, blends, polymers, compositions, etc. disclosed herein may be used as part of an under fill adhesive composition. In further embodiments, the resins, reaction products, blends, polymers, compositions, etc. disclosed herein may be used in cellular base stations, wireless base stations, modems, and routers. In yet other embodiments, the resins, reaction products, blends, polymers, compositions, etc. disclosed herein may be used in radio frequency identification tags and other sensors. In yet other embodiments, the resins, reaction products, blends, polymers, compositions, etc. disclosed herein may be used in microwave communication systems. In yet other embodiments, the resins, reaction products, blends, polymers, compositions, etc. disclosed herein may be used communications and network servers. In yet other embodiments, the resins, reaction products, blends, polymers, compositions, etc. disclosed herein may be used in backplanes.

EXAMPLES

Materials: Sodium hydride (60% dispersion in mineral oil) was obtained from Sigma-Aldrich. Cyclopentadiene was isolated by thermal cracking of dicyclopentadiene (Ultrene 97 from Cymetech Corporation) at temperatures of 150-180° C. per literature methods. Vinylbenzyl chloride was obtained from DOW Chemical Company and used as received. Allyl chloride, 1,3-dibromopropane, 1,6-dichlorohexane, divinylbenzene, and glycidyl methacrylate were obtained from Sigma Aldrich and used as received. Maleic anhydride was obtained from Huntsman and used as-received. Methyl tributyl ammonium chloride was obtained from Sachem, Inc. Trigonox 145-E85 was obtained from Akzo Nobel. HTL-300 was obtained from Lonza. Novocure 200 was obtained from Novoset LLC. Ricon 153 and Ricon 100 were obtained from Total/Cray Valley. Sartomer CN-301 and Sartomer CN-303 were obtained from Arkema. Noryl SA-9000 was obtained from Sabic. BMPI-300 was obtained from Cyalume Specialty Products. BMI-3000 and BMI-689 were obtained from Designer Molecules, Inc. BMI-TMH and BMI-2300 were obtained from Daiwakasei Industry Co. 4,4'-diphenylmethanebismaleimide was obtained from Chem-Impex International. Homide 250 was obtained from HOS-Technik. TAICROS, Compimide 353A, Compimide C796, Dynasylan MEMO, and Dynasylan VTEO were obtained from Evonik.

Synthesis Example 1

In a 500 mL round-bottomed flask, 16.7 g sodium hydride dispersion (60% in mineral oil, 1.1 equivalents active sodium hydride) was washed with hexanes to remove the mineral oil and then suspended in 250 mL of tetrahydrofuran (THF). The reaction vessel was filled with inert atmosphere and cooled to 0° C. Freshly-cracked cyclopentadiene (26.0 g, 1.0 equivalent) was added portion wise with vigorous stirring, generating hydrogen gas that was vented. After all cyclopentadiene was added, the reaction was heated to mild reflux (60° C.) and vinylbenzyl chloride (52.0 g, 0.9 eq) was added portion-wise, after which the reaction was maintained at reflux for an additional 30 minutes before addition of water (50 g) to eliminate any unreacted hydride. The THF solvent was removed by rotary evaporation, yielding an organic/aqueous mixture. The organic phase was diluted with a mix of xylenes and hexane (50 vol %) and washed several times with aqueous HCl (10 wt %) solution and water before isolation of the organic phase. The organic phase was dried over sodium sulfate and the solvents were removed by vacuum distillation, yielding a product mixture featuring cyclopentadienes substituted with one or more vinylbenzyl substituents.

Synthesis Example 2

Following the procedure in Example 1, NaH (2.2 eq) was combined with freshly-cracked cyclopentadiene (1.0 eq) and vinylbenzyl chloride (2.0 eq) to yield a product mixture featuring cyclopentadienes substituted with an average of two vinylbenzyl substituents.

Synthesis Example 3

Following the procedure in Example 1, NaH (2.2 eq) was combined with freshly-cracked cyclopentadiene (2.0 eq) and 1,3-dibromopropane (1.0 eq) to yield a product mixture featuring an average of two cyclopentadienes connected by a propyl hydrocarbon.

Synthesis Example 4

Following the procedure in Example 1, NaH (2.2 eq) was combined with freshly-cracked cyclopentadiene (2.0 eq) and 1,6-dichlorohexane (1.0 eq) to yield a product mixture featuring an average of two cyclopentadienes connected by a hexyl hydrocarbon.

Synthesis Example 5

Following a modified procedure, cyclopentadiene compounds (1.0 eq) as described in Synthesis Example 4 were added portion wise to a suspension of NaH (2.2 eq) in THF with vigorous stirring, generating hydrogen gas that was vented. After all cyclopentadiene compounds were added, the reaction was heated to mild reflux (60° C.) and vinylbenzyl chloride (2.0 eq) was added portion-wise, after which the reaction was maintained at reflux for an additional 30 minutes before addition of water (50 g) to eliminate any unreacted hydride. Following workup as described in Synthesis Example 1, the reaction yielded a product mixture featuring an average of two (vinylbenzyl)-functionalized cyclopentadienes connected by a hexyl hydrocarbon.

Synthesis Example 6

Following a modified procedure, NaH (4.4 eq) was combined with freshly-cracked cyclopentadiene (2.0 eq), and 1,6-dichlorohexane (1.0 eq), followed by addition of vinylbenzyl chloride (2.0 eq), after which the reaction was maintained at reflux for an additional 30 minutes before addition of water (50 g) to eliminate any unreacted hydride. Following workup as described in Synthesis Example 1, the reaction yielded a product mixture featuring an average of two (vinylbenzyl)-functionalized cyclopentadienes connected by a hexyl hydrocarbon.

Synthesis Example 7

Following a modified procedure, NaH (5.5 eq) was combined with freshly-cracked cyclopentadiene (2.0 eq), and 1,6-dichlorohexane (1.5 eq), followed by addition of vinylbenzyl chloride (2.0 eq). After addition, the reaction was maintained at reflux for an additional 30 minutes before addition of water (50 g) to eliminate any unreacted hydride. Following workup as described in Synthesis Example 1, the reaction yielded a product mixture featuring oligomers of (vinylbenzyl)-functionalized cyclopentadienes connected by hexyl hydrocarbons.

Synthesis Example 8

Following a modified procedure, NaH (4.4 eq) was combined with freshly-cracked cyclopentadiene (2.0 eq), and 1,6-dichlorohexane (1.0 eq), followed by addition of a mixture of vinylbenzyl chloride (1.0 eq) and allyl chloride (1.0 eq). After addition, the reaction was maintained at reflux for an additional 30 minutes before addition of water (50 g) to eliminate any unreacted hydride. Following workup as described in Synthesis Example 1, the reaction yielded a product mixture featuring a mixture of (vinylbenzyl)-functionalized cyclopentadienes and allyl-functionalized cyclopentadienes connected by hexyl hydrocarbons.

Synthesis Example 9

Following the procedure in Example 1, NaH (2.2 eq) was combined with freshly-cracked cyclopentadiene (1.0 eq) and a mixture of vinylbenzyl chloride (1.0 eq) and allyl chloride (1.0 eq) to yield a product mixture featuring cyclopentadienes substituted with an average of one vinylbenzyl substituent and one allyl substituent.

Synthesis Example 10

Following a modified procedure, NaH (4.4 eq) was combined with freshly-cracked cyclopentadiene (2.0 eq), and 1,6-dichlorohexane (1.0 eq), followed by addition of allyl chloride (2.0 eq). After addition, the reaction was maintained at reflux for an additional 30 minutes before addition of water (50 g) to eliminate any unreacted hydride. Following workup as described in Synthesis Example 1, the reaction yielded a product mixture featuring allyl-functionalized cyclopentadienes connected by hexyl hydrocarbons.

Synthesis Example 11

Following a modified procedure, NaH (5.5 eq) was combined with freshly-cracked cyclopentadiene (2.0 eq), and 1,6-dichlorohexane (1.5 eq), followed by addition of a mixture of vinylbenzyl chloride (1.0 eq) and allyl chloride (1.0 eq). After addition, the reaction was maintained at reflux for an additional 30 minutes before addition of water (50 g) to eliminate any unreacted hydride. Following workup as described in Synthesis Example 1, the reaction yielded a product mixture featuring oligomers of (vinylbenzyl)-functionalized cyclopentadienes and allyl-functionalized cyclopentadienes connected by hexyl hydrocarbons.

Synthesis Example 12

13.5 g of resin from Example 1 was dissolved in 10.0 g of dichloromethane solvent and combined with a solution of 1.5 g BMPI-300 (Cyalume Specialty Products) in an additional 10.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 13

11.25 g of resin from Example 1 was dissolved in 10.0 g of dichloromethane solvent and combined with a solution of 3.75 g BMPI-300 (Cyalume Specialty Products) in an additional 10.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 14

7.5 g of resin from Example 1 was dissolved in 10.0 g of dichloromethane solvent and combined with a solution of 7.5 g BMPI-300 (Cyalume Specialty Products) in an additional 10.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 15

13.5 g of resin from Example 1 was dissolved in 10.0 g of dichloromethane solvent and combined with a solution of 1.5 g maleic anhydride in an additional 10.0 g of dichloromethane solvent. The combined homogeneous solution was allowed to react at room temperature for 10 minutes, before removal of the dichloromethane by rotary evaporation at 50° C., yielding a product mixture featuring partially maleated resins of Example 1.

Synthesis Example 16

11.25 g of resin from Example 1 was combined with a solution of 3.75 g BMI-3000 (Designer Molecules Inc.) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 17

11.25 g of resin from Example 1 was combined with a solution of 3.75 g BMI-TMH (Daiwakasei Industry Co.) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 18

11.25 g of resin from Example 1 was combined with a solution of 3.75 g BMI-2300 (Daiwakasei Industry Co.) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 19

11.25 g of resin from Example 1 was combined with a solution of 3.75 g 4,4'-diphenylmethanebismaleimide (Chem-Impex International) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 20

11.25 g of resin from Example 1 was combined with a solution of 3.75 g Homide 250 bismaleimide resin (HOS-Technik) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 21

11.25 g of resin from Example 1 was combined with a solution of 3.75 g Compimide 353A bismaleimide resin (Evonik) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 22

11.25 g of resin from Example 1 was combined with a solution of 3.75 g Compimide C796 bismaleimide resin (Evonik) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 23

11.25 g of resin from Example 8 was combined with a solution of 3.75 g BMPI-300 (Cyalume Specialty Products) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 24

11.25 g of resin from Example 9 was combined with a solution of 3.75 g BMPI-300 (Cyalume Specialty Products) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 25

11.25 g of resin from Example 1 was combined with a solution of 3.75 g BMI 689 (Designer Molecules Inc.) in 15.0 g of dichloromethane solvent. The combined homogeneous solution was allowed to react at room temperature for 10 minutes, before removal of the dichloromethane by rotary evaporation at 50° C., yielding a product mixture featuring partial reaction between the two resins.

Synthesis Example 26

In a modified procedure, freshly-cracked cyclopentadiene (1.0 eq) was combined with vinylbenzyl chloride (1.0 eq), methyl tributyl ammonium chloride (0.05 eq), and 50 wt % KOH aqueous solution. The biphasic mixture was allowed to react under vigorous stirring for 4 hours at room temperature, after which the organic layer was separated from the aqueous base. The organic phase was diluted with a mix of xylenes and hexane (50 vol %) and washed several times with aqueous HCl (10 wt %) solution and water before isolation of the organic phase. The organic phase was dried over sodium sulfate and the solvents were removed by vacuum distillation, yielding a product mixture featuring cyclopentadienes substituted with one or more vinylbenzyl substituents.

Polymerization Examples

Polymerization 1: Thermal Polymerization of Example 1

10.0 g of resin from Example 1 was poured into a mold constructed of glass plate and a 1.6 mm-thick PTFE spacer and cured by oven ramp from 100-190° C. at a rate of 1° C./minute, followed by 1 hour of cure at 190° C. to generate a cured resin panel. Dielectric properties: Dk 2.63, Df 0.0017

Polymerization 2: Radical Polymerization of Example 1

10.0 g of resin from Example 1 was combined with 0.75 wt % Trigonox 145-E85 peroxide and cured in the same manner as Polymerization Example 1. Dielectric properties: Dk 2.65, Df 0.0036

Polymerization 3: Thermal Polymerization of Example 2

10.0 g of resin from Example 2 was cured in the same manner as Polymerization Example 1. Dielectric properties: Dk 2.68, Df 0.0019

Polymerization 4: Thermal Polymerization of Example 3

10.0 g of resin from Example 3 was cured in the same manner as Polymerization Example 1. Dielectric properties: Dk 2.31, Df 0.0024

Polymerization 5: Radical Polymerization of Example 3

10.0 g of resin from Example 3 was combined with 1.50 wt % Trigonox 145-E85 peroxide and cured in the same manner as Polymerization Example 1. Dielectric properties: Dk 2.36, Df 0.0028

Polymerization 6: Thermal Polymerization of Blends of Examples 2 and 3

10.0 g of resin were formed by blending 5.0 g of resin from Example 3 with 5.0 g of resin from Example 2. This blend was cured in the same manner as Polymerization Example 1. Dielectric properties: Dk 2.61, Df 0.0019

Polymerization 7: Thermal Polymerization of Example 4

10.0 g of resin from Example 4 was cured in the same manner as Polymerization Example 1. Dielectric properties: Dk 2.51, Df 0.011

Polymerization 8: Radical Polymerization of Example 4

10.0 g of resin from Example 4 was combined with 1.50 wt % Trigonox 145-E85 peroxide and cured in the same manner as Polymerization Example 1. Dielectric properties: Dk 2.53, Df 0.011

Polymerization 9: Thermal Polymerization of Example 6

10.0 g of resin from Example 6 was cured in the same manner as Polymerization Example 1. Dielectric properties: Dk 2.62, Df 0.0021

Polymerization 10: Thermal Polymerization of Example 7

10.0 g of resin from Example 7 was cured in the same manner as Polymerization Example 1.

Polymerization 11: Thermal Polymerization of Blends of Examples 1 and 6

10.0 g of resin were formed by blending 5.0 g of resin from Example 1 with 5.0 g of resin from Example 6. This blend was cured in the same manner as Polymerization Example 1. Dielectric properties: Dk 2.64, Df 0.0018

Polymerization 12: Thermal Polymerization of Example 8

10.0 g of resin from Example 8 was cured in the same manner as Polymerization Example 1. Dielectric properties: Dk 2.53, Df 0.0018

Polymerization 13: Thermal Polymerization of Example 9

10.0 g of resin from Example 9 was cured in the same manner as Polymerization Example 1. Dielectric properties: Dk 2.62, Df 0.0015

Polymerization 14: Thermal Polymerization of Blends of Examples 1 and 10

10.0 g of resin were formed by blending 5.0 g of resin from Example 1 with 5.0 g of resin from Example 10. This blend was cured in the same manner as Polymerization Example 1. Dielectric properties: Dk 2.52, Df 0.0022

Polymerization 15: Thermal Polymerization of Blends of Examples 6 and 10

10.0 g of resin were formed by blending 5.0 g of resin from Example 6 with 5.0 g of resin from Example 10. This blend was cured in the same manner as Polymerization Example 1. Dielectric properties: Dk 2.48, Df 0.0026

Polymerization 16: Thermal Polymerization of Blend of Example 1 with High-Vinyl Cyanate Ester Resin 10.0 g of resin were formed by blending 9.0 g of resin from Example 1 with 1.0 g of vinyl-functionalized cyanate ester resin HTL-300. This blend was cured in the same manner as Polymerization Example 1. Dielectric properties: Dk 2.65, Df 0.0028

Polymerization 17: Thermal Polymerization of Blend of Example 1 with Catalyzed High-Vinyl Cyanate Ester Resin 10.0 g of resin were formed by blending 9.0 g of resin from Example 1 with 1.0 g of vinyl-functionalized cyanate ester resin HTL-300 that had been catalyzed with Novocure 200. This blend was poured into a mold constructed of glass plate and a 1.6 mm-thick PTFE spacer and cured by oven ramp from 75-190° C. at a rate of 1° C./minute, 1 hour of cure at 190° C., secondary ramp of 190-230° C. at a rate of 1° C./min, 2 hours of cure at 230° C., followed by oven ramp from 230-250° C. at a rate of 1° C./min, with final post-cure at 250° C. for one hour to generate a cured resin panel. Dielectric properties: Dk 2.67, Df 0.0034

Polymerization 18: Thermal Polymerization of Blend of Example 1 with Catalyzed High-Vinyl Cyanate Ester Resin 10.0 g of resin were formed by blending 5.0 g of resin from Example 1 with 5.0 g of vinyl-functionalized cyanate ester resin HTL-300 that had been catalyzed with Novocure 200. This blend was poured into a mold constructed of glass plate and a 1.6 mm-thick PTFE spacer and cured by oven ramp from 75-190° C. at a rate of 1° C./minute, 1 hour of cure at 190° C., secondary ramp of 190-230° C. at a rate of 1° C./min, 2 hours of cure at 230° C., followed by oven ramp from 230-250° C. at a rate of 1° C./min, with final post-cure at 250° C. for one hour to generate a cured resin panel. Dielectric properties: Dk 2.80, Df 0.0085

Polymerization 19: Thermal Polymerization of Blend of Example 1 with Catalyzed High-Vinyl Cyanate Ester Resin 10.0 g of resin were formed by blending 0.54 g of resin from Example 1 with 9.33 g of a cyanate ester containing olefinic groups (HTL-300) and 0.13 g of Novocure 200. This blend was placed in an oven and the temperature ramp 1° C./min from room temperature to 160° C. and held for 1 hour at 160° C. after which the temperature was ramped at 1° C./min to 190° C. and held for 2 hours at 190° C. Dielectric properties: Dk 2.82, Df 0.0051

Polymerization 20: Thermal Polymerization of Blend of Example 1 with Catalyzed High-Vinyl Cyanate Ester Resin 10.0 g of resin were formed by blending 2.00 g of resin from Example 1 with 7.86 g of a cyanate ester containing olefinic groups (HTL-300) and 0.14 g of Novocure 200. This blend was placed in an oven and the temperature ramp 1° C./min from room temperature to 160° C. and held for 1 hour at 160° C. after which the temperature was ramped at 1° C./min to 190° C. and held for 2 hours at 190° C. Dielectric properties: Dk 2.81, Df 0.0054

Polymerization 21: Thermal Polymerization of Blend of Example 1 with Catalyzed High-Vinyl Cyanate Ester Resin 10.0 g of resin were formed by blending 2.99 g of resin from Example 1 with 6.88 g of a cyanate ester containing olefinic groups (HTL-300) and 0.13 g of Novocure 200. This blend was placed in an oven and the temperature ramp 1° C./min from room temperature to 160° C. and held for 1 hour at 160° C. after which the temperature was ramped at 1° C./min to 190° C. and held for 2 hours at 190° C. Dielectric properties: Dk 2.79, Df 0.0057

Polymerization 22: Thermal Polymerization of Blend of Example 1 with High-Vinyl Polybutadiene Resin 10.0 g of resin were formed by blending 9.0 g of resin from Example 1 with 1.0 g of vinyl-functionalized polybutadiene resin Ricon 153. This blend was cured in the same manner as Polymerization Example 1. Dielectric properties: Dk 2.53, Df 0.0014

Polymerization 23: Thermal Polymerization of Blend of Example 1 with High-Vinyl Polybutadiene Resin 10.0 g of resin were formed by blending 7.5 g of resin from Example 1 with 2.5 g of vinyl-functionalized polybutadiene resin Ricon 153. This blend was cured in the same manner as Polymerization Example 1. Dielectric properties: Dk 2.48, Df 0.0018

Polymerization 24: Thermal Polymerization of Blend of Example 1 with Butadiene-Styrene Copolymer Resin 10.0 g of resin were formed by blending 9.0 g of resin from Example 1 with 1.0 g of vinyl-functionalized butadiene-styrene copolymer resin Ricon 100. This blend was cured in the same manner as Polymerization Example 1. Dielectric properties: Dk 2.60, Df 0.0014

Polymerization 25: Thermal Polymerization of Blend of Example 1 with Hexanediol Diacrylate 10.0 g of resin were formed by blending 9.0 g of resin from Example 1 with 1.0 g of hexanediol diacrylate Sartomer CN-301. This blend was cured in the same manner as Polymerization Example 1. Dielectric properties: Dk 2.64, Df 0.0037

Polymerization 26: Thermal Polymerization of Blend of Example 1 with Polybutadiene Dimethacrylate 10.0 g of resin were formed by blending 9.0 g of resin from Example 1 with 1.0 g of polybutadiene dimethacrylate Sartomer CN-303. This blend was cured in the same manner as Polymerization Example 1. Dielectric properties: Dk 2.64, Df 0.0028

Polymerization 27: Thermal Polymerization of Blend of Example 1 with Phosphazene 10.0 g of resin were formed by blending 7.5 g of resin from Example 1 with 2.5 g of an olefin containing phosphazene (SPV-100). This blend was placed in an oven and the temperature ramp 1° C./min from room temperature to 160° C. and held for 1 hour at 160° C. after which the temperature was ramped at 1° C./min to 190° C. and held for 2 hours at 190° C. Dielectric properties: Dk 2.95, Df 0.0032

Polymerization 28: Thermal Polymerization of Blend of Example 1 with Phosphazene 10.0 g of resin were formed by blending 5.0 g of resin from Example 1 with 5.0 g of an olefin containing phosphazene (SPV-100). This blend was placed in an oven and the temperature ramp 1° C./min from room temperature to 160° C. and held for 1 hour at 160° C. after which the temperature was ramped at 1° C./min to 190° C. and held for 2 hours at 190° C. Dielectric properties: Dk 2.92, Df 0.0058

Polymerization 29: Thermal Polymerization of Blend of Example 1 with Hydroxylated Polybutadiene Acrylic Ester 10.0 g of resin were formed by blending 5.02 g of resin from Example 1 with 4.98 g of hydroxylated polybutadiene Acrylic ester (HBAE). This blend was placed in an oven and the temperature ramp 1° C./min from room temperature to 160° C. and held for 1 hour at 160° C. after which the temperature was ramped at 1° C./min to 190° C. and held for 2 hours at 190° C. Dielectric properties: Dk 2.60, Df 0.0040

Polymerization 30: Thermal Polymerization of Blend of Example 1 with Methacryl-PPE 10.0 g of resin were formed by blending 5.15 g of resin from Example 1 with 4.85 g of methacrylated polyphenylether resin (SA-9000) in 5 mL of DCM. This blend was drawn into a thin layer on a glass sheet with a draw knife and the solvent allowed to evaporate. The thin layer was sandwiched between glass sheets and placed in an oven and the temperature ramped 1° C./min from room temperature to 160° C. and held for 1 hour at 160° C. after which the temperature was ramped at 1° C./min to 190° C. and held for 2 hours at 190° C. Dielectric properties: Dk 1.71, Df 0.0036

Polymerization 31: Thermal Polymerization of Blend of Example 1 with Epoxies 10.0 g of resin were formed by blending 3.62 g of resin from Example 1 with 1.97 g glycidyl methacrylate and 4.42 g of dicyclopentadiene-phenol epoxy This blend was placed in an oven and the temperature ramp 1° C./min from room temperature to 160° C. and held for 1 hour at 160° C. after which the temperature was ramped at 1° C./min to 190° C. and held for 2 hours at 190° C. Dielectric properties: Dk 3.0, Df 0.051

Polymerization 32: Thermal Polymerization of Blend of Example 1 with Bismaleimide 10.0 g of resin were formed by blending 5.34 g of resin from Example 1 with 4.66 g of bismaleimide resin (BMPI-300) in 5 mL of DCM. This blend drawn into a thin layer on a glass sheet with a draw knife and the solvent allowed to evaporate. The thin layer was sandwiched between glass sheets and placed in an oven and the temperature ramped 1° C./min from room temperature to 160° C. and held for 1 hour at 160° C. after which the temperature was ramped at 1° C./min to 190° C. and held for 2 hours at 190° C. Dielectric properties: Dk 2.53, Df 0.0023

Polymerization 33: Thermal Polymerization of Example 12

10.0 g of resin from Example 12 was cured in the same manner as Polymerization Example 1. Dielectric properties: Dk 2.68, Df 0.0012

Polymerization 34: Thermal Polymerization of Example 13

10.0 g of resin from Example 13 was cured in the same manner as Polymerization Example 1. Dielectric properties: Dk 2.70, Df 0.0017

Polymerization 35: Thermal Polymerization of Example 15

10.0 g of resin from Example 15 was cured in the same manner as Polymerization Example 1. Dielectric properties: Dk 2.79, Df 0.0055

Polymerization 36: Thermal Polymerization of Blend of Example 1 with Divinylbenzene 10.0 g of resin were formed by blending 9.5 g of resin from Example 1 with 0.5 g of divinylbenzene (DVB). This blend was cured in the same manner as Polymerization Example 1. Dielectric properties: Dk 2.64, Df 0.0016

Polymerization 37: Thermal Polymerization of Blend of Example 1 with Triallylisocyanurate 10.0 g of resin were formed by blending 9.5 g of resin from Example 1 with 0.5 g of triallylisocyanurate (Evonik TAICROS). This blend was cured in the same manner as Polymerization Example 1. Dielectric properties: Dk 2.67, Df 0.0016

Polymerization 38: Thermal Polymerization of Blend of Example 1 with Triallylisocyanurate 10.0 g of resin were formed by blending 8.8 g of resin from Example 1 with 1.2 g of triallylisocyanurate (Evonik TAICROS). This blend was cured in the same manner as Polymerization Example 1. Dielectric properties: Dk 2.65, Df 0.0014

Polymerization 39: Thermal Polymerization of Blend of Example 1 with Triallylisocyanurate 10.0 g of resin were formed by blending 7.5 g of resin from Example 1 with 2.5 g of triallylisocyanurate (Evonik TAICROS). This blend was cured in the same manner as Polymerization Example 1. Dielectric properties: Dk 2.69, Df 0.0014

Polymerization 40: Thermal Polymerization of Blend of Example 1 with Vinylsilane 10.0 g of resin were formed by blending 9.0 g of resin from Example 1 with 1.0 g of triethoxyvinyl silane (Evonik Dynasylan VTEO). This blend was cured in the same manner as Polymerization Example 1. Dielectric properties: Dk 2.68, Df 0.0055

Polymerization 41: Thermal Polymerization of Blend of Example 1 with Methacrylsilane 10.0 g of resin were formed by blending 9.0 g of resin from Example 1 with 1.0 g of 3-trimethoxysilylpropyl methacrylate (Evonik Dynasylan MEMO). This blend was cured in the same manner as Polymerization Example 1. Dielectric properties: Dk 2.74, Df 0.0058

Polymerization 42: Thermal Polymerization of Example 16

10.0 g of resin from Example 16 was cured in the same manner as Polymerization Example 1. Dielectric properties: Dk 2.64, Df 0.0012

Polymerization 43: Thermal Polymerization of Example 17

10.0 g of resin from Example 17 was cured in the same manner as Polymerization Example 1. Dielectric properties: Dk 2.73, Df 0.0028

Polymerization 44: Thermal Polymerization of Example 18

10.0 g of resin from Example 18 was cured in the same manner as Polymerization Example 1. Dielectric properties: Dk 2.25, Df 0.0025

Polymerization 45: Thermal Polymerization of Example 19

10.0 g of resin from Example 19 was cured in the same manner as Polymerization Example 1. Dielectric properties: Dk 2.33, Df 0.0028

Polymerization 46: Thermal Polymerization of Example 21

10.0 g of resin from Example 21 was cured in the same manner as Polymerization Example 1. Dielectric properties: Dk 2.81, Df 0.0031

Polymerization 47: Thermal Polymerization of Example 22

10.0 g of resin from Example 22 was cured in the same manner as Polymerization Example 1. Dielectric properties: Dk 2.62, Df 0.0040

Polymerization 48: Thermal Polymerization of Blend of Example 1 with Bismaleimide 15.0 g of resin were formed by blending 11.25 g of resin from Example 1 with 3.75 g of 4,4'-diphenylmethanebismaleimide (Chem-Impex International). This blend was cured in the same manner as Polymerization Example 1. Dielectric properties: Dk 2.76, Df 0.0016

Polymerization 49: Thermal Polymerization of Example 24

10.0 g of resin from Example 24 was cured in the same manner as Polymerization Example 1. Dielectric properties: Dk 2.68, Df 0.0021

Polymerization 50: Thermal Polymerization of Example 25

10.0 g of resin from Example 23 was cured in the same manner as Polymerization Example 1. Dielectric properties: Dk 2.64, Df 0.0014

Polymerization 51: Thermal Polymerization of Blend of Example 8 with Bismaleimide 10.0 g of resin were formed by blending 7.50 g of resin from Example 8 with 2.50 g of BMPI-300 (Cyalume Specialty Products). This blend was cured in the same manner as Polymerization Example 1. Dielectric properties: Dk 2.42, Df 0.0016

Polymerization 52: Thermal Polymerization of Blend of Example 10 with Bismaleimide 10.0 g of resin were formed by blending 7.50 g of resin from Example 10 with 2.50 g of BMPI-300 (Cyalume Specialty Products). This blend was cured in the same manner as Polymerization Example 1. Dielectric properties: Dk 2.04, Df 0.0024

ADDITIONAL EMBODIMENTS

1. A resin having a structure defined by Formula (VI):

$$(A)_m \mid X-(Z)_n-(B)_q,$$ (VI)

wherein
X is cyclopentadiene;
B is H;
$(Z)_n$ is a bond;
m is ranges from 1 to 5;
and A has the structure defined by Formula (IIC):

$$\left\{ \begin{bmatrix} R^a \\ | \\ C \\ | \\ R^b \end{bmatrix}_t \right\} - (T)_u - (Y)_z,$$ (IIC)

wherein $R^a$ and $R^b$ are independently selected from H, F, a $C_1$ to $C_{10}$ linear or cyclic, branched or straight chain aliphatic group; T is $-CH_2-$, -phenyl, or $-CH_2$-phenyl; Y is H, $-CH_3$, $-CH=CH_2$, $-CH=CH-CH_3$, or alkyne; t is 0 or an integer ranging from 1 to 20; u is 0 or 1; z is an integer ranging from 1 to 5.

2. The resin of embodiment 1, wherein t is 1; and $R^a$ and $R^b$ are each H.

3. The resin of embodiment 2, wherein Y is $-CH=CH_2$.

4. The resin of embodiment 1, wherein m is 2, and a first A group comprises a vinyl benzyl moiety; and wherein a second A group is $-CH_2-CH=CH_2$.

5. The resin of embodiment 1, wherein the resin has the structure

[structure showing cyclopentadiene linked via $CH_2$ to phenyl with $CH_2$ vinyl group]

6. A resin having a structure defined by Formula (VII):

$$(A)_m-\underset{}{\bigcirc}-(Z)_n-\underset{}{\bigcirc}-(A)_s,$$ (VII)

wherein
Z has the structure defined by Formula (IIIA):

$$\left\{ \begin{bmatrix} R^e \\ | \\ C \\ | \\ R^f \end{bmatrix}_y \right\},$$ (IIIA)

wherein
$R^e$ and $R^f$ are independently selected from H, F, or a straight chain or branched alkyl group having between 1 and 6 carbon atoms; and
y is an integer ranging from between 1 and about 20;
m and s are independently an integer ranging from between 1 and about 5;
A is H or a moiety having a structure defined by Formula (IIC):

$$\left\{ \begin{bmatrix} R^a \\ | \\ C \\ | \\ R^b \end{bmatrix}_t \right\} - (T)_u - (Y)_z,$$ (IIC)

wherein $R^a$ and $R^b$ are independently selected from H, F, a $C_1$ to $C_{10}$ linear or cyclic, branched or straight chain aliphatic group;
T is $-CH_2-$, -phenyl, or $-CH_2$-phenyl;
Y is H, $-CH_3$, $-CH=CH_2$, $-CH=CH-CH_3$, or alkyne;
t is 0 or an integer ranging from 1 to 20;
u is 0 or 1; and
z is an integer ranging from 1 to 5.

7. The resin of embodiment 6, wherein n is 1, and $R^e$ and $R^f$ are each H.

8. The resin of embodiment 6, wherein A is H.

9. The resin of embodiment 8, wherein y is 6.

10. The resin of embodiment 8, wherein y is 3.

11. The resin of embodiment 6, wherein the resin has the structure selected from the group consisting of:

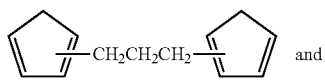 and

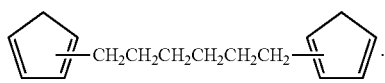.

12. The resin of embodiment 6, wherein at least one of $(A)_m$ or $(A)_s$ comprise a moiety having the structure defined by Formula (IIC):

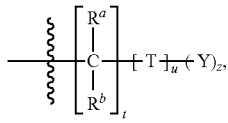 (IIC)

and $R^a$ and $R^b$ are each H.

13. The resin of embodiment 12, wherein Y is —CH=CH$_2$.

14. The resin of embodiment 13, $R^e$ and $R^f$ are each H.

15. The resin of embodiment 14, wherein y is 6.

16. The resin of embodiment 14, wherein m is 1 and s is 0.

17. The resin of embodiment 12, wherein the resin has the structure:

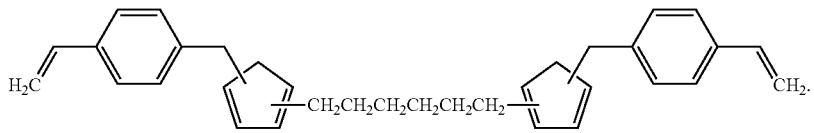

18. The resin of embodiment 6, wherein $(A)_m$ and $(A)_s$ each comprise a different moiety having Formula (IIC):

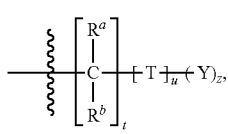 (IIC)

19. The resin of embodiment 18, wherein for $(A)_m$, t is 1 and T is phenyl; and for (A), t is 1 and u is 0.

20. The resin of embodiment 18, wherein for $(A)_m$, t is 1; T is phenyl, and Y is —CH=CH$_2$; and for (A), t is 1, u is 0, and Y is —CH=CH$_2$.

21. The resin of embodiment 18, wherein the resin has the structure:

22. A resin having a structure defined by Formula (IVB):

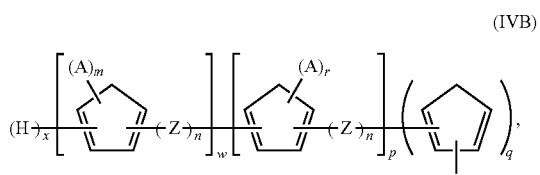 (IVB)

wherein each A is independently H, F, or a saturated or unsaturated, straight-chain or branched, linear or cyclic, substituted or unsubstituted, aliphatic group having between 1 and 40 carbon atoms;

Z is a straight-chain or branched, substituted or unsubstituted, aliphatic group having between 1 and 20 carbon atoms, or when n is 0, Z is a bond;

m is an integer ranging from 1 to 5;

n is 0 or 1;

p is 0 or an integer ranging from 1 to 150;

q is 0 or 1;

r is an integer ranging from 1 to 4;

s is an integer ranging from 1 to 5;

w is 0 or an integer ranging from 1 to 150; and x is 0 or 1.

23. The resin of embodiment 22, wherein each of $(A)_m$ and $(A)_s$ are different.

24. The resin of embodiment 23, wherein $(A)_m$ comprises a vinyl benzyl group; and wherein (A), is —CH$_2$—CH=CH$_2$.

25. The resin of embodiment 24, wherein $(A)_m$ is —CH$_2$-phenyl-CH=CH$_2$.

26. The resin of embodiment 25, wherein $(Z)_n$ is an unsubstituted alkyl group having from 2 to 6 carbon atoms.

27. The resin of embodiment 22, wherein the resin has the structure:

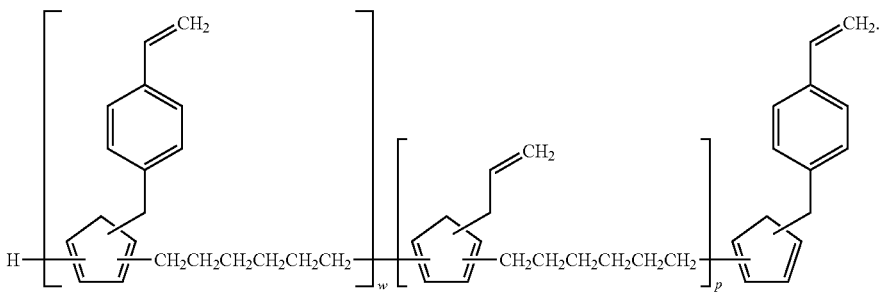

28. A resin having the structure defined by Formula (XIIC) or (XIID):

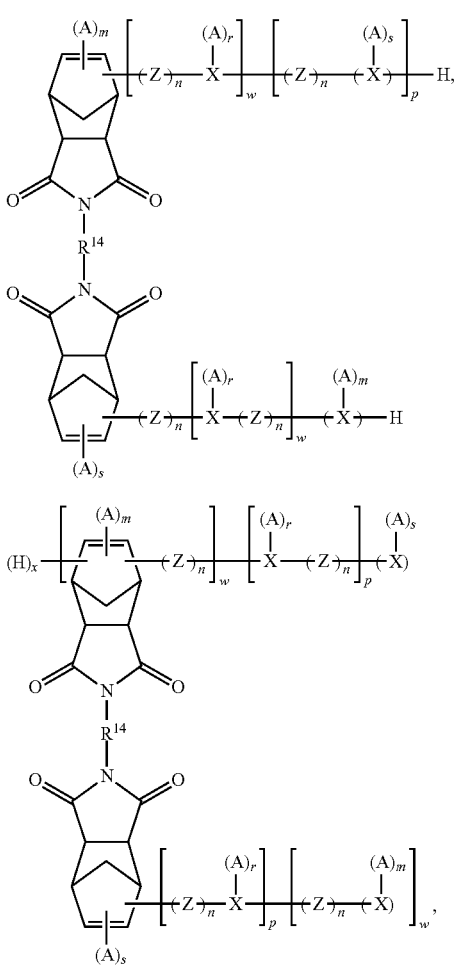

wherein
Z has the structure defined by Formula (IIIA):

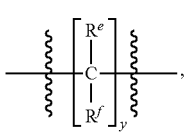

$R^e$ and $R^f$ are independently selected from H, F, or a straight chain or branched alkyl group having between 1 and 6 carbon atoms; and y is an integer ranging from between 1 and about 20;

m and s are independently an integer ranging from between 1 and about 5;

A is H or a moiety having a structure defined by Formula (IIC):

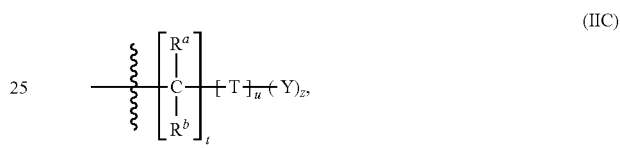

wherein $R^a$ and $R^b$ are independently selected from H, F, a $C_1$ to $C_{10}$ linear or cyclic, branched or straight chain aliphatic group;

T is —$CH_2$—, -phenyl, or —$CH_2$-phenyl;

Y is H, —$CH_3$, —CH=$CH_2$, —CH=CH—$CH_3$, or alkyne;

m is an integer ranging from 1 to 5;

n is 0 or 1;

p is 0 or an integer ranging from 1 to 150;

r is an integer ranging from 1 to 4;

t is 0 or an integer ranging from 1 to 20;

u is 0 or 1; and w is 0 or an integer ranging from 1 to 150;

x is 0 or 1, z is an integer ranging from 1 to 5;

$R^{13}$ is a saturated or unsaturated, straight-chain or branched, linear or cyclic, substituted or unsubstituted, aliphatic or aromatic group having between 1 and 50 carbon atoms, and which may be substituted with one or more heteroatoms selected from O, N, or S;

$R^{14}$ is a saturated or unsaturated, straight-chain or branched, linear or cyclic, substituted or unsubstituted, aliphatic or aromatic group having between 1 and 40 carbon atoms; —$(R^{13})_k$—$R^{15}$—, —$R^{15}$—$(R^{13})_k$— or —$R^{15}$—$(R^{13})_k$—$R^{15}$—;

each $R^{15}$ is independently a saturated or unsaturated, straight-chain or branched, linear or cyclic, substituted or unsubstituted, aliphatic or aromatic group having between 1 and 40 carbon atoms; and k is an integer ranging from 1 to 10.

29. A resin comprising the reaction product of (i) a compound selected from the group consisting of:

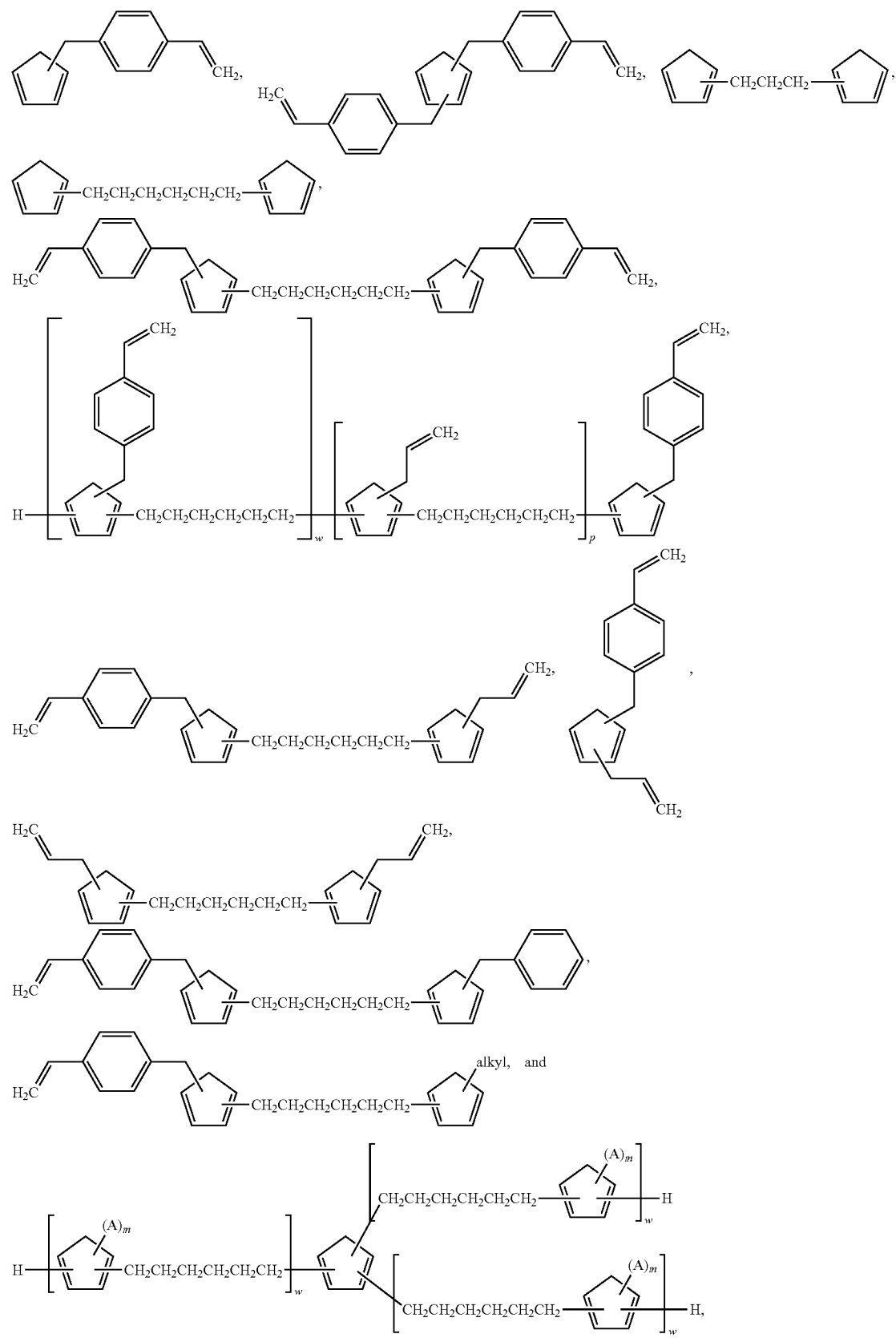
where w and p are independently an integer ranging from 1 to 150;
and (ii) a dienophile, wherein the dienophile is selected from the group consisting of a bis-maleimide, a derivative of a bis-maleimide, a maleic anhydride, a derivative of a maleic anhydride, a benzoquinone, a derivative of a benzoquinone, an acrylate, and a bis-acrylate.

30. A composition comprising a first resin of embodiment 22 and a second resin of embodiment 22, wherein each of the first and second resins are different.

31. The composition of embodiment 30, wherein the first resin is present in the composition in an amount ranging from between about 20% to about 80% by weight of the composition.

32. The composition of embodiment 30, wherein the first resin is present in the composition in an amount ranging from between about 30% to about 65% by weight of the composition.

33. The composition of embodiment 30, further comprising at least a third resin of any of embodiments 1 to 13, wherein the third resin is different than the first and second resins.

34. A polymer derived from a resin of embodiment 22.

35. The polymer of embodiment 34, wherein the resin comprises at least one A moiety terminating in one of a —CH=CH$_2$ group, a —CH=CH—CH$_3$ group, or an alkyne group.

36. The polymer of embodiment 34, further comprising an additive selected from the group consisting of adhesion agents, peroxides/crosslinking agents, antioxidants, flame retardants, diluents and fillers.

37. A co-polymer comprising a first resin of embodiment 22 and a second resin of embodiment 22, wherein the first and second resins are different.

38. A co-polymer comprising a resin of any of embodiment 22, and a second component that differs from the resin of embodiment 22, wherein the second component is selected from the group consisting of polyethylenes, polypropylenes, polybutylenes, low vinyl polybutadienes (predominantly 1,3 addition), high vinyl polybutadienes (significant 1,2 addition), polystyrenes, butadiene-styrene copolymers, SMA polymers, ABS polymers, polydicyclopentadienes, epoxies, polyurethanes, cyanate esters, poly(phenylene oxide), EPDM polymers, cyclic olefin copolymers (COC), polyimides, bismaleimides, phosphazenes, olefin-modified phosphazenes, acrylates, vinyl esters, polylactones, polycarbonates, polysulfones, polythioethers, polyetheretherketones (PEEK), polydimethylsiloxanes (PDMS), polyethylene terephthalates (PET), and polybutylene terephthalates (PBT), styrene, divinylbenzene, 1,2-bis(vinylphenyl)ethane, vinylbenzyl ether compounds, vinyl ether compounds, allyl ether compounds, vinylphenyl monomers, vinyl monomers, allyl monomers, or derivatives of such components.

39. A polymer or co-polymer comprising a resin of embodiment 22, wherein said polymer has a Dk value ranging from about 1.5 to about 3.

40. The polymer or co-polymer of embodiment 39, wherein the Dk values ranges from about 2.0 to about 2.8.

41. The polymer or copolymer of embodiment 39, wherein the Dk value is less than 2.6.

42. The polymer or copolymer of embodiment 39, wherein the Dk value is less than 2.4.

43. A polymer or co-polymer comprising a resin of embodiment 22, wherein said polymer has a Df value ranging from about 0.0001 to 0.004.

44. The polymer or copolymer of embodiment 43, wherein the Df value ranges from about 0.0009 to about 0.003.

45. The polymer or copolymer of embodiment 43, wherein the Df value is less than about 0.002.

46. The polymer or copolymer of embodiment 43, wherein the Df value is less than about 0.001.

47. A resin of Formula (IA) or (IB):

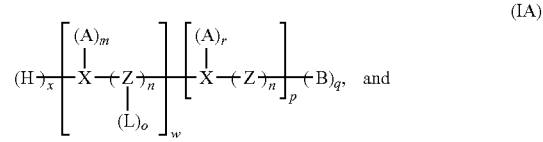

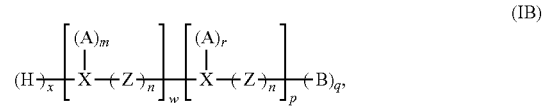

wherein

X is a moiety comprising a cyclopentadiene-based ring;

B is H or X(A)$_s$;

L is a leaving group.

each A is independently H, F, or a saturated or unsaturated, straight-chain or branched, linear or cyclic, substituted or unsubstituted, aliphatic or aromatic group having between 1 and 40 carbon atoms, and which may optionally comprise one or more heteroatoms;

Z is a bond or straight-chain or branched, substituted or unsubstituted, aliphatic group having between 1 and 20 carbon atoms;

m is an integer ranging from 1 to 5;

n is 0 or 1;

o is 0 or 1;

p is 0 or an integer ranging from 1 to 150;

q is 0 or 1;

r is an integer ranging from 1 to 4;

s is an integer ranging from 1 to 5;

w is 0 or an integer ranging from 1 to 150;

x is 0 or 1.

48. The resin of embodiment 47, wherein the resin has the structure defined by any of Formulas (IVA), (IVB), and (IVC),

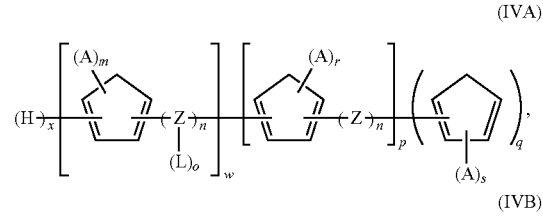

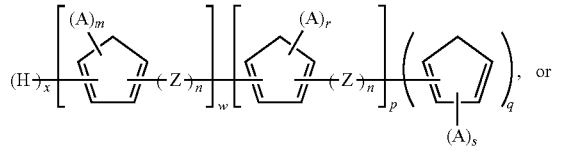

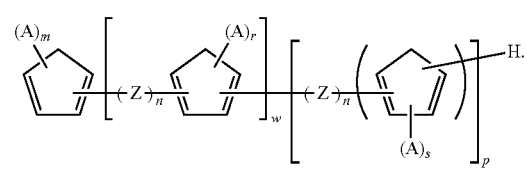

49. The resin of any of embodiments 47-48, wherein A has the structure defined by Formula (IIA):

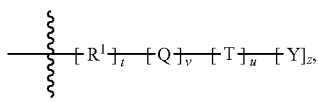
(IIA)

wherein R¹ is a bond, or a saturated or unsaturated straight-chain or branched, linear or cyclic, substituted or unsubstituted, aliphatic or aromatic group having from about 1 to about 10 carbon atoms,
Q is a bond or a linking group optionally comprising a heteroatom;
T is a bond or —$CH_2$—, -phenyl, or —$CH_2$-phenyl;
Y is H, —$CH_3$, —CH=$CH_2$, —CH=CH—$CH_3$, or an alkyne group;
t and v are independently 0 or an integer ranging from 1 to 20;
u is 0 or 1; and
z is an integer ranging from 1 to 5.

50. The resin of any of embodiments 47-49, wherein A has the structure defined by Formula (IIB):

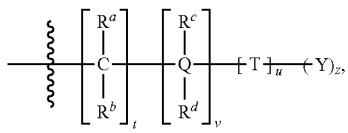
(IIB)

wherein
Q is C, O, N, or S;
$R^a$, $R^b$, $R^c$, $R^d$ are independently selected from H, F, a $C_1$ to $C_{10}$ linear or cyclic, saturated or unsaturated, branched or straight chain aromatic or aliphatic group;
T is —$CH_2$—, -phenyl, or —$CH_2$-phenyl;
Y is H, —$CH_3$, —CH=$CH_2$, —CH=CH—$CH_3$, or an alkyne group;
t and v are independently 0 or an integer ranging from 1 to 20;
u is 0 or 1; and
z is an integer ranging from 1 to 5.

51. The resin of any of embodiments 47-50 wherein when T is -phenyl, or —$CH_2$— phenyl, and Y is —CH=$CH_2$, —CH=CH—$CH_3$, or an alkyne group, z is 1.

52. The resin of any of embodiments any of embodiments 47-51, wherein a Dk value ranges from about 1.5 to about 3.

53. The resin of any of embodiments any of embodiments 47-51, wherein a Df value ranges from about 0.0001 to about 0.004

54. The resin of any of embodiments 47-53, wherein the resin is suitable for incorporation into a printed circuit board.

55. A resin having the structure:

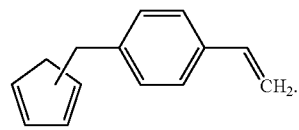

56. A resin having the structure:

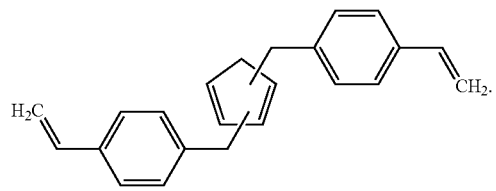

57. A resin having the structure:

58. A resin having the structure:

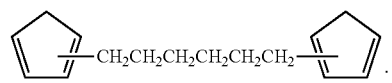

59. A resin having the structure:

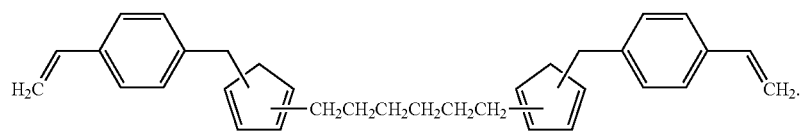

60. A resin having the structure:

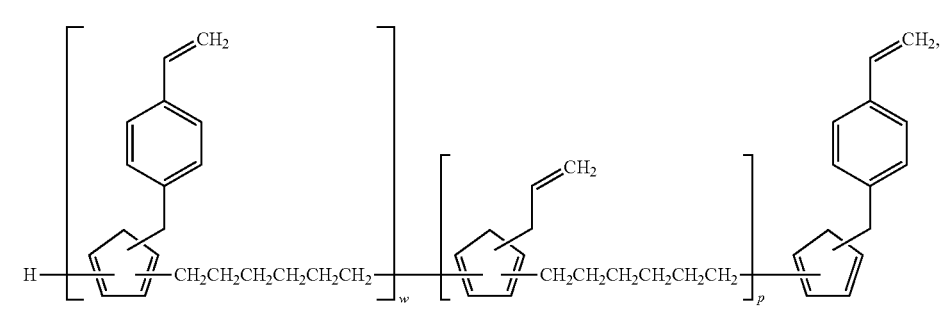

where w and p are independently 0 or an integer ranging from 1 to 150.

61. The resin of embodiment 60, wherein w and p are independently 0 or an integer ranging from 1 to 100.

62. The resin of embodiment 60, wherein w and p are independently 0 or an integer ranging from 1 to 50.

63. A resin having the structure:

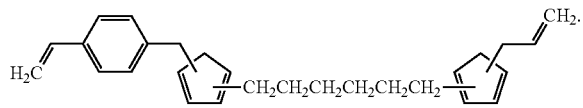

64. A resin having the structure:

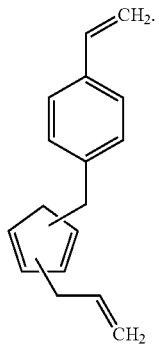

65. A resin having the structure:

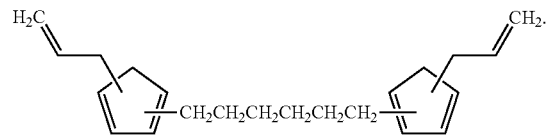

66. A resin having the structure:

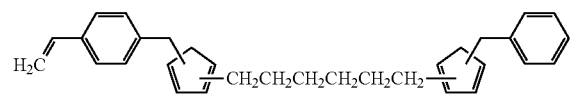

67. A resin having the structure:

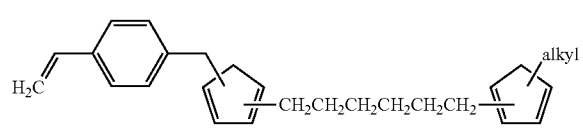

68. A resin having the structure:

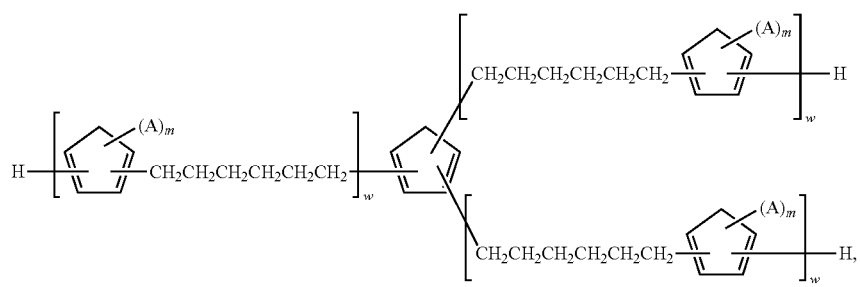

wherein each w is independently 0 or an integer ranging from 1 to 150.

69. A composition comprising a mixture of two different resins of any of embodiments 1-29 and 47-68.

70. The composition of embodiment 69, wherein a ratio of a first resin of any of embodiments 1-29 and 47-68 to a second resin of any of embodiments 1-29 and 47-68 ranges from about 10:90 to about 25:75.

71. The composition of any of embodiments 69-70, wherein the composition comprises a third resin of any of embodiments 1-29 and 47-68, wherein the third resin is different than either of the first or second resins.

72. The composition of any of embodiments 69-71, wherein the composition further comprises a polymer or copolymer having a structure which differences from the resins of any of embodiments 1-29 and 47-68.

73. The composition of any of embodiments 69-71, wherein the composition further comprises at least one polymer selected from the group consisting of polyethylenes, polypropylenes, polybutylenes, low vinyl polybutadienes, high vinyl polybutadienes, polystyrenes, butadiene-styrene copolymers, SMA polymers, ABS polymers, polydicyclopentadienes, epoxies, polyurethanes, cyanate esters, poly(phenylene oxide), EPDM polymers, cyclic olefin copolymers, polyimides, bismaleimides, phosphazenes, olefin-modified phosphazenes, acrylates, vinyl esters, polylactones, polycarbonates, polysulfones, polythioethers, polyetheretherketones, polydimethylsiloxanes, polyethylene terephthalates, and polybutylene terephthalates.

74. A polymer comprising two different resins of any of embodiments 1-29 and 47-68.

75. A blend comprising the polymer of embodiment 74, and a polymer or copolymer having a structure which differences from the resins of any of embodiments 1-29 and 47-68.

76. The blend of embodiment 75, wherein the polymer or copolymer is selected from the group consisting of polyethylenes, polypropylenes, polybutylenes, low vinyl polybutadienes, high vinyl polybutadienes, polystyrenes, butadiene-styrene copolymers, SMA polymers, ABS polymers, polydicyclopentadienes, epoxies, polyurethanes, cyanate esters, poly(phenylene oxide), EPDM polymers, cyclic olefin copolymers, polyimides, bismaleimides, phosphazenes, olefin-modified phosphazenes, acrylates, vinyl esters, polylactones, polycarbonates, polysulfones, polythioethers, polyetheretherketones, polydimethylsiloxanes, polyethylene terephthalates, and polybutylene terephthalates.

77. A product formed by reacting a resin of any of embodiments 1-29 and 47-68 with a dienophile.

78. The product of embodiment 77, wherein the dienophile comprises a nitroso group, a carbonyl group, or an imido group.

79. the product of embodiment 77, wherein the dienophile is an alkene.

80. The product of embodiment 79, wherein the alkene is an acrylate or a bis-acrylate.

81. The product of embodiment 77, wherein the dienophile is selected from the group consisting of methyl acrylate, ethyl acrylate, methyl methacrylate, ethyl methacrylate, vinyl acrylate, dimethyl fumarate, dimethyl maleate, diethyl fumarate, diethyl maleate, diphenyl fumarate, divinyl fumarate, divinylmaleate, acrolein, methyl vinyl ketone, divinylketone, acrylamide, N,N-dimethyl acrylamide, N,N-dimethyl methacrylamide, N,N-diethyl acrylamide, N,N-diethyl acrylamide, acrylonitrile, methacrylonitrile, 1,1-dicyanoethylene, maleonitrile, fiumaronitrile, and tetracyanoethylene.

82. The product of embodiment 77, wherein the dienophile is a bis-maleimide.

83. The product of embodiment 82, wherein the bis-maleimide has a structure selected from the group consisting of:

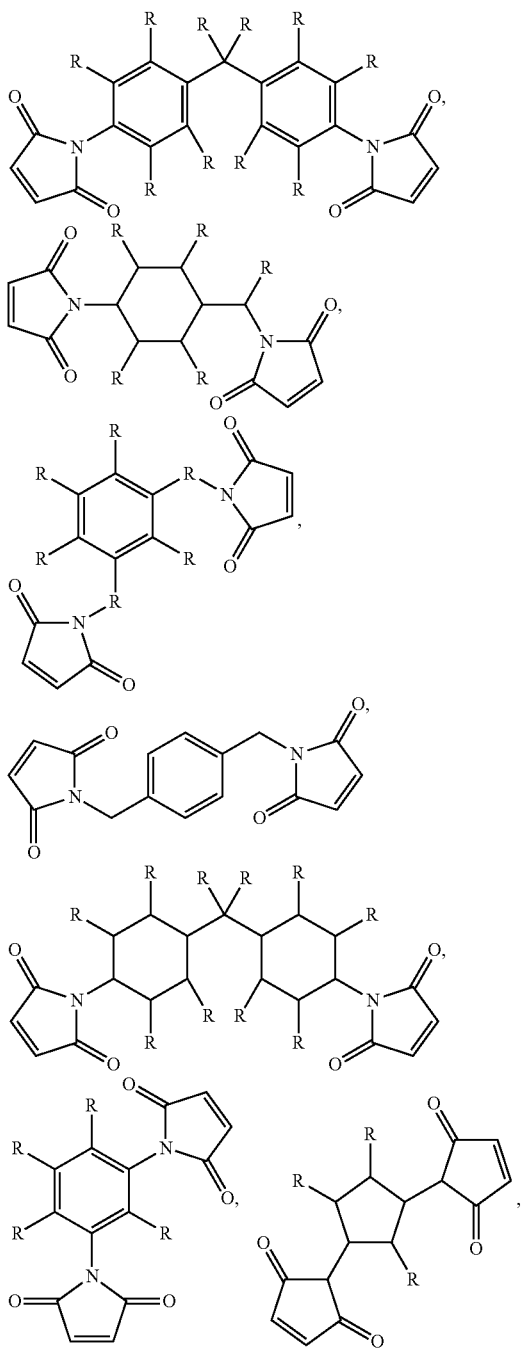

wherein each R is independently selected from hydrogen, an aryl group, a substituted aryl group, an aliphatic group, a substituted aliphatic group, a cyclic aliphatic group, and a substituted cyclic aliphatic group.

84. The product of embodiment 82, wherein the bis-maleimide is selected from the group consisting of 1,6'-bismaleimide-(2,2,4-trimethyl)hexane, 4,4'-Diphenylmethanebismaleimide, Polyphenylmethanebismaleimide, N,N'-(4-methyl-m-phenylene)-bismaleimide, N,N'-m-phenylenebismaleimide, bisphenol A diphenyl ether bismaleimide, 3,3'-dimethyl-5,5'-diethyl-4,4'-diphenylmethane bismaleimide, N,N'-[Methylenebis(2,6-diethyl-4,1-phenylene)]bis(maleimide, N,N'-[Methylenebis(2-isopropyl-6-methyl-4,1-phenylene)]bis(maleimide), 1,2-bis(maleimido)ethane, 1,4-bis(maleimido)butane, and 1,6-bis(maleimido)hexane.

85. The product of embodiment 77, wherein the dienophile is selected from the group consisting of maleic anhydride, derivatives of maleic anhydride, benzoquinone, and derivatives of benzoquinone.

86. The product of embodiment 77, wherein the dienophile is selected from the group consisting of 1,4-benzoquinone, 2-methylbenzoquinone, 2,3-dimethylbenzoquinone, 2,5-dimethylbenzoquinone, 2,6-dimethylbenzoquinone, 2,3,5-trimethylbenzoquinone, 2,3,5,6-tetramethylbenzoquinone, maleic anhydride, methyl maleic anhydride, dimethyl maleic anhydride, maleimide, N-methyl maleimide, N-ethyl maleimide, methyl maleimide, dimethyl maleimide, methyl-N-methyl maleimide, and dimethyl-N-methyl maleimide.

87. A substrate comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

88. The substrate of embodiment 87, wherein the substrate is a packaging for an integrated circuit.

89. The substrate of embodiment 88, wherein the packaging is a flip chip.

90. A laminate comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

91. A film comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

92. A film deposited on a substrate, the film comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

93. The film deposited on a substrate of embodiment 92, wherein the substrate is selected from the group consisting of a polymeric material, a metal, a composite, glass, and any combination thereof.

94. A prepreg comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

95. The prepreg of embodiment 95, further comprising at least one of woven glass, carbon, Kevlar, spectra, aramid, or quartz fibers.

96. A laminate comprising the prepreg of any of embodiments 94 and 95.

97. The laminate of embodiment 96, wherein the laminate has a glass transition temperature of greater than 150° C.

98. A printed circuit board comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

99. The printed circuit board of embodiment 98, wherein the printed circuit board is comprised of a multi-layer laminate.

100. The printed circuit board of any of embodiments 98-99, wherein the printed circuit board is rigid.

101. The printed circuit board of any of embodiments 98-99, wherein the printed circuit board is flexible.

102. An electronic device comprising the printed circuit board of any of embodiments 98-101.

103. The electronic device of embodiment 103, wherein the electronic device is an internet-of-things base station.

104. A radome comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

105. A radar structure or array comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

106. An antenna comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

107. The antenna of embodiment 106, wherein the antenna is a cellular phone antenna.

108. The antenna of embodiment 106, wherein the antenna is a satellite phone antenna.

109. An under fill adhesive composition comprising a resin of any of embodiments 1-29 and 47-68; a product of any of embodiments 77-86; a blend of any of embodiments 75-76; a polymer of any of embodiment 34-46 and 74; or a composition of any of embodiments 30-33 and 69-73.

110. A composition comprising a resin of any of embodiments 1-29 and 47-68 and a solvent.

111. The composition of embodiment 110, wherein the solvent is selected from the group consisting of dichloromethane, THF, and xylene, toluene, methyl ethyl ketone, acetone, methyl acetate, butyl acetate, methanol, ethanol, isopropanol, glycol ether PM, glycol ether EB, methyl isobutyl ketone, and methyl amyl ketone.

112. The composition of embodiment 111, wherein an amount of solvent within the composition ranges from about 1% to about 90% by total weight of the composition.

113. A kit comprising a first a composition of any of embodiments 110-112, and a second composition of any of embodiments 110-112, wherein the first composition and second composition comprise a different resin.

114. A kit comprising a composition of any of embodiments 110-112, and a dienophile.

115. The kit of embodiment 114, wherein the dienophile is a bis-maleimide.

116. The kit of embodiment 115, wherein the bis-maleimide has a structure selected from the group consisting of:

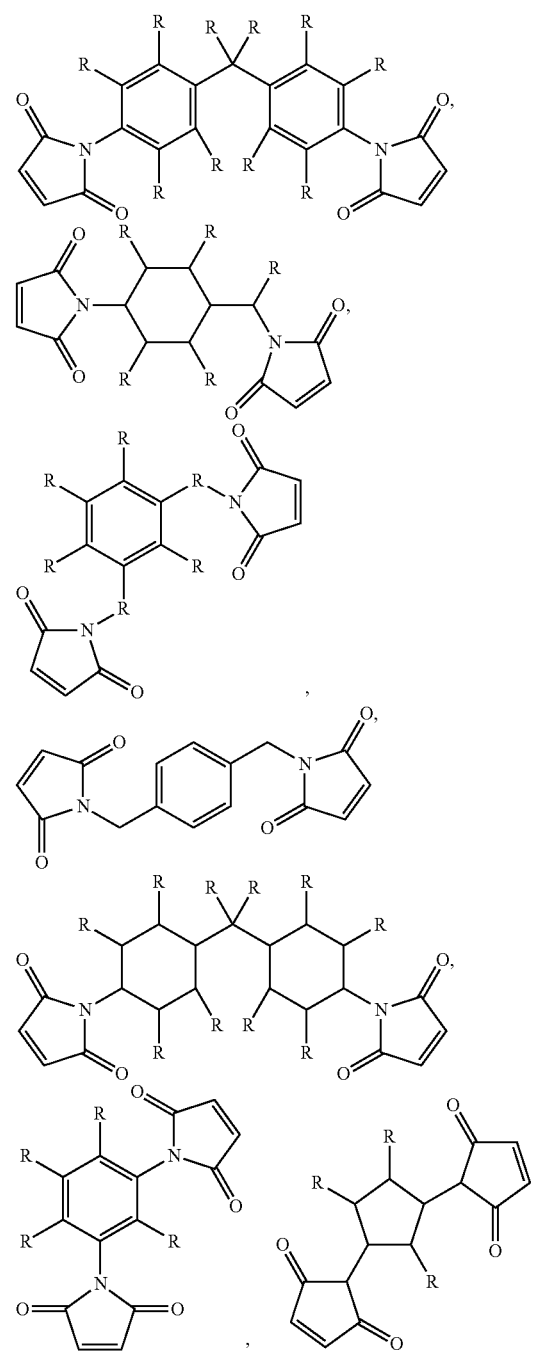

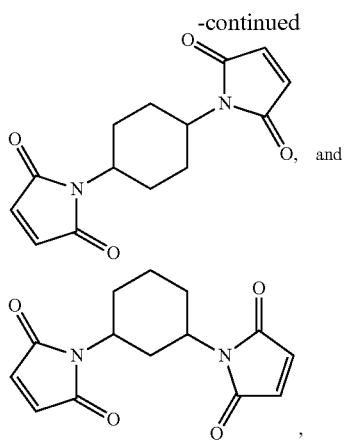

wherein each R is independently selected from hydrogen, an aryl group, a substituted aryl group, an aliphatic group, a substituted aliphatic group, a cyclic aliphatic group, and a substituted cyclic aliphatic group.

117. The kit of embodiment 115, wherein the bis-maleimide is selected from the group consisting of 1,6'-bismaleimide-(2,2,4-trimethyl)hexane, 4,4'-Diphenylmethanebismaleimide, Polyphenylmethanebismaleimide, N,N'-(4-methyl-m-phenylene)-bismaleimide, N,N'-m-phenylenebismaleimide, bisphenol A diphenyl ether bismaleimide, 3,3'-dimethyl-5,5'-diethyl-4,4'-diphenylmethane bismaleimide, N,N'-[Methylenebis(2,6-diethyl-4,1-phenylene)]bis(maleimide), N,N'-[Methylenebis(2-isopropyl-6-methyl-4,1-phenylene)]bis(maleimide), 1,2-bis(maleimido)ethane, 1,4-bis(maleimido)butane, and 1,6-bis(maleimido)hexane, and bis-maleimides derived from dimer acids.

118. A kit comprising a composition of any of embodiments 110-112, and a crosslinking agent.

119. The kit of embodiment 118, wherein the crosslinking agent is selected from the group consisting of triallyl cyanurate, triallyl isocyanurate, polybutadiene dimethacrylates, polybutadiene diacrylates, divinylbenzene, 1,2-bis(vinylphenyl)ethane, vinylbenzyl ether compounds, vinyl ether compounds, allyl ether compounds, vinylphenyl monomers, vinyl monomers, and allyl monomers.

120. A kit comprising a composition of any of embodiments 110-112, and a filler.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

The invention claimed is:

1. A resin comprising the reaction product of (i) a compound selected from the group consisting of:

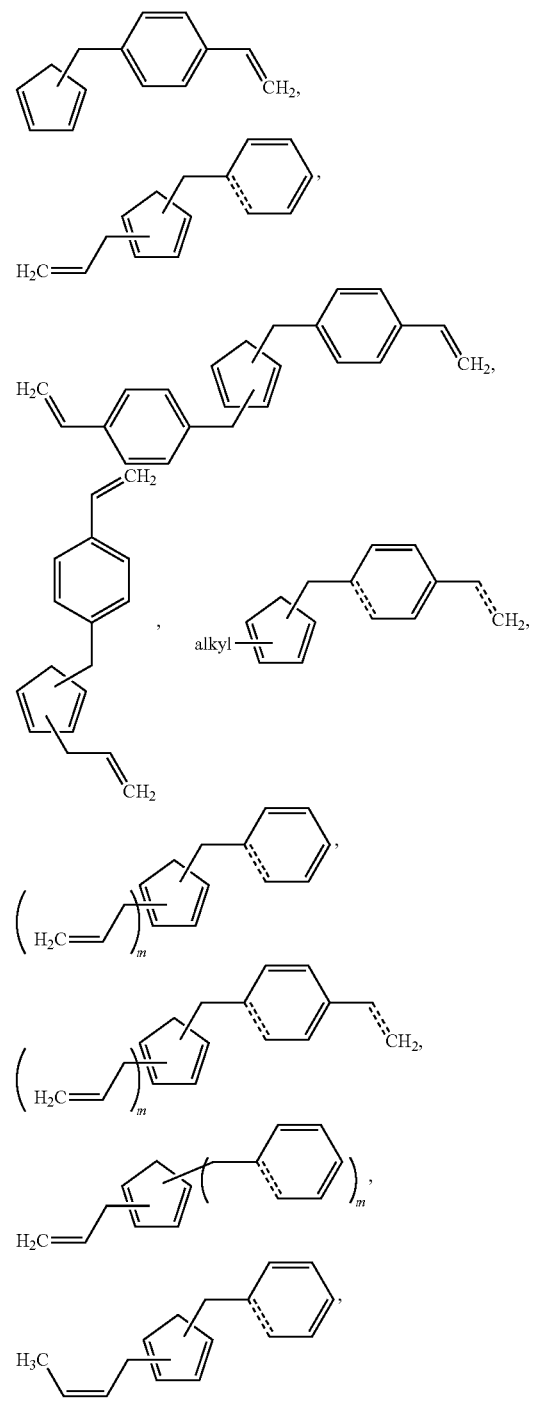

-continued

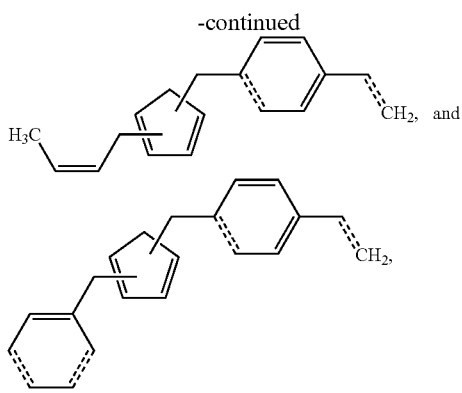

and polymers or co-polymers derived therefrom and (ii) a dienophile, wherein the dienophile is selected from the group consisting of a bis-maleimide or a derivative of a bis-maleimide, wherein m is an integer ranging from 1 to 5.

2. A polymer or copolymer derived from the resin of claim 1.

3. The resin of claim 1, wherein the bis-maleimide is selected from the group consisting of:

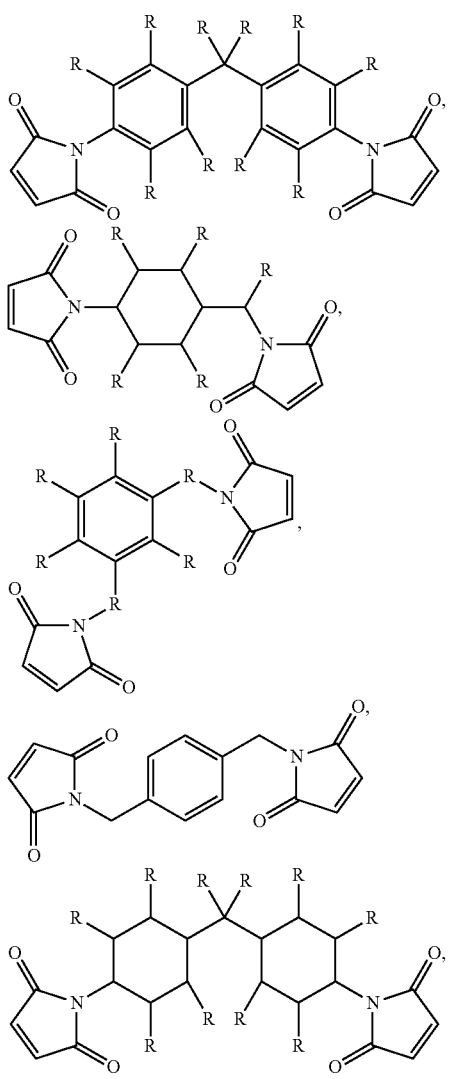

-continued

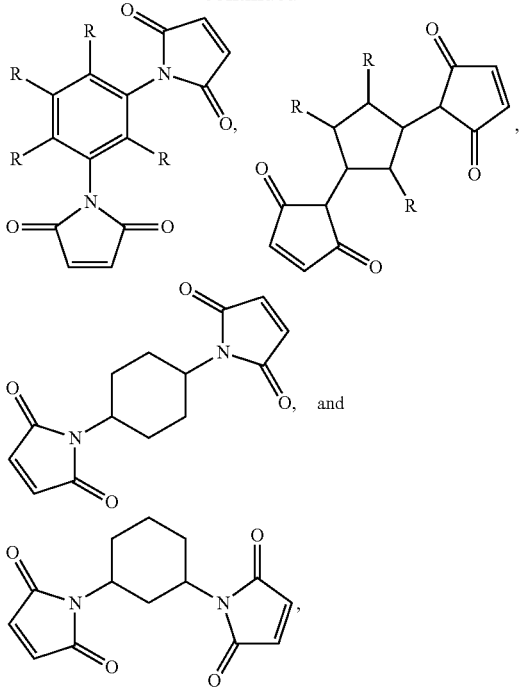

where each R is independently selected from hydrogen, aromatics, substituted aromatics, aliphatics, substituted aliphatics, cyclo-aliphatics, and substituted cyclo-aliphatics.

4. The resin of claim 1, wherein the bis-maleimide is selected from the group consisting of bis-maleimides include, but are not limited to: 1,6'-bismaleimide-(2,2,4-trimethyl)hexane, polyphenylmethanebismaleimide, N,N'-(4-methyl-m-phenylene)-bismaleimide, N,N'-m-phenylenebismaleimide, prepolymer bismaleimide resins, bisphenol A diphenyl ether bismaleimide, 3,3'-dimethyl-5,5'-diethyl-4,4'-diphenylmethane bismaleimide, N,N'-[Methylenebis(2,6-diethyl-4,1-phenylene)]bis(maleimide), N,N'-[Methylenebis(2-isopropyl-6-methyl-4,1-phenylene)]bis(maleimide), 1,2-bis(maleimido)ethane, 1,4-bis(maleimido)butane, and 1,6-bis(maleimido)hexane.

5. The resin of claim 1, wherein the compound is

6. The resin of claim 1, wherein the compound is selected from the group consisting of:

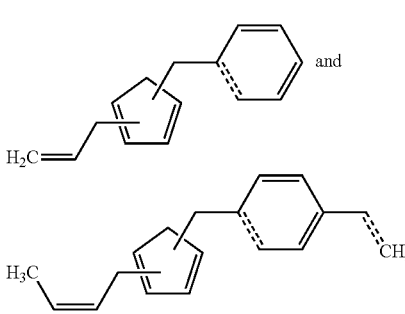

7. The resin of claim 1, wherein the compound is
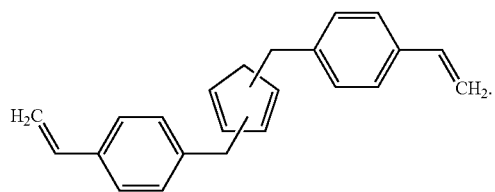
8. The resin of claim 1, wherein the compound is
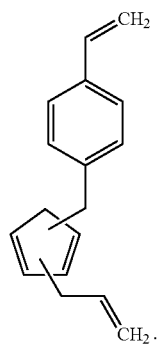
9. The resin of claim 1, wherein the compound is
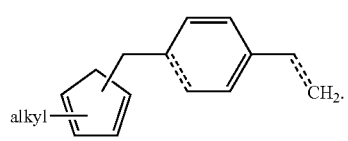
10. The resin of claim 1, wherein the compound is
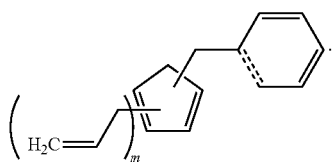
11. The resin of claim 1, wherein the compound is
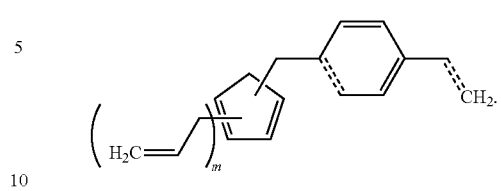
12. The resin of claim 1, wherein the compound is
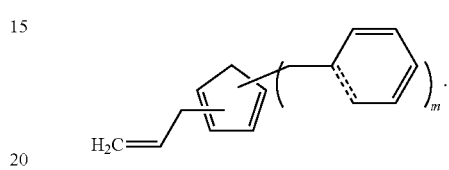
13. The resin of claim 1, wherein the compound is
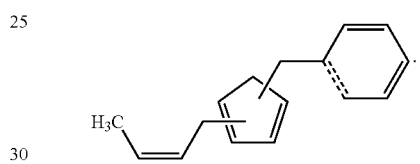
14. The resin of claim 1, wherein the compound is
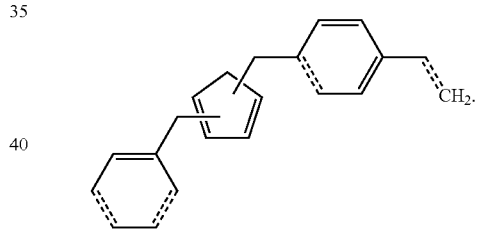
\* \* \* \* \*